US011819403B2

(12) United States Patent
Armer et al.

(10) Patent No.: US 11,819,403 B2
(45) Date of Patent: *Nov. 21, 2023

(54) DEVICES AND SYSTEMS FOR DOCKING A HEART VALVE

(71) Applicant: Edwards Lifesciences Corporation, Irvine, CA (US)

(72) Inventors: Dustin P. Armer, Costa Mesa, CA (US); Michael D. Franklin, Irvine, CA (US); Sergio Delgado, Irvine, CA (US); Abhijeet Joshi, Irvine, CA (US); Dinesh L. Sirimanne, Irvine, CA (US); Russell T. Joseph, Las Flores, CA (US); Eason Michael Abbott, Santa Monica, CA (US); Tram Ngoc Nguyen, Santa Ana, CA (US); Son V. Nguyen, Irvine, CA (US); Hien Tran Ngo, Irvine, CA (US); Vivian Tran, Santa Ana, CA (US); Charles L. Bowman, Rancho Santa Margarita, CA (US); Stanton J. Rowe, Newport Coast, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/456,523

(22) Filed: Nov. 24, 2021

(65) Prior Publication Data

US 2022/0079748 A1    Mar. 17, 2022

Related U.S. Application Data

(63) Continuation of application No. 16/290,628, filed on Mar. 1, 2019, now Pat. No. 11,191,638, which is a
(Continued)

(51) Int. Cl.
*A61F 2/24* (2006.01)
*A61F 2/95* (2013.01)

(52) U.S. Cl.
CPC .............. *A61F 2/2409* (2013.01); *A61F 2/24* (2013.01); *A61F 2/2418* (2013.01);
(Continued)

(58) Field of Classification Search
CPC ........ A61F 2/2409; A61F 2/24; A61F 2/2412; A61F 2/2436; A61F 2/2475; A61F 2002/0008; A61F 2/2418
See application file for complete search history.

(56) References Cited

U.S. PATENT DOCUMENTS

| 4,035,849 A | 7/1977 | Angell et al. |
| 4,790,843 A | 12/1988 | Carpentier et al. |

(Continued)

FOREIGN PATENT DOCUMENTS

| CA | 2767527 A1 | 1/2011 |
| CN | 101961273 B | 11/2012 |

(Continued)

OTHER PUBLICATIONS

Benson et al. "Three-Year Outcomes From the Harmony Native Outflow Tract Early Feasibility Study", Circ Cardiovasc Interv., 10 pgs., Jan. 2020.

*Primary Examiner* — Dinah Baria
(74) *Attorney, Agent, or Firm* — Calfee, Halter & Griswold LLP; Sean Seung Kyu Kim

(57) ABSTRACT

An expandable docking station frame includes a waist portion, a sealing portion connected to the waist portion, and a retaining portion connected to the sealing portion. The sealing portion is expandable radially outward of the waist portion to provide a seal against a first location of an inner surface of a circulatory system at a deployed position over
(Continued)

a range of sizes of expansion. The retaining portion is expandable radially outward to engage a second location of the inner surface of the circulatory system at the deployed position, to retain the docking station at the deployed position in the circulatory system. When the expandable docking station frame is in an expanded and unconstrained state, the sealing portion and the retaining portion are joined by a concave profile portion radially inward of each of a first outermost diameter of the sealing portion and a second outermost diameter of the retaining portion.

23 Claims, 76 Drawing Sheets

Related U.S. Application Data continuation of application No. 15/422,354, filed on Feb. 1, 2017, now Pat. No. 10,363,130.

(60) Provisional application No. 62/292,142, filed on Feb. 5, 2016.

(52) U.S. Cl.
CPC .......... *A61F 2/2436* (2013.01); *A61F 2/2475* (2013.01); *A61F 2/9517* (2020.05); *A61F 2220/0008* (2013.01); *A61F 2220/0075* (2013.01); *A61F 2250/006* (2013.01); *A61F 2250/0069* (2013.01)

(56) References Cited

U.S. PATENT DOCUMENTS

| | | | |
|---|---|---|---|
| 5,059,177 A | 10/1991 | Towne et al. |
| 5,411,552 A | 5/1995 | Andersen et al. |
| 5,554,185 A | 9/1996 | Block et al. |
| D380,266 S | 6/1997 | Boatman et al. |
| 5,840,081 A | 11/1998 | Andersen et al. |
| 6,040,416 A | 3/2000 | Sekharipuram et al. |
| 6,168,614 B1 | 1/2001 | Andersen et al. |
| 6,419,696 B1 | 7/2002 | Ortiz et al. |
| 6,425,916 B1 | 7/2002 | Garrison et al. |
| 6,432,134 B1 | 8/2002 | Anson et al. |
| 6,458,153 B1 | 10/2002 | Bailey et al. |
| 6,527,979 B2 | 3/2003 | Constantz et al. |
| 6,582,462 B1 | 6/2003 | Andersen et al. |
| 6,652,578 B2 | 11/2003 | Bailey et al. |
| 6,730,121 B2 | 5/2004 | Ortiz et al. |
| 6,797,002 B2 | 9/2004 | Spence et al. |
| 6,908,481 B2 | 6/2005 | Cribier |
| 7,018,408 B2 | 3/2006 | Bailey et al. |
| 7,037,334 B1 | 5/2006 | Hlavka et al. |
| 7,077,861 B2 | 7/2006 | Spence |
| 7,101,395 B2 | 9/2006 | Tremulis et al. |
| 7,125,421 B2 | 10/2006 | Tremulis et al. |
| 7,252,682 B2 | 8/2007 | Seguin |
| 7,445,632 B2 | 11/2008 | McGuckin, Jr. et al. |
| 7,585,321 B2 | 9/2009 | Cribier |
| 7,618,446 B2 | 11/2009 | Andersen et al. |
| 7,637,946 B2 | 12/2009 | Solem et al. |
| 7,708,775 B2 | 5/2010 | Rowe et al. |
| 7,737,060 B2 | 6/2010 | Strickler et al. |
| 7,749,266 B2 | 7/2010 | Forster et al. |
| 7,780,726 B2 | 8/2010 | Seguin |
| 7,785,366 B2 | 8/2010 | Maurer et al. |
| 7,951,195 B2 | 5/2011 | Antonsson et al. |
| 7,993,394 B2 | 8/2011 | Hariton et al. |
| D652,927 S | 1/2012 | Braido et al. |
| D653,341 S | 1/2012 | Braido et al. |
| 8,142,492 B2 | 3/2012 | Forster et al. |
| D660,433 S | 5/2012 | Braido et al. |
| D660,967 S | 5/2012 | Braido et al. |
| 8,182,530 B2 | 5/2012 | Huber |
| 8,236,049 B2 | 8/2012 | Rowe et al. |
| 8,323,335 B2 | 12/2012 | Rowe et al. |
| 8,377,115 B2 | 2/2013 | Thompson |
| 8,398,708 B2 | 3/2013 | Meiri et al. |
| 8,449,599 B2 | 5/2013 | Chau et al. |
| 8,449,605 B2 | 5/2013 | Lichtenstein et al. |
| 8,449,606 B2 | 5/2013 | Eliasen et al. |
| 8,591,573 B2 | 11/2013 | Barone |
| 8,652,145 B2 | 2/2014 | Maimon et al. |
| 8,652,202 B2 | 2/2014 | Alon et al. |
| 8,657,872 B2 | 2/2014 | Seguin |
| 8,663,322 B2 | 3/2014 | Keranen |
| 8,672,998 B2 | 3/2014 | Lichtenstein et al. |
| 8,685,086 B2 | 4/2014 | Navia et al. |
| 8,734,507 B2 | 5/2014 | Keranen |
| 8,784,481 B2 | 7/2014 | Alkhatib et al. |
| 8,801,776 B2 | 8/2014 | House et al. |
| 8,876,896 B2 | 11/2014 | Seguin et al. |
| 8,940,040 B2 | 1/2015 | Shahriari |
| 8,986,375 B2 | 3/2015 | Garde et al. |
| D730,520 S | 5/2015 | Braido et al. |
| D730,521 S | 5/2015 | Braido et al. |
| D732,666 S | 6/2015 | Nguyen et al. |
| 9,078,747 B2 | 7/2015 | Conklin |
| 9,095,434 B2 | 8/2015 | Rowe |
| 9,119,718 B2 | 9/2015 | Keranen |
| 9,155,619 B2 | 10/2015 | Liu et al. |
| 9,168,131 B2 | 10/2015 | Yohanan et al. |
| 9,192,471 B2 | 11/2015 | Bolling |
| 9,237,886 B2 | 1/2016 | Seguin et al. |
| 9,314,335 B2 | 4/2016 | Konno |
| D755,384 S | 5/2016 | Pesce et al. |
| 9,364,326 B2 | 6/2016 | Yaron |
| 9,463,268 B2 | 10/2016 | Spence |
| 9,474,599 B2 | 10/2016 | Keranen |
| 9,597,205 B2 | 3/2017 | Tuval |
| 9,622,863 B2 | 4/2017 | Karapetian et al. |
| D802,764 S | 11/2017 | Erzberger et al. |
| D802,765 S | 11/2017 | Erzberger et al. |
| D802,766 S | 11/2017 | Erzberger et al. |
| 9,867,700 B2 | 1/2018 | Bakis et al. |
| D834,193 S | 11/2018 | Erzberger et al. |
| D867,595 S | 11/2019 | Armer et al. |
| D889,653 S | 7/2020 | Erzberger et al. |
| D909,581 S | 2/2021 | Zeng et al. |
| D910,852 S | 2/2021 | Zeng et al. |
| 2002/0032481 A1 | 3/2002 | Gabbay |
| 2002/0107535 A1 | 8/2002 | Wei et al. |
| 2002/0151970 A1 | 10/2002 | Garrison et al. |
| 2002/0161377 A1 | 10/2002 | Rabkin |
| 2003/0023303 A1 | 1/2003 | Palmaz et al. |
| 2003/0040792 A1 | 2/2003 | Gabbay |
| 2003/0225420 A1 | 12/2003 | Wardle |
| 2004/0111006 A1 | 6/2004 | Alferness et al. |
| 2004/0210304 A1 | 10/2004 | Seguin et al. |
| 2004/0236411 A1 | 11/2004 | Sarac et al. |
| 2004/0260389 A1 | 12/2004 | Case et al. |
| 2005/0075731 A1 | 4/2005 | Artof et al. |
| 2005/0096736 A1 | 5/2005 | Osse et al. |
| 2005/0113910 A1 | 5/2005 | Paniagua |
| 2005/0119682 A1 | 6/2005 | Nguyen et al. |
| 2005/0119735 A1 | 6/2005 | Spence et al. |
| 2005/0137688 A1 | 6/2005 | Salahieh et al. |
| 2005/0137691 A1 | 6/2005 | Salahieh et al. |
| 2005/0137693 A1 | 6/2005 | Haug et al. |
| 2005/0137697 A1 | 6/2005 | Salahieh et al. |
| 2005/0149159 A1 | 7/2005 | Andreas et al. |
| 2005/0182486 A1 | 8/2005 | Gabbay |
| 2005/0203614 A1 | 9/2005 | Forster et al. |
| 2005/0203617 A1 | 9/2005 | Forster et al. |
| 2006/0025857 A1 | 2/2006 | Bergheim et al. |
| 2006/0149360 A1 | 7/2006 | Schwammenthal et al. |
| 2006/0195134 A1 | 8/2006 | Crittenden |
| 2006/0259136 A1 | 11/2006 | Nguyen et al. |
| 2006/0276813 A1 | 12/2006 | Greenberg |
| 2006/0287719 A1 | 12/2006 | Rowe et al. |
| 2007/0073389 A1 | 3/2007 | Bolduc et al. |
| 2007/0088431 A1 | 4/2007 | Bourang et al. |
| 2007/0203575 A1 | 8/2007 | Forster et al. |

(56) References Cited

U.S. PATENT DOCUMENTS

| | | |
|---|---|---|
| 2007/0213813 A1 | 9/2007 | Von Segesser et al. |
| 2007/0265700 A1 | 11/2007 | Eliasen et al. |
| 2007/0293808 A1 | 12/2007 | Williams et al. |
| 2008/0004696 A1 | 1/2008 | Vesely |
| 2008/0015671 A1 | 1/2008 | Bonhoeffer |
| 2008/0033542 A1 | 2/2008 | Antonsson et al. |
| 2008/0077235 A1 | 3/2008 | Kirson |
| 2008/0125853 A1 | 5/2008 | Bailey et al. |
| 2008/0208327 A1 | 8/2008 | Rowe |
| 2008/0208330 A1 | 8/2008 | Keranen |
| 2008/0319526 A1 | 12/2008 | Hill et al. |
| 2009/0099638 A1 | 4/2009 | Grewe |
| 2009/0192601 A1 | 7/2009 | Rafiee et al. |
| 2009/0319037 A1 | 12/2009 | Rowe et al. |
| 2010/0036484 A1 | 2/2010 | Hariton et al. |
| 2010/0049313 A1 | 2/2010 | Alon et al. |
| 2010/0145438 A1 | 6/2010 | Barone |
| 2010/0145440 A1 | 6/2010 | Keranen |
| 2010/0191326 A1 | 7/2010 | Alkhatib |
| 2010/0256737 A1 | 10/2010 | Pollock et al. |
| 2010/0312333 A1 | 12/2010 | Navia et al. |
| 2010/0318184 A1 | 12/2010 | Spence |
| 2011/0029072 A1 | 2/2011 | Gabbay |
| 2011/0040374 A1 | 2/2011 | Goetz et al. |
| 2011/0137397 A1 | 6/2011 | Chau et al. |
| 2011/0264196 A1 | 10/2011 | Savage et al. |
| 2012/0059458 A1 | 3/2012 | Buchbinder et al. |
| 2012/0071969 A1 | 3/2012 | Li et al. |
| 2012/0101571 A1 | 4/2012 | Thambar et al. |
| 2012/0123529 A1 | 5/2012 | Levi et al. |
| 2012/0150287 A1 | 6/2012 | Forster et al. |
| 2012/0283820 A1 | 11/2012 | Tseng et al. |
| 2013/0190865 A1 | 7/2013 | Anderson |
| 2014/0074299 A1 | 3/2014 | Endou et al. |
| 2014/0081394 A1 | 3/2014 | Keranen et al. |
| 2014/0088697 A1 | 3/2014 | Fogarty et al. |
| 2014/0114408 A1 | 4/2014 | Dwork |
| 2014/0172070 A1 | 6/2014 | Seguin |
| 2014/0194981 A1 | 7/2014 | Menk et al. |
| 2014/0277388 A1 | 9/2014 | Skemp |
| 2014/0303719 A1 | 10/2014 | Cox et al. |
| 2014/0343670 A1 | 11/2014 | Bakis et al. |
| 2014/0358222 A1 | 12/2014 | Gorman, III et al. |
| 2014/0379074 A1 | 12/2014 | Spence et al. |
| 2015/0018944 A1 | 1/2015 | O'Connell et al. |
| 2015/0025623 A1 | 1/2015 | Granada et al. |
| 2015/0073544 A1 | 3/2015 | Gorman, III et al. |
| 2015/0148893 A1 | 5/2015 | Braido et al. |
| 2015/0148895 A1 | 5/2015 | Stacchino et al. |
| 2015/0157455 A1 | 6/2015 | Hoang et al. |
| 2015/0190227 A1 | 7/2015 | Johnson et al. |
| 2015/0230921 A1 | 8/2015 | Chau et al. |
| 2015/0245910 A1 | 9/2015 | Righini et al. |
| 2015/0272737 A1 | 10/2015 | Dale et al. |
| 2015/0282931 A1 | 10/2015 | Brunnett et al. |
| 2015/0335428 A1 | 11/2015 | Keranen |
| 2015/0335430 A1 | 11/2015 | Loulmet et al. |
| 2015/0374493 A1 | 12/2015 | Yaron et al. |
| 2016/0000591 A1 | 1/2016 | Lei et al. |
| 2016/0015514 A1 | 1/2016 | Lashinski et al. |
| 2016/0074165 A1 | 3/2016 | Spence et al. |
| 2016/0095705 A1 | 4/2016 | Keranen et al. |
| 2016/0143732 A1 | 5/2016 | Glimsdale |
| 2016/0184095 A1 | 6/2016 | Spence et al. |
| 2016/0199177 A1 | 7/2016 | Spence et al. |
| 2016/0256276 A1 | 9/2016 | Yaron |
| 2016/0346080 A1 | 12/2016 | Righini et al. |
| 2017/0007399 A1 | 1/2017 | Keranen |
| 2017/0007402 A1 | 1/2017 | Zerkowski et al. |
| 2017/0056149 A1 | 3/2017 | Rajpara et al. |
| 2017/0128197 A1 | 5/2017 | Bialas et al. |
| 2017/0156839 A1 | 6/2017 | Cooper et al. |
| 2017/0156859 A1 | 6/2017 | Chang et al. |
| 2017/0217385 A1 | 8/2017 | Rinkleff et al. |
| 2017/0231765 A1 | 8/2017 | Desrosiers et al. |
| 2017/0258584 A1 | 9/2017 | Chang et al. |
| 2017/0266005 A1 | 9/2017 | McGuckin, Jr. |
| 2017/0273788 A1 | 9/2017 | O'Carroll et al. |
| 2017/0273789 A1 | 9/2017 | Yaron et al. |
| 2017/0281337 A1 | 10/2017 | Campbell |
| 2018/0000580 A1 | 1/2018 | Wallace et al. |
| 2018/0085217 A1 | 3/2018 | Lashinski et al. |
| 2018/0206074 A1 | 7/2018 | Tanasa et al. |
| 2018/0289481 A1 | 10/2018 | Dolan |
| 2018/0303606 A1 | 10/2018 | Rothstein et al. |
| 2018/0318073 A1 | 11/2018 | Tseng et al. |
| 2018/0318080 A1 | 11/2018 | Quill et al. |

FOREIGN PATENT DOCUMENTS

| | | |
|---|---|---|
| CN | 104188737 A | 12/2014 |
| CN | 205322549 U | 6/2016 |
| CN | 205322550 U | 6/2016 |
| CN | 205339217 U | 6/2016 |
| DE | 19532846 A1 | 3/1997 |
| DE | 19907646 A1 | 8/2000 |
| EP | 0592410 B1 | 10/1995 |
| EP | 0850607 A1 | 7/1998 |
| EP | 1432369 A1 | 6/2004 |
| EP | 1521550 A2 | 4/2005 |
| EP | 1296618 B1 | 1/2008 |
| EP | 2218403 A1 | 8/2010 |
| EP | 1827314 B1 | 12/2010 |
| EP | 2620125 A1 | 7/2013 |
| EP | 2726018 A2 | 5/2014 |
| EP | 2806829 A2 | 12/2014 |
| EP | 2893905 A1 | 7/2015 |
| JP | 2015128592 A | 7/2015 |
| WO | 9117720 A1 | 11/1991 |
| WO | 0041652 A1 | 7/2000 |
| WO | 0149213 A2 | 7/2001 |
| WO | 0154625 A1 | 8/2001 |
| WO | 0247575 A2 | 6/2002 |
| WO | 03028558 A2 | 4/2003 |
| WO | 2005084595 A1 | 9/2005 |
| WO | 2006011127 A2 | 2/2006 |
| WO | 2005102015 A3 | 4/2007 |
| WO | 2007067942 A1 | 6/2007 |
| WO | 2008124844 A1 | 10/2008 |
| WO | 2009155561 A2 | 12/2009 |
| WO | 2010121076 A2 | 10/2010 |
| WO | 2012063228 A1 | 5/2012 |
| WO | 2013110722 A2 | 8/2013 |
| WO | 2013114214 A2 | 8/2013 |
| WO | 2013134214 A1 | 9/2013 |
| WO | 2015023579 A1 | 2/2015 |
| WO | 2015023862 A2 | 2/2015 |
| WO | 2015055052 A1 | 4/2015 |
| WO | 2015127264 A1 | 8/2015 |
| WO | 2015198125 A1 | 12/2015 |
| WO | 2016038017 A1 | 3/2016 |
| WO | 2016040881 A1 | 3/2016 |
| WO | 2016130820 A1 | 8/2016 |
| WO | 2016149997 A1 | 9/2016 |
| WO | 2016149998 A1 | 9/2016 |
| WO | 2017103833 A1 | 6/2017 |
| WO | 2017136778 A1 | 8/2017 |

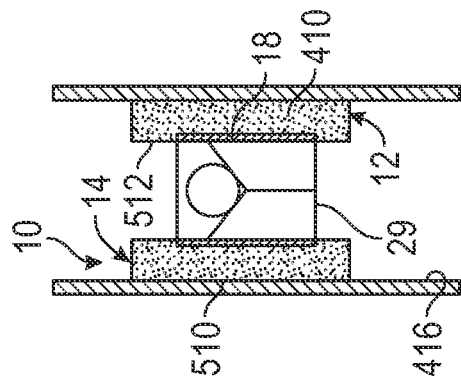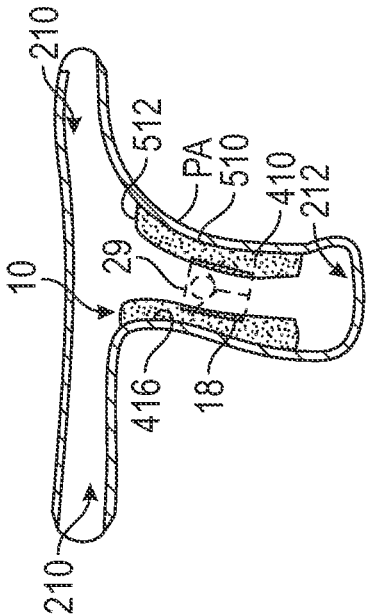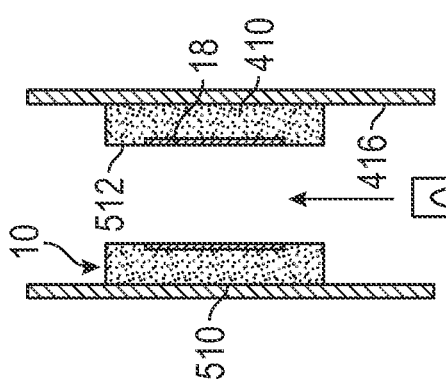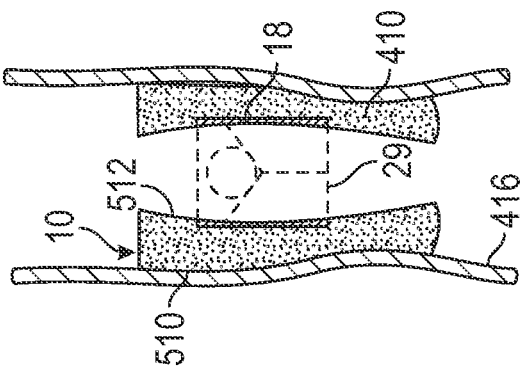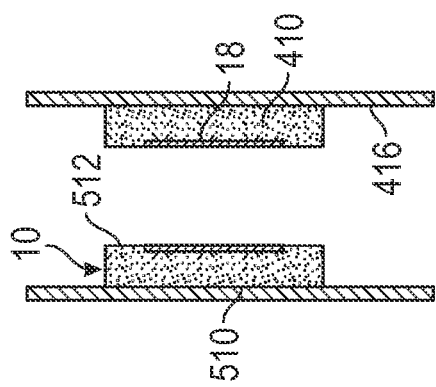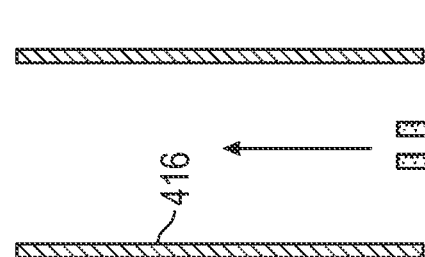

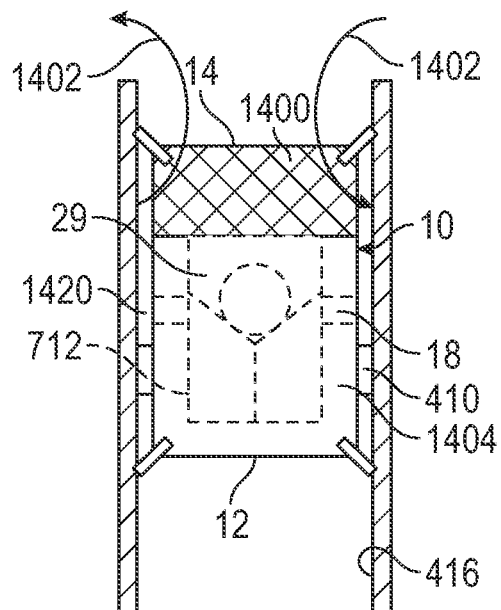
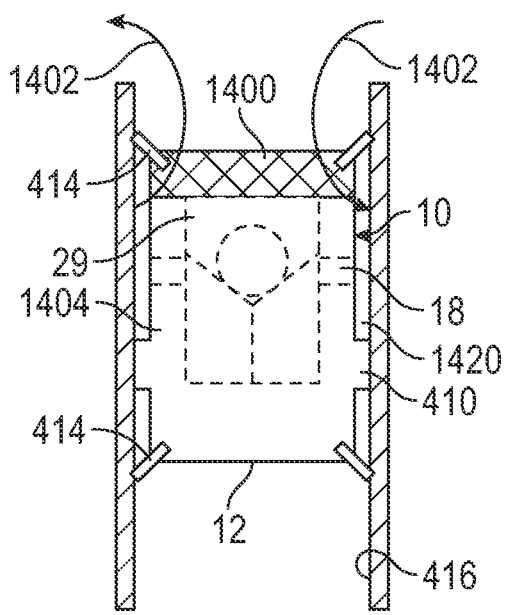
FIG. 14A  FIG. 14B
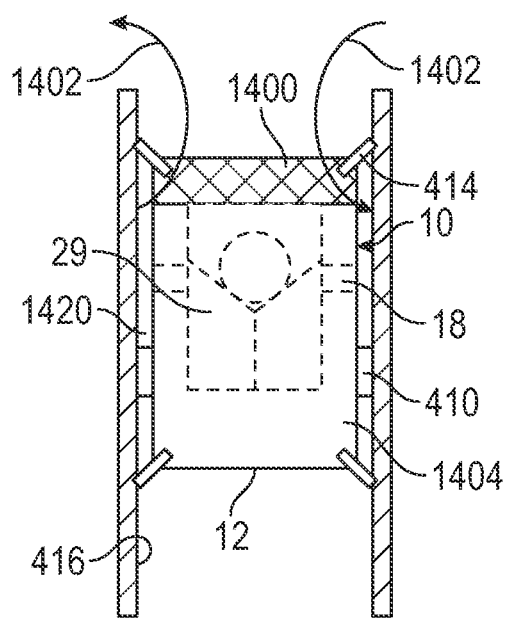
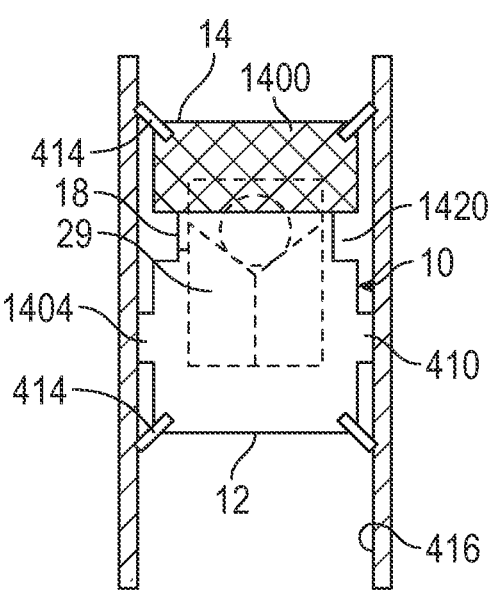
FIG. 14C  FIG. 14D

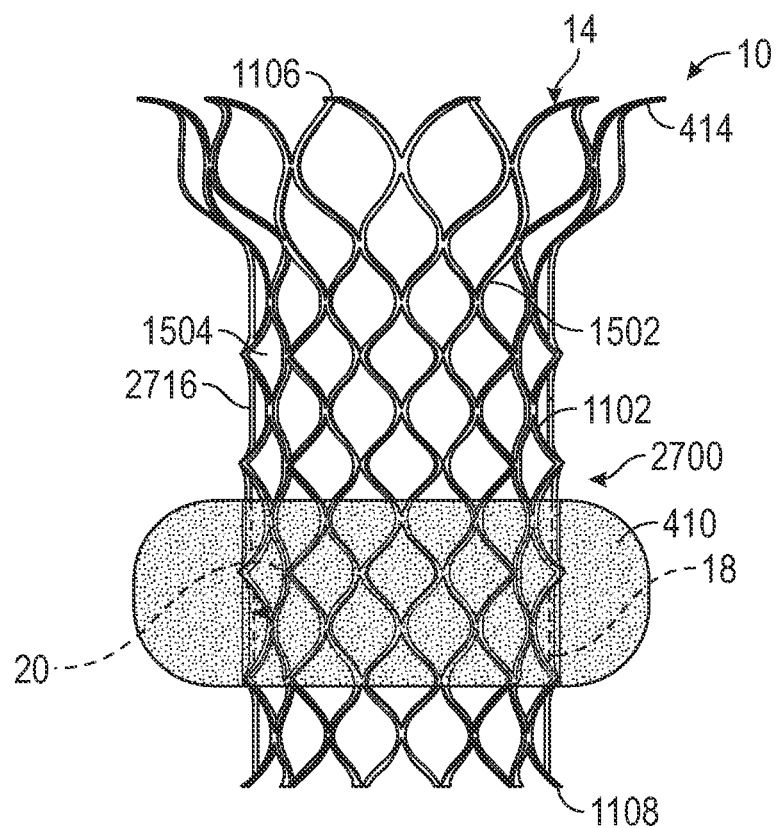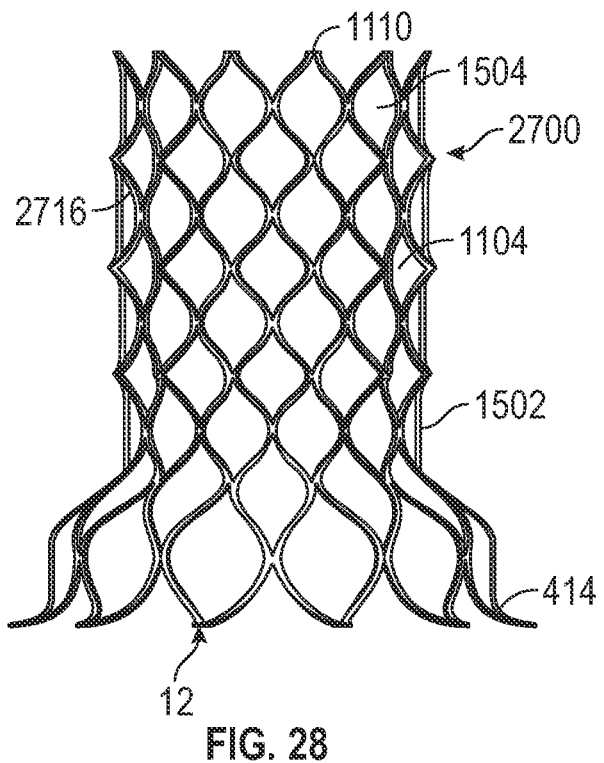
FIG. 28

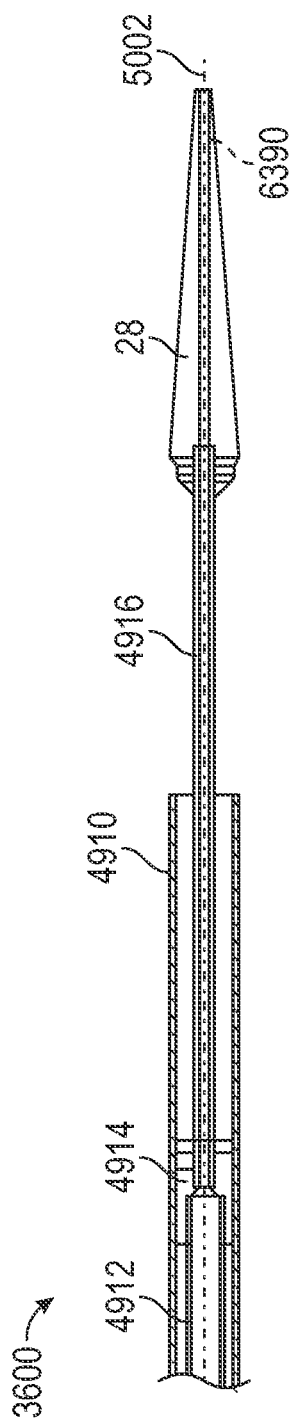
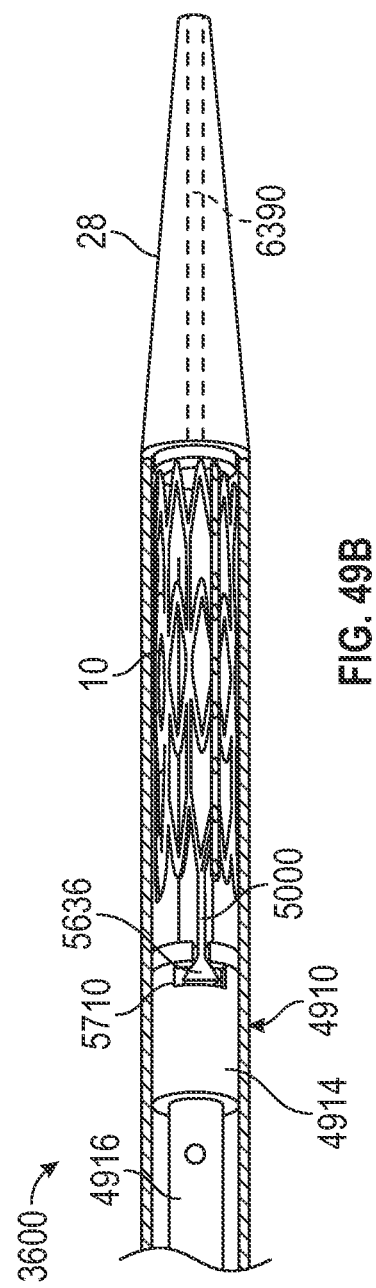
FIG. 49A
FIG. 49B

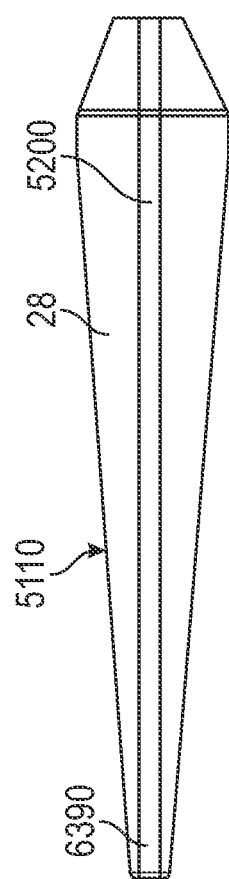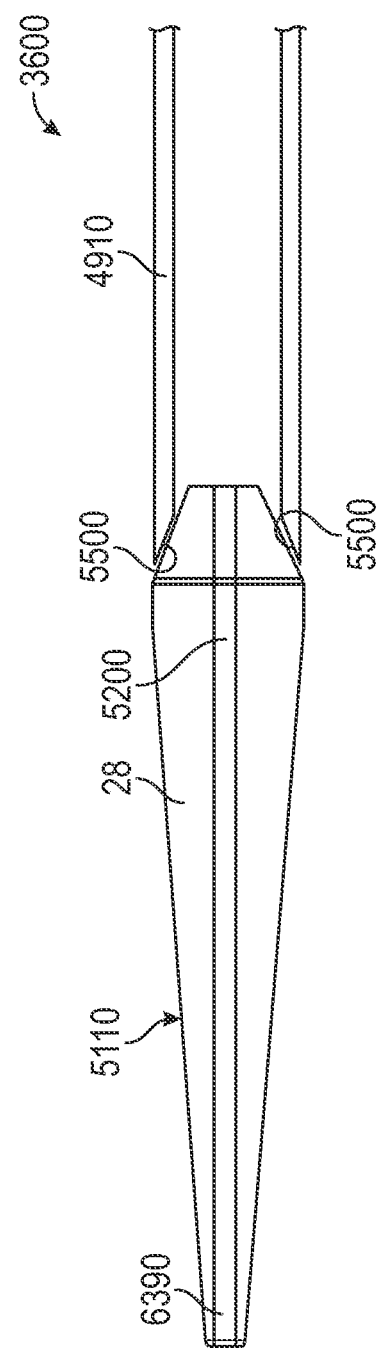

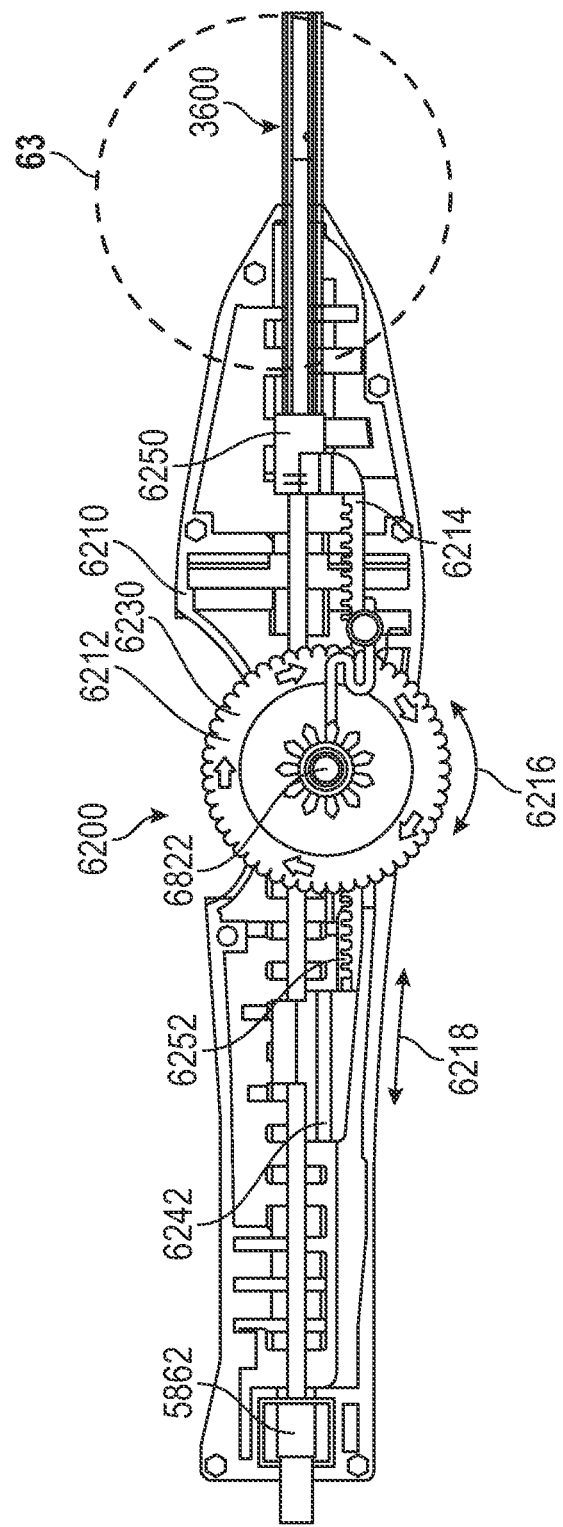
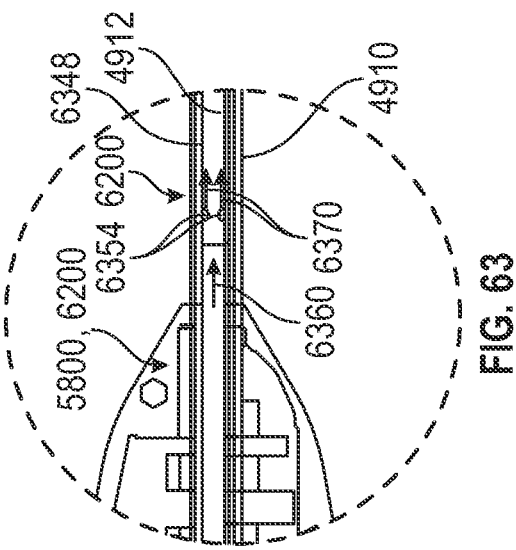

DEVICES AND SYSTEMS FOR DOCKING A HEART VALVE

RELATED APPLICATIONS

The present application is a continuation of U.S. patent application Ser. No. 16/290,628, filed on Mar. 1, 2019, which is a continuation of U.S. patent application Ser. No. 15/422,354, filed on Feb. 1, 2017, now U.S. Pat. No. 10,363,130, which claims the benefit of U.S. provisional application Ser. No. 62/292,142, filed on Feb. 5, 2016. Each of the foregoing applications is incorporated herein by reference in its entirety.

FIELD OF THE INVENTION

The present invention relates to heart valves and, in particular, docking stations/stents, delivery systems, and methods for use in implanting a heart valve, e.g., a transcatheter heart valve ("THV").

BACKGROUND OF THE INVENTION

Prosthetic heart valves can be used to treat cardiac valvular disorders. The native heart valves (the aortic, pulmonary, tricuspid and mitral valves) serve critical functions in assuring the forward flow of an adequate supply of blood through the cardiovascular system. These heart valves can be rendered less effective by congenital, inflammatory, or infectious conditions. Such conditions can eventually lead to serious cardiovascular compromise or death. For many years the definitive treatment for such disorders was the surgical repair or replacement of the valve during open heart surgery.

A transcatheter technique can also be used for introducing and implanting a prosthetic heart valve using a flexible catheter in a manner that is less invasive than open heart surgery. In this technique, a prosthetic valve can be mounted in a crimped state on the end portion of a flexible catheter and advanced through a blood vessel of the patient until the valve reaches the implantation site. The valve at the catheter tip can then be expanded to its functional size at the site of the defective native valve, such as by inflating a balloon on which the valve is mounted. Alternatively, the valve can have a resilient, self-expanding stent or frame that expands the valve to its functional size when it is advanced from a delivery sheath at the distal end of the catheter.

Transcatheter heart valves (THVs) may be appropriately sized to be placed inside most native aortic valves. However, with larger native valves, blood vessels, and grafts, aortic transcatheter valves might be too small to secure into the larger implantation or deployment site. In this case, the transcatheter valve may not be large enough to sufficiently expand inside the native valve or other implantation or deployment site to be secured in place.

Replacing the pulmonary valve, which is sometimes referred to as the pulmonic valve, presents significant challenges. The geometry of the pulmonary artery can vary greatly from patient to patient. Typically, the pulmonary artery outflow tract after corrective surgery is too wide for effective placement of a prosthetic heart valve.

SUMMARY

This summary is meant to provide examples and is not intended to be limiting of the scope of the invention in any way. For example, any feature included in an example of this summary is not required by the claims, unless the claims explicitly recite the feature. The description discloses exemplary embodiments of expandable docking stations for an expandable valve, catheters for the expandable docking stations, and handles for the catheters. The docking stations, catheters, and handles can be constructed in a variety of ways.

In one embodiment, for example, a docking station can include a valve seat, one or more sealing portions, and one or more retaining portions. In one embodiment, the valve seat can be substantially unexpandable beyond a deployed size, i.e., the diameter of the valve seat may only be able to increase a maximum of 0-4 mm. The one or more sealing portions can be connected to the valve seat and extend radially outward of the valve seat. The one or more sealing portions can be constructed to expand and extend outward of the valve seat and provide a seal over a range of sizes (e.g., over a range of sizes of expansion and/or over a range of sizes within the circulatory system or vasculature, for example, it may be able to provide a seal when expanding in different blood vessels or locations of a variety of shapes and sizes). The one or more retaining portions can be connected to the one or more sealing portions. The one or more retaining portions can be configured to retain the docking station at a deployed position. The expandable docking station can expand and provide a seal over a range from 27 mm to 38 mm. The expandable docking station can expand radially outwardly to varying degrees along its length L. The valve seat and the one or more sealing portions can act as an isolator that reduces or prevents radial outward forces of an expandable valve in the valve seat from being transferred to the one or more sealing portions or the one or more retaining portions. The docking station can be configured such that pressure of blood enhances the retention by the retaining portions. The one or more retaining portions can be configured such that force applied by at least one of the one or more retaining portions at the deployed position is in proportion to the pressure of blood acting on the docking station. The one or more retaining portions can be configured such that force applied by at least one of the one or more retaining portions is greater when the heart is in a diastolic phase than when the heart is in the systolic phase. The valve seat can be formed by a suture, ring, band, structural arrangement, material, foam, and in other ways. The sealing portion can comprise a portion of a metal frame covered with a fabric, polymer, and/or other material. The sealing portion can comprise an open cell foam. A portion of the docking station can be permeable to blood and a portion of the docking station can be impermeable to blood. A portion of the docking station that is impermeable to blood can extend from at least the valve seat to at least the sealing portion. The docking station can be adjustable in length. The docking station can include a first half that a second half of the docking station can adjustably extend into to adjust the length. The one or more retaining portions can extend radially outward of the one or more sealing portions when the docking station is in an unconstrained state. Other features described elsewhere in this disclosure may also be included.

In one exemplary embodiment, a system can include an expandable docking station and an expandable valve. The expandable docking station can include a valve seat, one or more sealing portions, and one or more retaining portions. The valve seat can expand to a deployed size. The one or more sealing portions can be connected to the valve seat and can be constructed to expand and extend radially outward of the valve seat and provide a seal over a range of sizes of expansion. The one or more retaining portions can be connected to the one or more sealing portions. The one or more retaining portions can be configured to retain the docking station at a deployed position. The expandable valve can include an expandable frame and a valve element. The expandable frame can be expanded to engage the valve seat of the docking station. The valve element can be connected to the expandable frame. The expandable docking station and expandable valve can be configured such that, when implanted in a portion of a circulatory system, a radial outward force applied by the sealing portions to the portion of the circulatory system, when sealing portions are within the range of sizes, is less than ½ (and can be less than ⅓, less than ¼, less than ⅛, or less than ¹/₁₀) of a radial outward force applied by the expandable frame to the valve seat. The expandable docking station can be configured such that, when implanted in the portion of the circulatory system, the diameter of the valve seat is not increased more than 3M (or not more than 1 mm, 2 mm, or 4 mm) by the radial outward force applied by the expandable frame to the valve seat. The range of sizes of the sealing portions can be from 27 mm to 38 mm. The expandable docking station can be configured to expand radially outwardly to varying degrees along its length L when implanted in the portion of the circulatory system.

The expandable docking station can be configured such that, when implanted in the portion of the circulatory system, pressure of blood on the expandable docking station enhances retention by the retaining portions. The expandable docking station can be configured such that force applied by the retaining portions, when implanted in the portion of the circulatory system, is in proportion to the pressure of blood acting on the assembly. The expandable docking station can be configured such that force applied by the retaining portions, when implanted in the portion of the circulatory system, is greater when the heart is in a diastolic phase than when the heart is in the systolic phase. The valve seat can be formed by a suture, ring, band, structural arrangement, material, foam, and in other ways. The sealing portion can comprise a portion of a metal frame covered with a fabric. The sealing portion can comprise an open cell foam. A portion of the docking station can be permeable to blood and a portion of the docking station can be impermeable to blood. A portion of the docking station that is impermeable to blood can extends from at least the valve seat to at least the sealing portion. The docking station can have an overall length that is adjustable. The docking station can include a first half (i.e., portion) that a second half (i.e., portion) of the docking station can adjustably extend into to adjust the overall length. In other words, the length of the docking station can be adjusted by moving the second half/portion relative to the first half/portion, and the first half/portion may be moved independently from the second half/portion (e.g., one half/portion may remain in place while the other half/portion moves). If one of the first or second halves/portions extends inside the other half/portion and overlaps to adjust the length, the first half/portion and second half/portion may be adjusted to change the amount/length of overlap between the two. The one or more retaining portions can extend radially outward of the one or more sealing portion when the docking station is in an unconstrained state. Other features described elsewhere in this disclosure may also be included.

In one exemplary embodiment, a method can include expanding a docking station and expanding a valve in the docking station. The docking station can be expanded such that a valve seat of the docking station expands to a valve seat deployed size and a sealing portion expands to a sealing size that is within a range of sealing sizes. A frame of an expandable valve can be expanded to engage the valve seat of the docking station. A radial outward force applied by the sealing portions over the range of sealing sizes can be less than ½ (and can be less than ⅓, less than ¼, less than ⅛, or less than ¹/₁₀) of a radial outward force applied by the expandable frame to the valve seat after expanding the frame. The valve seat of the docking station can be configured such that a diameter of the valve seat is not increased more than 2 mm (or not more than 1 mm, 3 mm, or 4 mm) by the radial outward force applied by the expandable frame to the valve seat. The range of sealing sizes of the docking station can be from 27 mm to 38 mm. The valve seat can be formed by a suture, ring, band, structural arrangement, material, foam, and in other ways. Other features/steps described elsewhere in this disclosure may also be included.

In one exemplary embodiment a system can include an expandable docking station and an expandable valve. The expandable docking station can include a valve seat, one or more sealing portions, and one or more retaining portions. The valve seat can expand to a deployed size. The one or more sealing portions can be connected to the valve seat and can extend radially outward of the valve seat. The one or more sealing portions can be constructed to expand outward of the valve seat and provide a seal over a range of sizes. The one or more retaining portions can be connected to the one or more sealing portions. The one or more retaining portions can be configured to retain the docking station at a deployed position. The expandable valve can comprise an expandable frame and a valve element. The expandable frame can expand to engage the valve seat of the docking station. The valve element can be connected to the expandable frame. A pressure of blood acting on the valve and docking station can enhance retention by the retaining portions at the deployed position.

The valve seat can be configured such that the valve seat is not substantially expanded radially outwardly by a radially outward force of the expandable valve. The range of sizes of the sealing portions can be from 27 mm to 38 mm. The docking station can be configured to expand radially outwardly to varying degrees along its length L. Force applied by the retaining portions can be in proportion to the pressure of blood acting on the assembly. Force applied by the retaining portions can be greater when the heart is in a diastolic phase than when the heart is in the systolic phase. The valve seat can be formed by a suture, ring, band, structural arrangement, material, foam, and in other ways. The sealing portion can comprise a portion of a metal frame covered with a fabric. The sealing portion can comprise an open cell foam or other material. A portion of the docking station can be permeable to blood and a portion of the docking station can be impermeable to blood. A portion of the docking station that is impermeable to blood can extend from at least the valve seat to at least the sealing portion. The docking station can be adjustable in length. The docking station can include a first half (i.e., portion) that a second half (i.e., portion) of the docking station can adjustably extend into to adjust the overall length. In other words, the length of the docking station can be adjusted by moving the second half/portion relative to the first half/portion, and the first half/portion may be moved independently from the second half/portion (e.g., one half/portion may remain in place while the other half/portion moves). If one of the first or second halves/portions extends inside the other half/portion and overlaps to adjust the length, the first half/portion and second half/portion may be adjusted to change the amount/length of overlap between the two. The one or more retaining portions can extend radially outward of the one or more sealing portion when the docking station is in an unconstrained state. Other features described elsewhere in this disclosure may also be included.

In one exemplary embodiment, a method can include expanding a docking station and expanding a valve in the docking station. The docking station can be expanded such that a valve seat of the docking station expands to a valve seat deployed size and a sealing portion expands to a sealing size that is within a range of sealing sizes. A frame of an expandable valve can be expanded to engage the valve seat of the docking station. A pressure of blood acting on the valve and docking station can enhance retention by the retaining portions at the deployed position. The valve seat of the docking station can be configured such that a diameter of the valve seat is not increased more than 2 mm (or not more than 1 mm, 3 mm, or 4 mm) by the radial outward force applied by the expandable frame to the valve seat. The range of sealing sizes of the docking station can be from 27 mm to 38 mm. The valve seat can be formed by a suture, ring, band, structural arrangement, material, foam, and in other ways. Other features/steps described elsewhere in this disclosure may also be included.

In one embodiment, for example, a docking station can include a valve seat, and one or more sealing portions. The valve seat can be expanded to a deployed size. The one or more sealing portions can be connected to the valve seat and extend radially outward of the valve seat. The one or more sealing portions can be constructed to expand outward of the valve seat and provide a seal over a range of sizes. A length of the docking station can be adjustable. The docking station can include a first half (i.e., portion) that a second half (i.e., portion) of the docking station can adjustably extend into to adjust the overall length. In other words, the length of the docking station can be adjusted by moving the second half/portion relative to the first half/portion, and the first half/portion may be moved independently from the second half/portion (e.g., one half/portion may remain in place while the other half/portion moves). If one of the first or second halves/portions extends inside the other half/portion and overlaps to adjust the length, the first half/portion and second half/portion may be adjusted to change the amount/length of overlap between the two.

The valve seat can be constructed such that the valve seat is not substantially expandable radially outwardly by a radially outward force of an expandable valve. A range of sizes of the sealing portion can be from 27 mm to 38 mm. The docking station can be configured to expand radially outwardly to varying degrees along its length L. The valve seat and the one or more sealing portions can act as an isolator that substantially prevents radial outward forces of an expandable valve from being transferred to the one or more sealing portions. The valve seat can be formed by a suture, ring, band, structural arrangement, material, foam, and in other ways. The sealing portion can comprise a portion of a metal frame covered with a fabric. The sealing portion can comprises an open cell foam. A portion of the docking station can be permeable to blood and a portion of the docking station can be impermeable to blood. Other features described elsewhere in this disclosure may also be included.

In one exemplary embodiment, a system can include an expandable docking station and an expandable valve. The expandable docking station can include a valve seat, and one or more sealing portions. The valve seat can expand to a deployed size. The one or more sealing portions can be connected to the valve seat and can extend radially outward of the valve seat. The one or more sealing portions can be constructed to expand outward of the valve seat and provide a seal over a range of sizes. A length of the docking station can be adjustable, e.g., adjustable in the same or similar ways to those discussed elsewhere herein. The expandable valve can comprise an expandable frame and a valve element. The expandable frame can expand to engage the valve seat of the docking station. The valve element can be connected to the expandable frame. A second half of the docking station may extend into a first half of the docking station to make the length of the docking station adjustable. The valve seat may be configured such that the valve seat is not substantially expanded radially outwardly by a radially outward force of the expandable valve. The docking station can be configured to expand radially outwardly to varying degrees along its length L. The valve seat can be formed by a suture, ring, band, structural arrangement, material, foam, and in other ways. The sealing portion can comprise a portion of a metal frame covered with a fabric. The sealing portion can comprise an open cell foam. A portion of the docking station can be permeable to blood and a portion of the docking station can be impermeable to blood. Other features described elsewhere in this disclosure may also be included.

In one exemplary embodiment, a method can include expanding a multiple piece docking station and expanding a valve in the docking station. A first docking station half or portion can be expanded. A portion/section of a second docking station half or portion can be positioned in the first docking station half, e.g., such that a desired length overlaps. The second docking station half can be expanded in the first docking station half to set a length of the docking station. The docking station can have valve seat and a sealing portion. A frame of an expandable valve can be expanded to engage the valve seat of the docking station. The valve seat can be configured such that the valve seat is not substantially expanded radially outwardly by a radially outward force of an expandable valve. A predetermined size of the sealing portion of the docking station can be from 27 mm to 38 mm. The valve seat can be formed by a suture, ring, band, structural arrangement, material, foam, and in other ways. Other features/steps described elsewhere in this disclosure may also be included.

In one exemplary embodiment, a delivery catheter can include and outer tube and an inner tube. The outer tube can have a distal opening. The inner tube can be disposed in the outer tube such that a gap is formed between the inner tube and the outer tube. The inner tube can have an opening at a proximal end and can have one or more side openings. The delivery catheter can be configured such that injecting flushing liquid into the proximal end of the inner tube flushes the flushing liquid through the inner tube with at least some of the flushing liquid exiting the inner tube through the one or more side openings to fill the gap and flush air out the distal opening of the outer tube. The inner tube can have a distal opening and the delivery catheter can be configured such that the filling of the inner tube with the flushing liquid at the proximal end flushes the air out of the distal opening of the inner tube. The inner tube can be filled with the flushing liquid at an opening for a guide wire at the proximal end of the inner tube. The delivery catheter can be configured such that the air in the inner tube can be flushed out through the distal opening of the inner tube and through an opening in a nosecone that can be connected to the inner tube. Other features described elsewhere in this disclosure may also be included.

In one exemplary embodiment, a method can flush air from a delivery catheter. The delivery catheter can include an outer tube having a distal opening, an inner tube that has a proximal opening at a proximal end of the inner tube and one or more side openings, and a gap formed in between the inner tube and the outer tube. Flushing liquid can be injected into the proximal end of the inner tube, such that the flushing liquid flows through the inner tube and at least some of the flushing liquid exits the inner tube through the one or more side openings to fill the gap and flush air out the distal opening of the outer tube. The inner tube can be filled with the flushing liquid through the proximal opening, and the proximal opening can also be used for passing a guide wire through the delivery catheter. The delivery catheter can be inserted into a blood vessel after the air has been flushed out. Other features/steps described elsewhere in this disclosure may also be included.

In one exemplary embodiment, a catheter and docking station a sleeve, a docking station retainer, and a docking station. The docking station retainer can be disposed in the sleeve. The docking station retainer can include one or more retainer recesses. The docking station can be disposed in the sleeve. The docking station can include one or more extensions releasably attached to the docking station retainer. Each extension of the one or more extensions can include a head disposed in at least one of the one or more retainer recesses. Each extension of the one or more docking extensions can be configured to contact the docking station retainer at only two points. The head can be triangular and two heads may be included. The one or more retainer recesses can be a rectangular recess in the docking station retainer. Sides of the head can extend away from one another at an angle of between 60 degrees and 120 degrees. The sleeve can engage the one or more extensions to retain the one or more heads in the retainer recess when the sleeve is positioned over the one or more extensions. The one or more extensions can spring radially outward relative to the docking station retainer when unconstrained by the sleeve to release the one or more extensions from the docking station retainer. The one or more extensions can be tilted in the one or more recesses. Other features described elsewhere in this disclosure may also be included.

In one exemplary embodiment, a method of using a docking station can include placing a head of a docking station extension in a recess of a docking station retainer such that the docking station extension contacts the docking station retainer at only two points. The docking station and the docking station retainer can be placed in a sleeve. The sleeve can engage the docking station extension to retain the head of the docking station extension in the recess. The head can be triangular. The recess can be a rectangular recess in the docking station retainer. Sides of the head can extend away from one another at an angle of between 60 degrees and 120 degrees. The retainer and the docking station can be removed from the sleeve such that the head of the docking station extension springs radially outward relative to the docking station retainer to release the docking station extension from the docking station retainer. The extension can be tilted in the recess. Other features/steps described elsewhere in this disclosure may also be included.

In one exemplary embodiment, an assembly for deploying a docking station includes a handle and a catheter. The handle can include a housing, a drive member, and a driven member. The drive member can be rotatably coupled to the housing. The driven member can be coupled to the drive member and the housing, such that rotation of the drive member moves the driven member linearly in the housing. The catheter can include and outer sleeve and an inner sleeve. The outer sleeve can be fixedly connected to the driven member. The inner sleeve can be disposed in the outer sleeve and can be fixedly connected to the housing. Rotation of the drive member can move the outer sleeve relative to the inner sleeve. The drive member can comprise a wheel having a gear portion. The drive member can comprise an internally threaded member. The driven member can comprise a gear rack. The driven member can comprise an externally threaded member. A ratchet mechanism can be moveable from an engaged position to a disengaged position, such that when the ratchet is in the engaged position the drive member is able to be rotated in only one direction. A luer port may be fixed to the inner sleeve. A luer port and the inner sleeve can be configured to accept a guide wire that extends through the inner shaft. Other features described elsewhere in this disclosure may also be included.

In one exemplary embodiment, a method of deploying a docking station can include rotating a drive member relative to a housing to linearly move a driven member in the housing. An inner sleeve can be fixed to the housing and an outer sleeve can be fixed to the driven member. Rotation of the drive member moves the outer sleeve relative to the inner sleeve. The drive member can linearly move the driven member by engagement of gear teeth. The drive member can linearly move the driven member by engagement of threads. The drive member can be configured for rotation in only one direction. The first and second sleeves can be moved over a guide wire.

Various features as described elsewhere in this disclosure may be included in the examples summarized here and various methods and steps for using the examples and features may be used, including as described elsewhere herein.

Further understanding of the nature and advantages of the disclosed inventions can be obtained from the following description and claims, particularly when considered in conjunction with the accompanying drawings in which like parts bear like reference numerals.

BRIEF DESCRIPTION OF THE DRAWINGS

To further clarify various aspects of embodiments of the present disclosure, a more particular description of the certain embodiments will be made by reference to various aspects of the appended drawings. It is appreciated that these drawings depict only typical embodiments of the present disclosure and are therefore not to be considered limiting of the scope of the disclosure. Moreover, while the figures may be drawn to scale for some embodiments, the figures are not necessarily drawn to scale for all embodiments. Embodiments of the present disclosure will be described and explained with additional specificity and detail through the use of the accompanying drawings.

FIG. 5A is a schematic illustration of a compressed docking station being positioned in a circulatory system;

FIG. 5B is a schematic illustration of the docking station of FIG. 5A expanded to set the position of the docking station in the circulatory system;

FIG. 5C is a schematic illustration of an expandable transcatheter heart valve being positioned in the docking station illustrated by FIG. 5B;

FIG. 5D is a schematic illustration of the transcatheter heart valve of FIG. 5C expanded to set the position of the heart valve in the docking station;

FIG. 5E illustrates the docking station and transcatheter heart valve deployed in an irregularly shaped portion of the circulatory system;

FIG. 5F illustrates the docking station and transcatheter heart valve deployed in a pulmonary artery;

FIG. 14A illustrates an exemplary embodiment of a docking station with a transcatheter heart valve disposed inside the docking station;

FIG. 14B illustrates an exemplary embodiment of a docking station with a transcatheter heart valve disposed inside the docking station;

FIG. 14C illustrates an exemplary embodiment of a docking station with a transcatheter heart valve disposed inside the docking station;

FIG. 14D illustrates an exemplary embodiment of a docking station with a transcatheter heart valve disposed inside the docking station;

FIG. 28 is a side view of an exemplary embodiment of a telescoping docking station;

FIG. 49A is a sectional view of an exemplary embodiment of a catheter;

FIG. 49B is a sectional view of an exemplary embodiment of a catheter with a docking station crimped and loaded in the catheter;

FIG. 54 is a side view of an exemplary embodiment of a nosecone of a catheter;

FIG. 55 is a sectional view of an exemplary embodiment of a distal portion of a catheter;

FIG. 62 is a view of an exemplary embodiment of a handle for a docking station catheter with a side cover removed;

FIG. 63 is an enlarged portion of FIG. 62 illustrating a flushing system of a catheter;

DETAILED DESCRIPTION

The following description refers to the accompanying drawings, which illustrate specific embodiments of the invention. Other embodiments having different structures and operation do not depart from the scope of the present invention. Exemplary embodiments of the present disclosure are directed to devices and methods for providing a docking station or landing zone for a transcatheter heart valve ("THV"), e.g., THV 29. In some exemplary embodiments, docking stations for THVs are illustrated as being used within the pulmonary artery, although the docking stations (e.g., docking station 10) may be used in other areas of the anatomy, heart, or vasculature, such as the superior vena cava or the inferior vena cava. The docking stations described herein can be configured to compensate for the deployed THV being smaller than the space (e.g., anatomy/vasculature/etc.) in which it is to be placed.

It should be noted that various embodiments of docking stations and systems for delivery and implant are disclosed herein, and any combination of these options may be made unless specifically excluded. For example, any of the docking stations devices disclosed, may be used with any type of valve, and/or any delivery system, even if a specific combination is not explicitly described. Likewise, the different constructions of docking stations and valves may be mixed and matched, such as by combining any docking station type/feature, valve type/feature, tissue cover, etc., even if not explicitly disclosed. In short, individual components of the disclosed systems may be combined unless mutually exclusive or otherwise physically impossible.

For the sake of uniformity, in these Figures and others in the application the docking stations are depicted such that the pulmonary bifurcation end is up, while the ventricular end is down. These directions may also be referred to as "distal" as a synonym for up or the pulmonary bifurcation end, and "proximal" as a synonym for down or the ventricular end, which are terms relative to the physician's perspective.

Figure 1A:
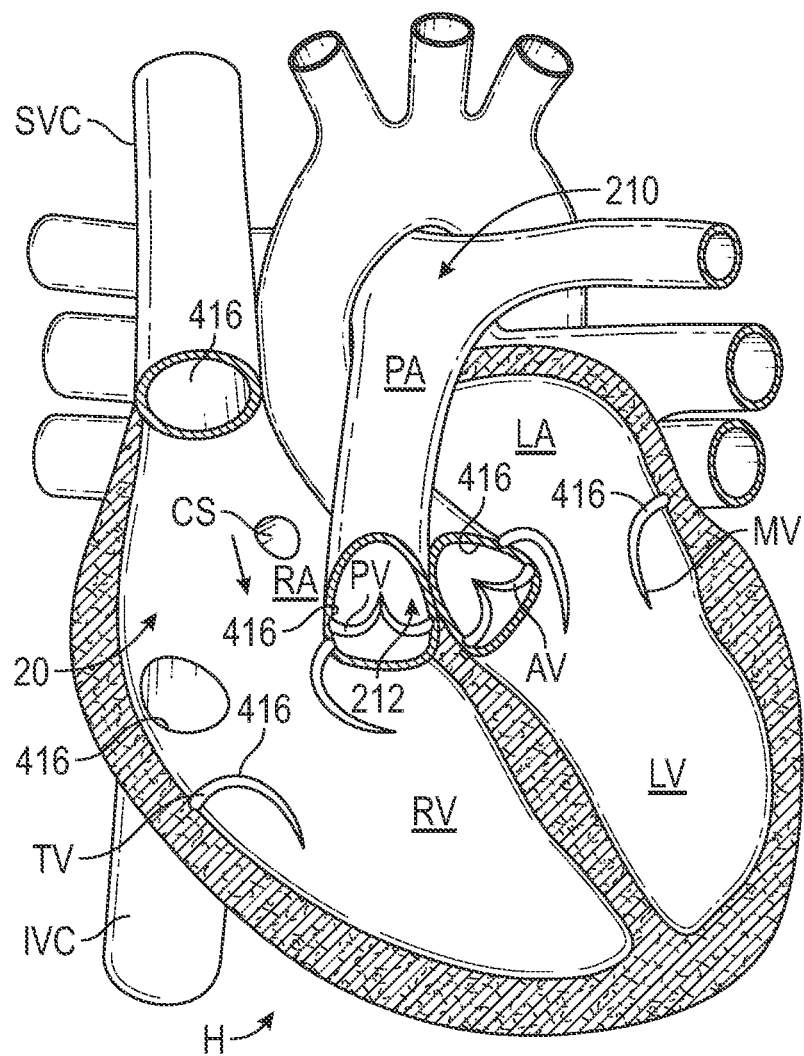
FIG. 1A is a cutaway view of the human heart in a diastolic phase.
Figure 1B:
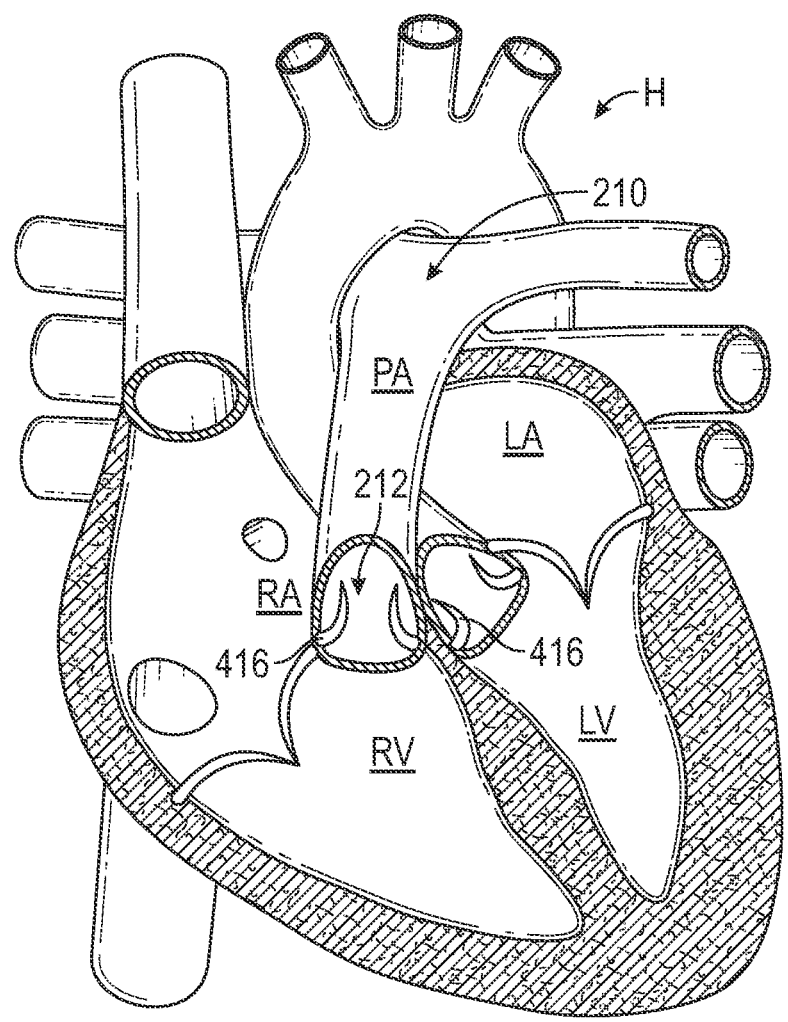
FIG. 1B is a cutaway view of the human heart in a systolic phase.
Figure 2A:
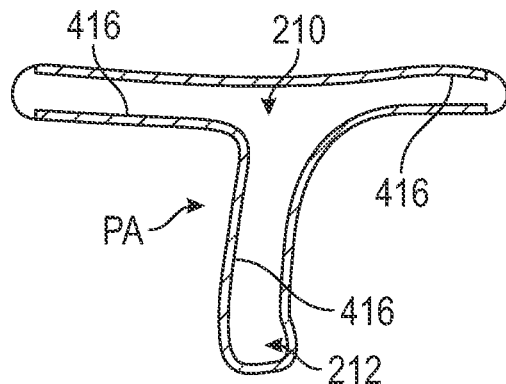
FIGS. 2A-2E are sectional views of pulmonary arteries illustrating that pulmonary arteries may have a variety of different shapes and sizes.
Figure 2B:
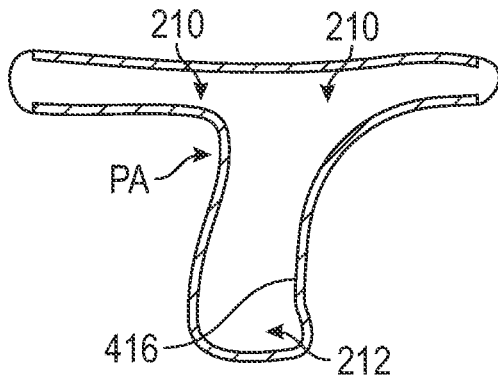
Figure 2C:
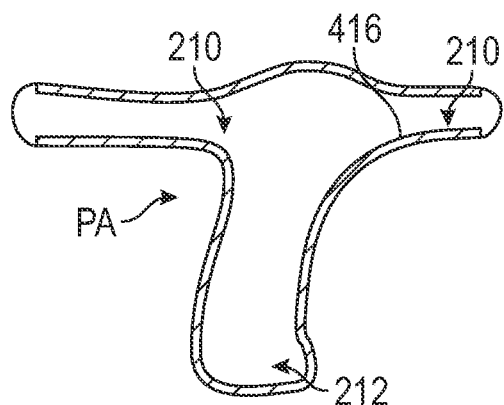
Figure 2D:
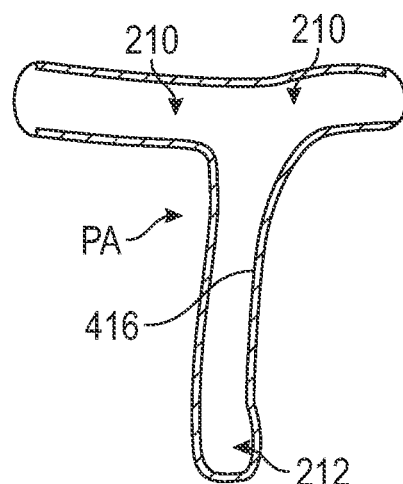
Figure 2E:
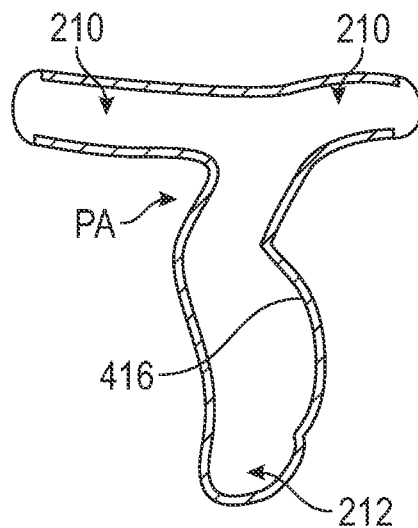
Figure 3A:
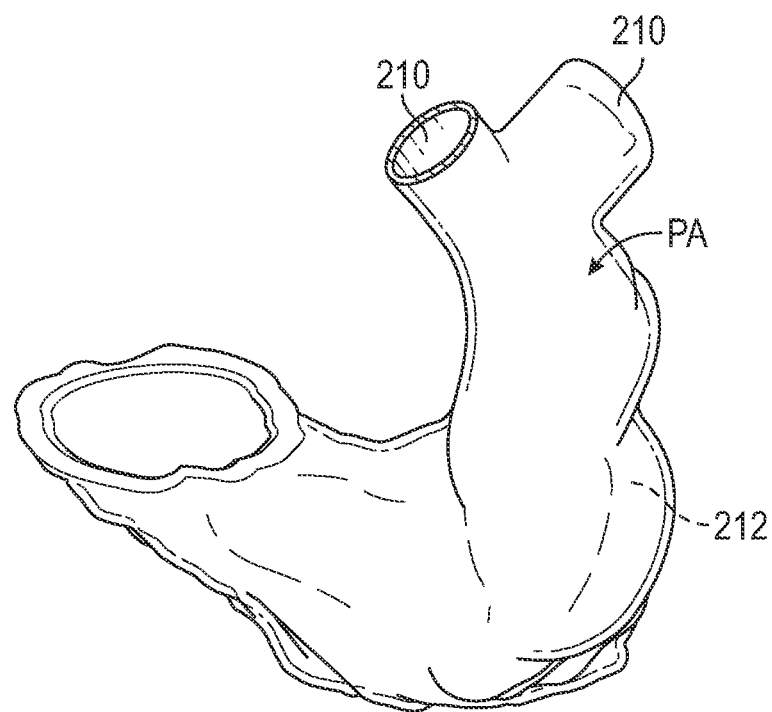
FIGS. 3A-3D are perspective views of pulmonary arteries illustrating that pulmonary arteries may have a variety of different shapes and sizes.
Figure 3B:
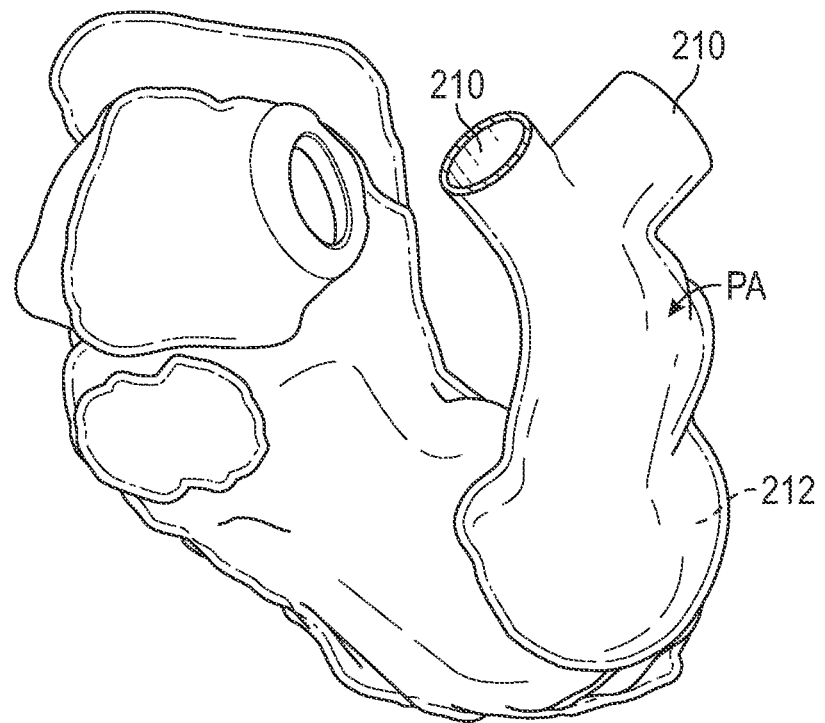
Figure 3C:
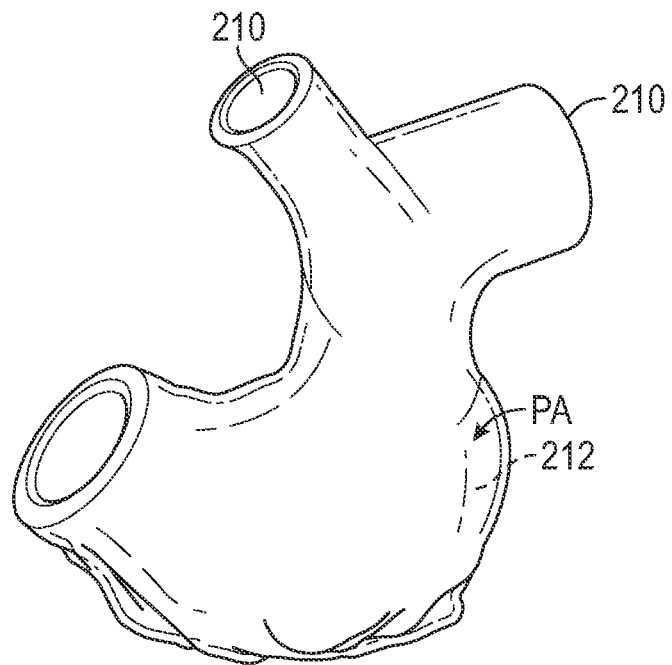
Figure 3D:
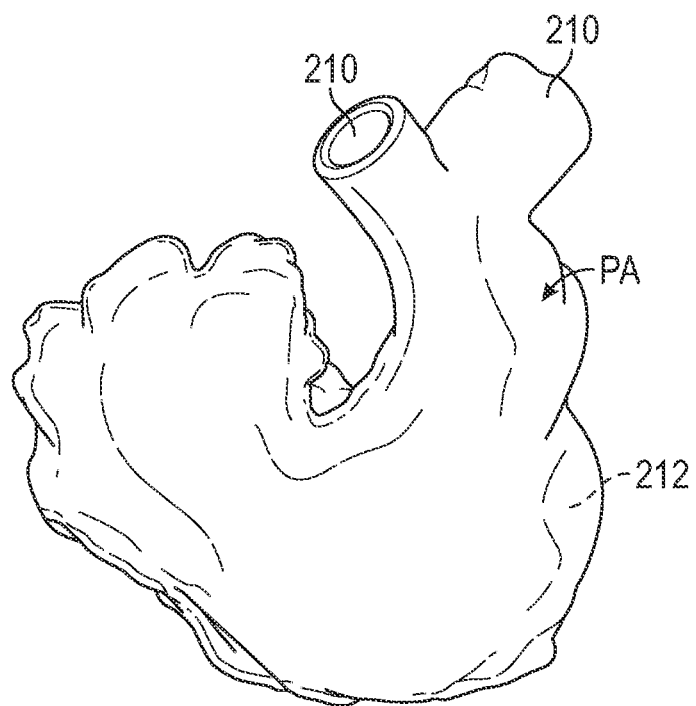

FIGS. 1A and 1B are cutaway views of the human heart H in diastolic and systolic phases, respectively. The right ventricle RV and left ventricle LV are separated from the right atrium RA and left atrium LA, respectively, by the tricuspid valve TV and mitral valve MV; i.e., the atrioventricular valves. Additionally, the aortic valve AV separates the left ventricle LV from the ascending aorta (not identified) and the pulmonary valve PV separates the right ventricle from the pulmonary artery PA. Each of these valves has flexible leaflets extending inward across the respective orifices that come together or "coapt" in the flowstream to form the one-way, fluid-occluding surfaces. The docking stations and valves of the present application are described primarily with respect to the pulmonary valve. Therefore, anatomical structures of the right atrium RA and right ventricle RV will be explained in greater detail. It should be understood that the devices described herein may also be used in other areas, e.g., in the inferior vena cava and/or the superior vena cava as treatment for a regurgitant or otherwise defective tricuspid valve, in the aorta (e.g., an enlarged aorta) as treatment for a defective aortic valve, in other areas of the heart or vasculature, in grafts, etc.

The right atrium RA receives deoxygenated blood from the venous system through the superior vena cava SVC and the inferior vena cava IVC, the former entering the right atrium from above, and the latter from below. The coronary sinus CS is a collection of veins joined together to form a large vessel that collects deoxygenated blood from the heart muscle (myocardium), and delivers it to the right atrium RA. During the diastolic phase, or diastole, seen in FIG. 1A, the venous blood that collects in the right atrium RA enters the tricuspid valve TV by expansion of the right ventricle RV. In the systolic phase, or systole, seen in FIG. 1B, the right ventricle RV contracts to force the venous blood through the pulmonary valve PV and pulmonary artery into the lungs. In one exemplary embodiment, the devices described by the present application are used to replace or supplement the function of a defective pulmonary valve. During systole, the leaflets of the tricuspid valve TV close to prevent the venous blood from regurgitating back into the right atrium RA.

Referring to FIGS. 2A-2E and 3A-3D, the shown, non-exhaustive examples illustrate that the pulmonary artery can have a wide variety of different shapes and sizes. For example, as shown in the sectional views of FIGS. 2A-2E and the perspective views of FIGS. 3A-3D, the length L, diameter, D, and curvature or contour may vary greatly between pulmonary arteries of different patients. Further, the diameter D may vary significantly along the length L of an individual pulmonary artery. These differences can be even more significant in pulmonary arteries that suffer from certain conditions and/or have been compromised by previous surgery. For example, the treatment of Tetralogy of Fallot (TOF) or Transposition of the Great Arteries (TGA) often results in larger and more irregularly shaped pulmonary arteries.

Tetralogy of Fallot (TOF) is a cardiac anomaly that refers to a combination of four related heart defects that commonly occur together. The four defects are ventricular septal defect (VSD), overriding aorta (the aortic valve is enlarged and appears to arise from both the left and right ventricles instead of the left ventricle as in normal hearts), pulmonary stenosis (narrowing of the pulmonary valve and outflow tract or area below the valve that creates an obstruction of blood flow from the right ventricle to the pulmonary artery), and right ventricular hypertrophy (thickening of the muscular walls of the right ventricle, which occurs because the right ventricle is pumping at high pressure).

Transposition of the Great Arteries (TGA) refers to an anomaly where the aorta and the pulmonary artery are "transposed" from their normal position so that the aorta arises from the right ventricle and the pulmonary artery from the left ventricle.

Surgical treatment for some conditions involves a longitudinal incision along the pulmonary artery, up to and along one of the pulmonary branches. This incision can eliminate or significantly impair the function of the pulmonary valve. A trans-annular patch is used to cover the incision after the surgery. The trans-annular patch reduces stenotic or constrained conditions of the pulmonary artery PA, associated with other surgeries. However, the impairment or elimination of the pulmonary valve PV can create significant regurgitation and, prior to the present invention, often required later open heart surgery to replace the pulmonary valve. The trans-annular patch technique can result in pulmonary arteries having a wide degree of variation in size and shape (See FIGS. 3A-3D)

Referring to FIGS. 4A-4F, in one exemplary embodiment an expandable docking station 10 includes one or more sealing portions 410, a valve seat 18, and one or more retaining portions 414. The sealing portion(s) 410 provide a seal between the docking station 10 and an interior surface 416 of the circulatory system. The valve seat 18 provides a supporting surface for implanting or deploying a valve 29 in the docking station 10 after the docking station 10 is implanted in the circulatory system. The retaining portions 414 help retain the docking station 10 and the valve 29 at the implantation position or deployment site in the circulatory system. Expandable docking station 10 and valve 29 as described in the various embodiments herein are also representative of a variety of docking stations and/or valves that might be known or developed, e.g., a variety of different types of valves could be substituted for and/or used as valve 29 in the various docking stations.

Figure 4A:
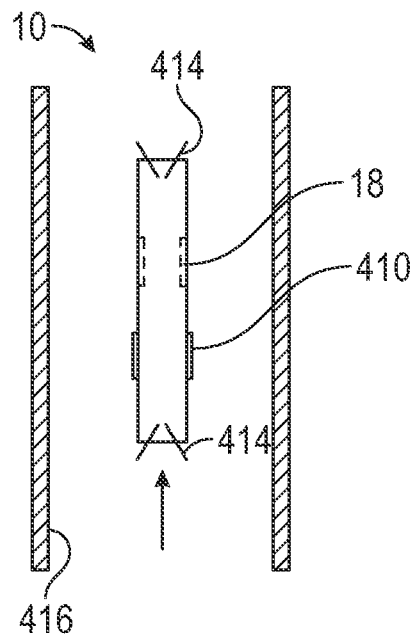
FIG. 4A is a schematic illustration of a compressed docking station being positioned in a circulatory system.
Figure 4B:
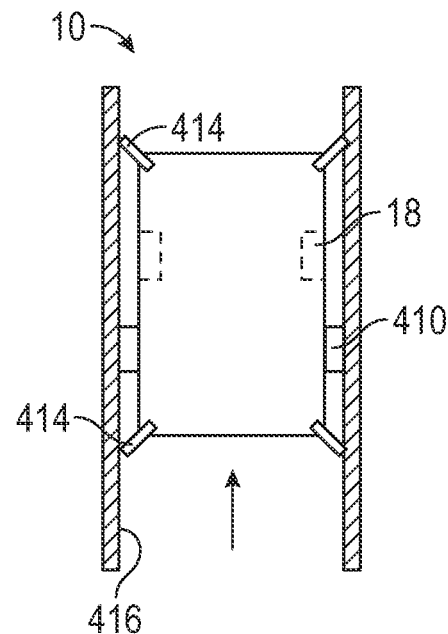
FIG. 4B is a schematic illustration of the docking station of FIG. 4A expanded to set the position of the docking station in the circulatory system.
Figure 4C:
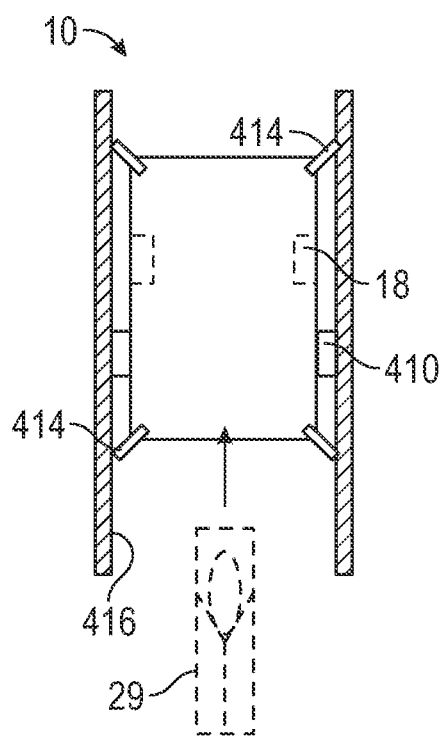
FIG. 4C is a schematic illustration of an expandable transcatheter heart valve being positioned in the docking station illustrated by FIG. 4B.
Figure 4D:
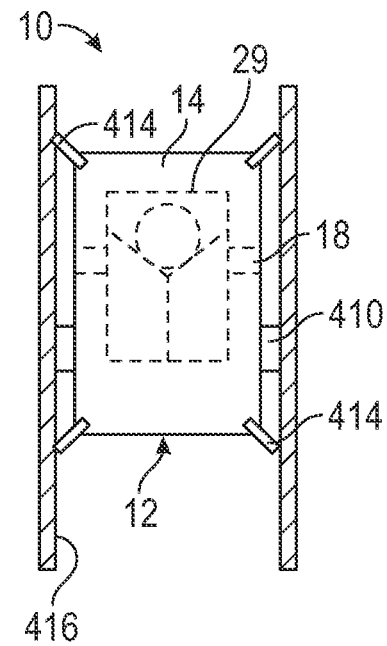
FIG. 4D is a schematic illustration of the transcatheter heart valve of FIG. 4C expanded to set the position of the heart valve in the docking station.

FIGS. 4A-4D schematically illustrate an exemplary deployment of the docking station 10 and valve 29 in the circulatory system. Referring to FIG. 4A, the docking station 10 is in a compressed form/configuration and is introduced to a deployment site in the circulatory system. For example, the docking station 10, may be positioned at a deployment site in a pulmonary artery by a catheter (e.g., catheter 3600 as shown in FIGS. 50A-50D). Referring to FIG. 4B, the docking station 10 is expanded in the circulatory system such that the sealing portion(s) 410 and the retaining portions 414 engage the inside surface 416 of a portion of the circulatory system. Referring to FIG. 4C, after the docking station 10 is deployed, the valve 29 is in a compressed form and is introduced into the valve seat 18 of the docking station 10. Referring to FIG. 4D, the valve 29 is expanded in the docking station, such that the valve 29 engages the valve seat 18. In the examples depicted herein, the docking station 10 is longer than the valve. However, in other embodiments the docking station 10 can be the same length or shorter than the length of the valve 29. Similarly, the valve seat 18 can be longer, shorter, or the same length as the length of the valve 29.

Referring to FIG. 4D, the valve 29 has expanded such that the seat 18 of the docking station supports the valve. The valve 29 only needs to expand against the narrow seat 18, rather than against the wider space within the portion of the circulatory system that the docking station 10 occupies. The docking station 10 allows the valve 29 to operate within the expansion diameter range for which it is designed.

Figure 4E:
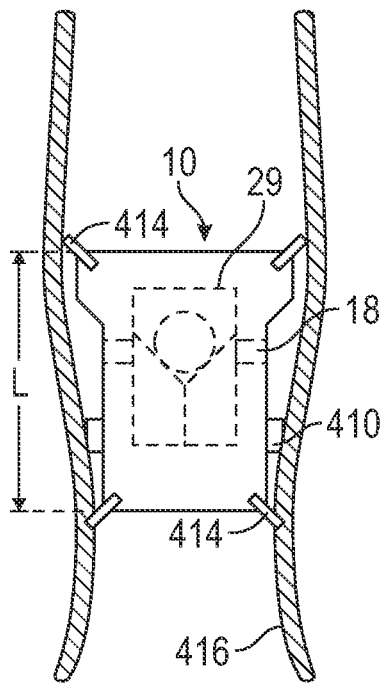
FIG. 4E illustrates the docking station and transcatheter heart valve deployed in an irregularly shaped portion of the circulatory system.

FIG. 4E illustrates that the inner surface 416 of the circulatory system, such as the inner surface of a blood vessel or anatomy of the heart can vary in cross-section size and/or shape along its length. In an exemplary embodiment, the docking station 10 is configured to expand radially outwardly to varying degrees along its length L to conform to shape of the inner surface 416. In one exemplary embodiment, the docking station 10 is configured such that the sealing portion(s) 410 and/or the retaining portion(s) engage the inner surface 416, even though the shape of the blood vessel or anatomy of the heart vary significantly along the length L of the docking station. The docking station can be made from a very resilient or compliant material to accommodate large variations in the anatomy. For example, the docking station can be made from a highly flexible metal, metal alloy, polymer, or an open cell foam. Examples of a metals and metal alloys that can be used include, but are not limited to, nitinol, elgiloy, and stainless steel, but other metals and highly resilient or compliant non-metal materials can be used. For example, the docking station 10 can have a frame or portion of a frame (e.g., a self-expanding frame, retaining portion(s), sealing portion(s), valve seat, etc.) made of these materials, e.g., from shape memory materials, such as nitinol. These materials allow the frame to be compressed to a small size, and then when the compression force is released, the frame will self-expand back to its pre-compressed diameter.

An example of an open cell foam that can be used to form the docking station or a portion of the docking station is a bio-compatible foam, such as a polyurethane foam (e.g., as may be obtained from Biomerix, Rockville, Md.). Docking stations described herein can be self-expanding and/or expandable with an inflatable device to cause the docking station to engage an inner surface 416 having a variable shape.

Figure 4F:
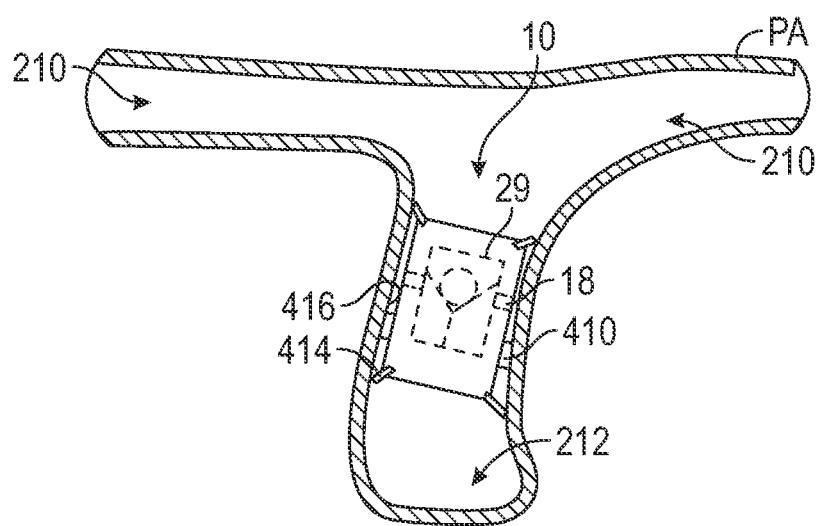
FIG. 4F illustrates the docking station and transcatheter heart valve deployed in a pulmonary artery.

FIG. 4F illustrates the docking station 10 and a valve 29 implanted in a pulmonary artery PA. As mentioned with respect to FIGS. 2A-2E and 3A-3D, the shape of the pulmonary artery may vary significantly along its length. In one exemplary embodiment, the docking station 10 is configured to conform to the varying shape of the pulmonary artery PA in the same manner as described with respect to FIG. 4E.

Referring to FIGS. 5A-5F, in one exemplary embodiment an expandable docking station 10 is made from an expandable foam material, such as an open cell biocompatible foam. The outer surface 510 of the foam material can serve as the sealing portion 410. In this example, a valve seat 18 can be provided on the inner surface 512 of the foam material as illustrated, or the inner surface 512 can serve as the valve seat. In the example illustrated by FIGS. 5A-5F, the retaining portions 414 are omitted, though retaining portions can be used. In one embodiment, foam material can be used together with an expandable frame (e.g., of metal, shape memory material, etc.). The foam material can cover or extend the full length of the frame or only a portion of the length of the frame.

FIGS. 5A-5D schematically illustrate deployment of the foam docking station 10 and valve 29 in the circulatory system. Referring to FIG. 5A, the docking station 10 is in a compressed form and is introduced to a deployment site in the circulatory system. For example, the docking station 10, may be positioned at a deployment site in a pulmonary artery by a catheter (e.g., catheter 3600 shown in FIGS. 50A-50D).

Referring to FIG. 5B, the docking station 10 is expanded in the circulatory system such that the sealing portion 410 engage the inside surface 416 of the circulatory system. Referring to FIG. 5C, after the docking station 10 is deployed, the valve 29 is in a compressed form and is introduced into the valve seat 18 or inner surface 512 of the docking station 10. Referring to FIG. 5D, the valve 29 is expanded in the docking station, such that the valve 29 engages the valve seat 18 or inner surface 512 (e.g., where inner surface 512 acts as the valve seat).

FIG. 5E illustrates that the inner surface 416 of the circulatory system, such as the inner surface of a blood vessel or anatomy of the heart may vary in cross-section along its length. In an exemplary embodiment, the foam docking station 10 is configured to expand radially outwardly to varying degrees along its length L to conform to shape of the inner surface 416.

FIG. 5F illustrates the foam docking station 10 and a valve 29 implanted in a pulmonary artery PA. As mentioned with respect to FIGS. 2A-2E and 3A-3D, the shape of the pulmonary artery may vary significantly along its length. In one exemplary embodiment, the docking station 10 is configured to conform to the varying shape of the pulmonary artery PA in the same or a similar manner as described with respect to FIG. 4E.

Figure 6A:
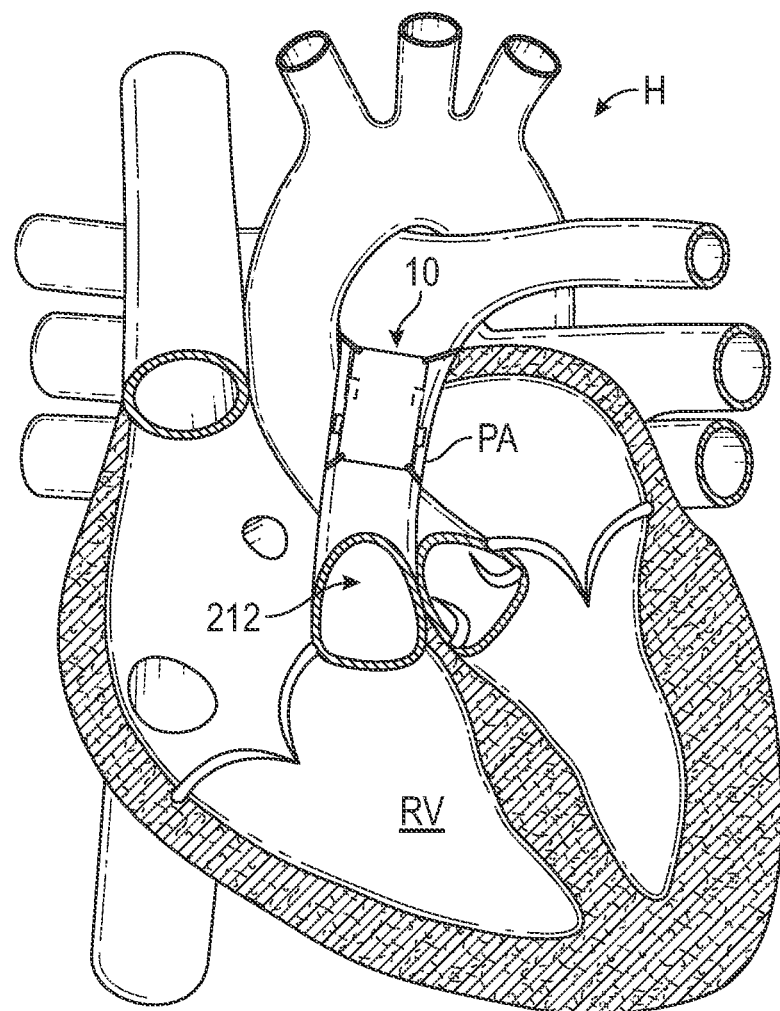
FIG. 6A is a cutaway view of the human heart in a systolic phase with a docking station and deployed in a pulmonary artery.
Figure 6B:
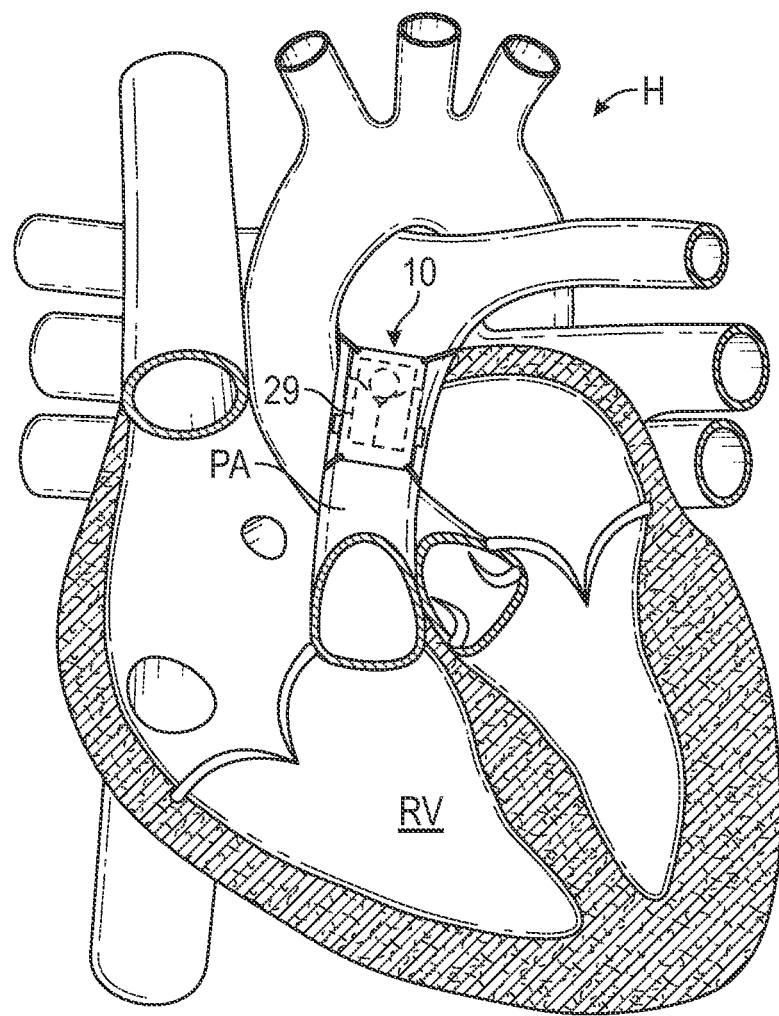
FIG. 6B is a cutaway view of the human heart in a systolic phase with a docking station and transcatheter heart valve deployed in a pulmonary artery.
Figure 7A:
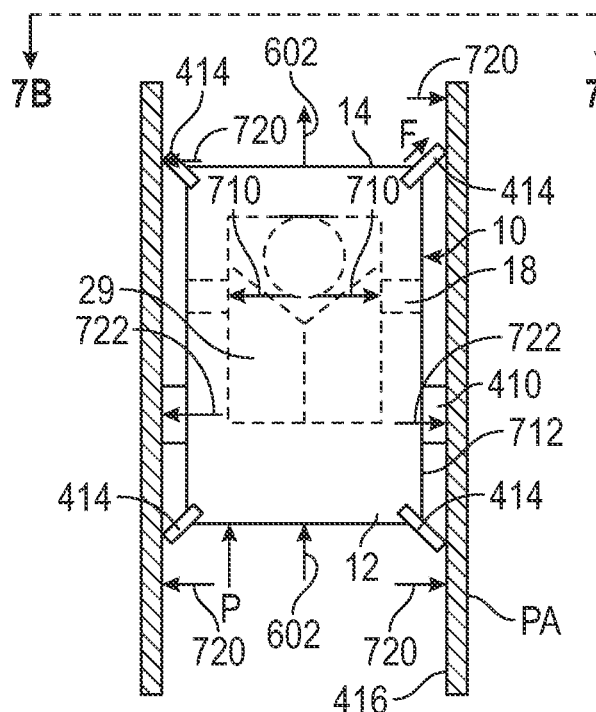
FIG. 7A is an enlarged schematic illustration of the docking station and transcatheter heart valve of FIG. 6B when the heart is in the systolic phase.
Figure 7B:
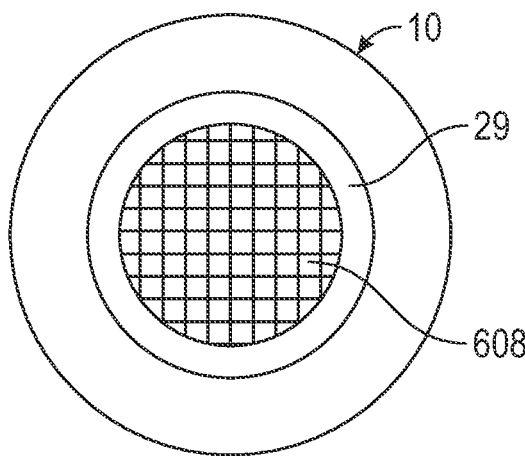
FIG. 7B is a view taken in the direction indicated by lines 7B-7B in FIG. 7A.

Referring to FIG. 6A, a docking station, e.g., a docking station as described with respect to FIGS. 4A-4D, is deployed in the pulmonary artery PA of a heart H. FIG. 6B illustrates a valve 29 deployed in the docking station 10 illustrated by FIG. 6A. In FIGS. 6A and 6B, the heart is in the systolic phase. FIG. 7A is an enlarged representation of the docking station 10 and valve 29 in the pulmonary artery 29 of FIG. 6B. When the heart is in the systolic phase, the valve 29 opens. Blood flows from the right ventricle RV and through the pulmonary artery PA, docking station 10, and valve 29 as indicated by arrows 602. FIG. 7B illustrates space 608 that represents the valve 29 being open when the heart is in the systolic phase. FIG. 7B does not show the interface between the docking station 10 and the pulmonary artery to simplify the drawing. The cross-hatching in FIG. 7B illustrates blood flow through the open valve. In an exemplary embodiment, blood is prevented from flowing between the pulmonary artery PA and the docking station 10 by the sealing portion(s) 410 and blood is prevented from flowing between the docking station 10 and the valve 29 by seating of the valve 29 in the seat 18 of the docking station 10. In this example, blood is substantially only flowing or only able to flow through the valve 29 when the heart is in the systolic phase.

Figure 8:
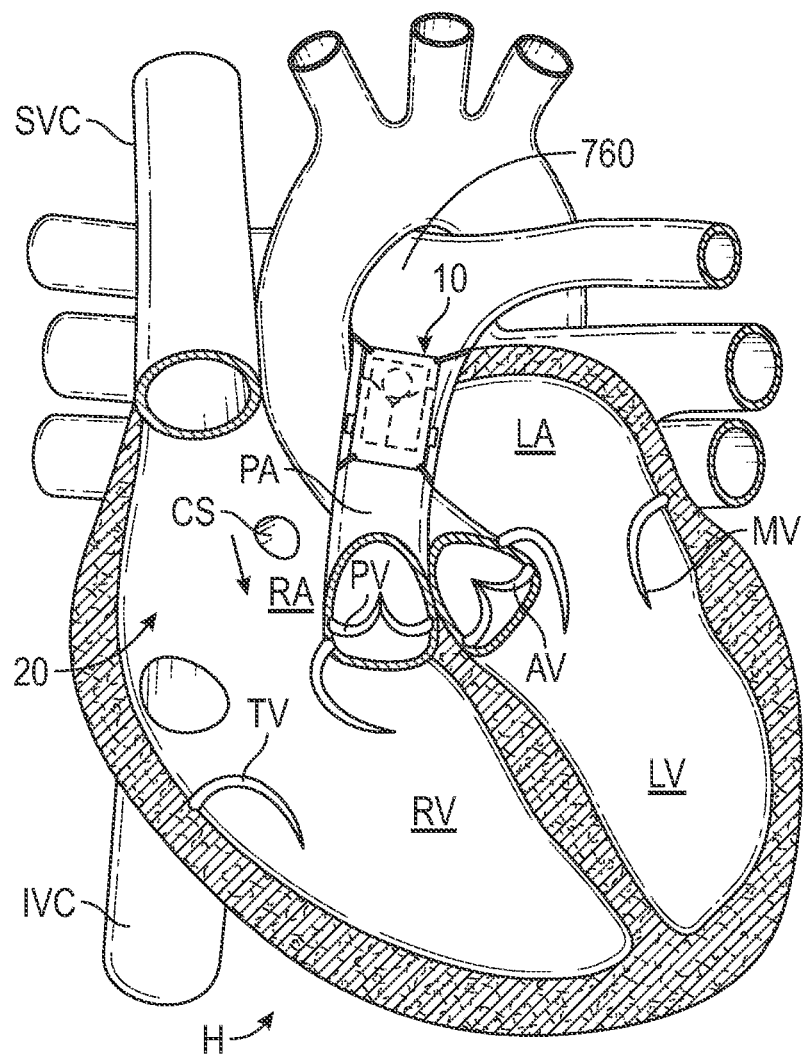
FIG. 8 is a cutaway view of the human heart in a diastolic phase with a docking station and transcatheter heart valve deployed in a pulmonary artery.
Figure 9A:
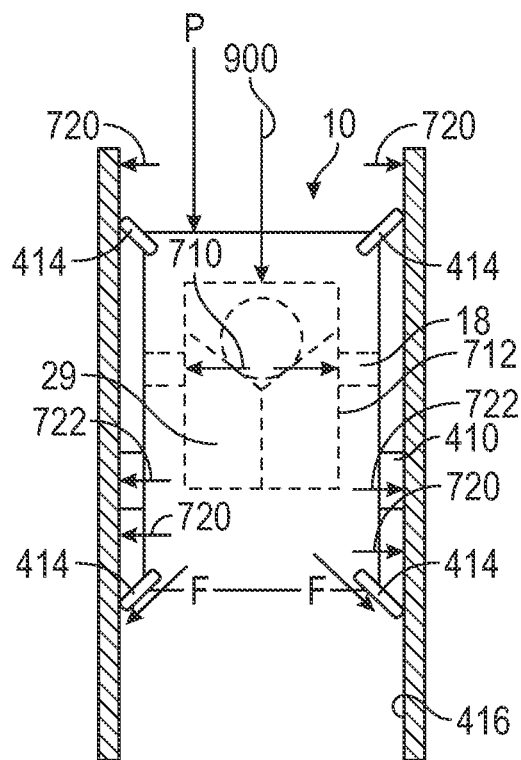
FIG. 9A is an enlarged schematic illustration of the docking station and transcatheter heart valve of FIG. 8 when the heart is in the diastolic phase.
Figure 9B:
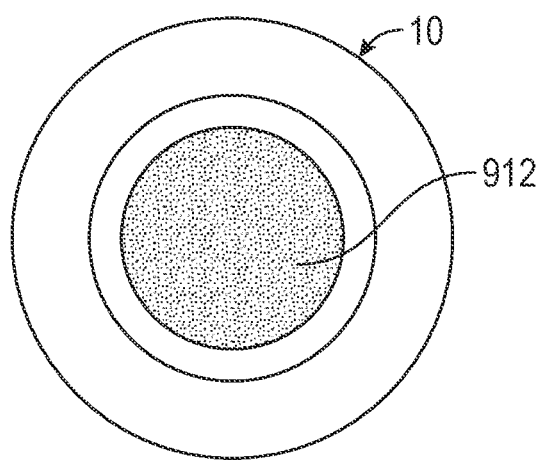
FIG. 9B is a view taken in the direction indicated by lines 9B-9B in FIG. 9A.

FIG. 8 illustrates the valve 29, docking station 10 and heart H illustrated by FIG. 6B, when the heart is in the diastolic phase. Referring to FIGS. 9A and 9B, when the heart is in the diastolic phase, the valve 29 closes. FIG. 9A is an enlarged representation of the docking station 10 and valve 29 in the pulmonary artery 29 of FIG. 8. Blood flow in the pulmonary artery PA above the valve 29 (i.e. in the pulmonary branch 760) is blocked by the valve 29 being closed and blocking blood flow as indicated by arrow 900. The solid area 912 in FIG. 9B represents the valve 29 being closed when the heart is in the diastolic phase.

In one exemplary embodiment, the docking station 10 acts as an isolator that prevents or substantially prevents radial outward forces of the valve 29 from being transferred to the inner surface 416 of the circulatory system. In one embodiment, the docking station 10 includes a valve seat 18 (which is not expanded radially outwardly or is not substantially expanded radially outward by the radially outward force of the THV or valve 29, i.e., the diameter of the valve seat is not increased or is increased by less than 4 mm by the force of the THV), and anchoring/retaining portions 414 and sealing portions 410, which impart only relatively small radially outward forces 720, 722 on the inner surface 416 of the circulatory system (as compared to the radially outward force applied to the valve seat 18 by the valve 29).

When no docking station is used, stents and frames of THVs are held in place in the circulatory system by a relatively high radial outward force 710 of the stent or frame 712 of the THV acting directly on the inside surface 416 of the circulatory system. If a docking station is used, as in the example illustrated by FIG. 7A, the stent or frame 712 of the valve 29 expands radially outward or is expanded radially outward to impart the high force 710 on the valve seat 18 of the docking station 10. This high radially outward force 710 secures the valve 29 to the valve seat 18 of the docking station 10. However, since the valve seat 18 is not expanded or is not substantially expanded by the force 710, the force 710 is isolated from the circulatory system, rather than being used to secure the docking station in the circulatory system.

In an exemplary embodiment, the radially outward force 722 of the sealing portions 410 to the inside surface 416 is substantially smaller than the radially outward force 710 applied by the valve 29 to the valve seat 18. For example, the radially outward sealing force 722 can be less than ½ the radially outward force 710 applied by the valve, less than ⅓ the radially outward force 710 applied by the valve, less than ¼ the radially outward force 710 applied by the valve, less than ⅛, or even less than ¹/₁₀ the radially outward force 710 applied by the valve. In one exemplary embodiment, the radially outward force 722 of the sealing portions 410 is selected to provide a seal between the inner surface 416 and the sealing portion 410, but is not sufficient by itself to retain the position of the valve 29 and docking station 10 in the circulatory system.

In an exemplary embodiment, the radially outward force 720 of the anchoring/retaining portions 414 to the inside surface 416 is substantially smaller than the radially outward force 710 applied by the valve 29 to the valve seat 18. For example, the radially outward sealing force 720 can be less than ½ the radially outward force 710 applied by the valve, less than ⅓ the radially outward force 710 applied by the valve, less than ¼ the radially outward force 710 applied by the valve, less than ⅛, or even less than ¹/₁₀ the radially outward force 710 applied by the valve.

In one exemplary embodiment, the radially outward force 720 of the retaining portions 414 is not sufficient by itself to retain the position of the valve 29 and docking station 10 in the circulatory system. Rather, the pressure of the blood 608 is used to enhance the retention of the retaining portions 414 to the inside surface 416. Referring again to FIG. 6A, when the heart is in the systolic phase, the valve 29 is open and blood flows through the valve as indicated by arrows 602. Since the valve 29 is open and blood flows through the valve 29, the pressure P applied to the docking station 10 and valve 29 by the blood is low as indicated by the small P and arrow in FIG. 7A. Even though small, the pressure P forces the docking station and its upper retaining portions 414 against the surface 416 generally in the direction indicated by arrow F. This blood flow assisted force F applied by the retaining portions F to the surface 416 prevents the docking station 10 and valve 29 from moving in the direction 602 of blood flow in the systolic phase of the heart H.

Referring to FIG. 9A, when the heart is in the diastolic phase, the valve 29 is closed and blood flow is blocked as indicated by arrow 900. Since the valve 29 is closed and the valve 29 and docking station 10 block the flow of blood, the pressure P applied to the docking station 10 and valve 29 by the blood is high as indicated by the large arrow P in FIG. 9A. This large pressure P forces the lower retaining portions 414 against the surface 416 generally in the direction indicated by the large arrows F. This blood flow assisted force F applied by the retaining portions F to the surface 416 prevents the docking station 10 and valve 29 from moving in the direction indicated by arrow 900.

Since the force applied by the upper and lower retaining portions 414 is determined by amount of pressure applied to the valve 29 and docking station 10 by the blood, the force applied to the surface 416 is automatically proportioned. That is, the upper retaining portions are less forcefully pressed against the surface 416 when the heart is in the systolic phase than the lower retaining portions are pressed against the surface 416 when the heart is in the diastolic phase. This is because the pressure against the open valve 29 and docking station 10 in the systolic phase is less than the pressure against the closed valve and docking station in the diastolic phase.

The valve seat 18 and sealing portion 410 can take a wide variety of different forms. For example, the valve seat 18 can be any structure that is not expanded radially outwardly or is not substantially expanded radially outward by the radially outward force of the THV (i.e., the diameter of the valve seat in the deployed position/configuration may not expand or may expand less than 4 mm, e.g., the diameter may only expand 1-4 mm larger when the valve is deployed in the valve seat). For example, the valve seat 18 can comprise a suture or a metal ring that resists or limits expansion. However, in one embodiment, the valve seat 18 (or any valve seat described herein) can be expandable over a larger range, for example, the diameter may expand between 5 mm and 30 mm larger when a valve is deployed in the valve seat. In one embodiment, the diameter might expand from 5 mm or 6 mm in diameter to 20 mm-29 mm, 24 mm, 26 mm, 29 mm, etc. in diameter, or expand from and to different diameters within that range. Even if more expandable, the valve seat can still be restricted in expansion, e.g., restricted to avoid expansion of the valve seat beyond an expanded diameter of a valve to be placed in the valve seat or to avoid expansion beyond a diameter that will securely hold the valve in the valve seat via the forces created therebetween. The valve seat 18 can be part of or define a portion of the body of the docking station 10, or the valve seat 18 can be a separate component that is attached to the body of the docking station. The valve seat 18 can be longer, shorter, or the same length as the valve. The valve seat 18 can be significantly shorter than the valve 29 when the valve seat 18 is defined by a suture or a metal ring. A valve seat 18 formed by a suture or metal ring can form a narrow circumferential seal line between the valve 29 and the docking station.

The sealing portion(s) 410 of various embodiments can take a wide variety of different forms. For example, the sealing portion(s) 410 can be any structure that provides a seal(s) between the docking station 10 and the surface 416 of the circulatory system. For example, the sealing portion (s) 410 can comprise a fabric, a foam, biocompatible tissue, a combination of these, etc. The sealing portion(s) 410 can be part of or define a portion of the body of the docking station 10, and/or the sealing portion(s) 410 can be a separate component that is attached to the body of the docking station. The docking station 10 may include a single sealing portion 410 or two, or more than two sealing portions.

Figure 7C:
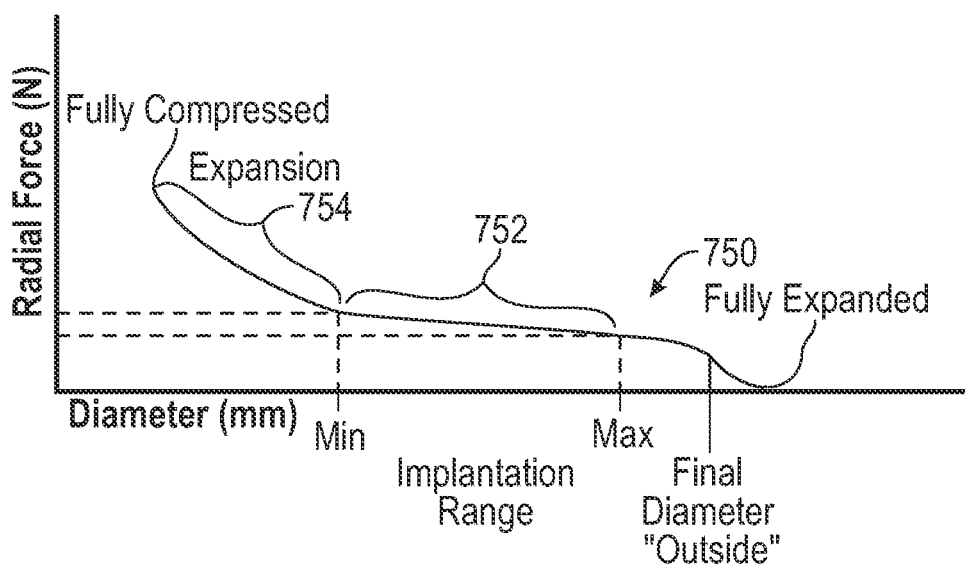
FIG. 7C is a graph showing a relationship between a docking station diameter and a radial outward force applied by the docking station.

As mentioned above, in one exemplary embodiment the sealing portion(s) 410 is configured to apply a low radially outward force to the surface 416. The low radially outward force can be provided in a wide variety of different ways. For example, sealing portion may be made from a very compressible or compliant material. Referring to FIG. 7C, in one exemplary embodiment, the docking station 10 body is made from an elastic or superelastic metal. One such metal is nitinol. When the body of a docking station 10 is made from a lattice of metal struts, the body can have the characteristics of a spring. Referring to FIG. 7C, like a spring, when the body of the docking station is unconstrained and allowed to relax to its largest diameter the body of the docking station applies little or no radially outward force. As the body of the docking station 10 is compressed, like a spring, the radially outward force applied by the docking station increases. As is illustrated by FIG. 7C, in one exemplary embodiment the relationship of the radially outward force of the docking station body to the expanded diameter of the docking station is non-linear, although, in one exemplary embodiment, the relationship could also be linear. In the example illustrated by FIG. 7C, the curve 750 illustrates the relationship between the radially outward force exerted by the docking station 10 and the compressed diameter of the docking station. In the region 752, the curve 750 has a low slope. In this region 752 the radially outward force is low and changes only a small amount. In one exemplary embodiment, the region 752 corresponds to a diameter between 25 mm and 40 mm, such as between 27 mm and 38 mm. The radially outward force is small in the region 752, but is not zero. In the region 754, the curve 750 has a higher slope. In this region 754 the radially outward force increases significantly as the docking station is compressed. In one exemplary embodiment, the body of the stent is constructed to be in the low slope region 752. This allows the sealing portions 710 to apply only a small radially outward force to the inner surface 416 of the circulatory system over a wide range of diameters.

The retaining portions 414 can take a wide variety of different forms. For example, the retaining portion(s) 414 may be any structure that sets the position of the docking station 10 in the circulatory system. For example, the retaining portion(s) 414 may press against or into the inside surface 416 or extend around anatomical structure of the circulatory system to set the position of the docking station 10. The retaining portion(s) 414 may be part of or define a portion of the body of the docking station 10 or the retaining portion(s) 414 may be a separate component that is attached to the body of the docking station. The docking station 10 may include a single retaining portion 414 or two, or more than two retaining portions.

Figure 10A:
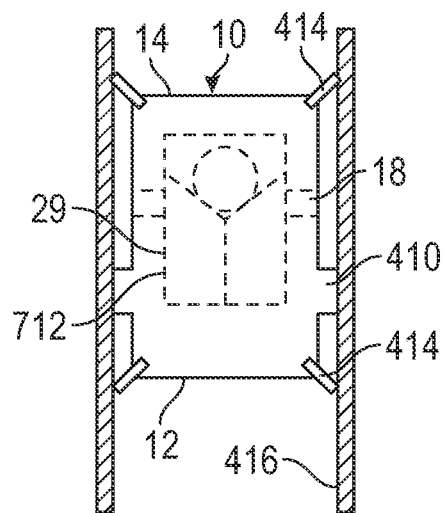
FIG. 10A illustrates an exemplary embodiment of a docking station with a transcatheter heart valve disposed inside the docking station.
Figure 10B:
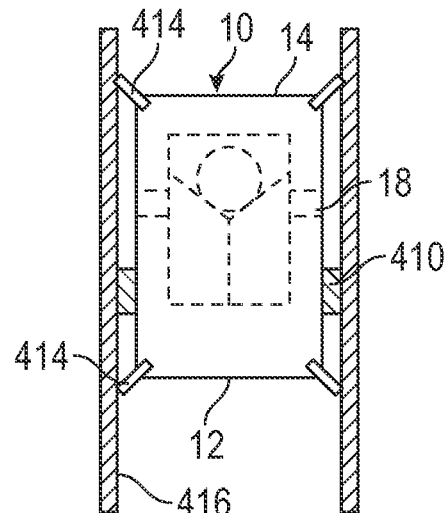
FIG. 10B illustrates an exemplary embodiment of a docking station with a transcatheter heart valve disposed inside the docking station.
Figure 10C:
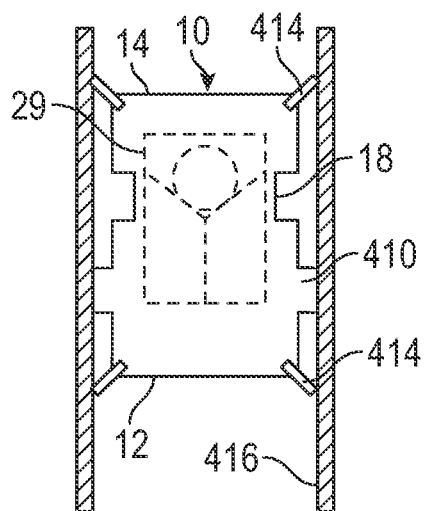
FIG. 10C illustrates an exemplary embodiment of a docking station with a transcatheter heart valve disposed inside the docking station.
Figure 10D:
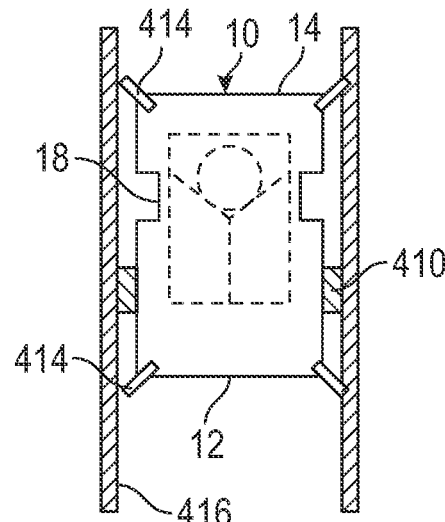
FIG. 10D illustrates an exemplary embodiment of a docking station with a transcatheter heart valve disposed inside the docking station.

FIGS. 10A-10C illustrate that the docking station 10 can have any combination of one or more than one different types of valve seats 18 and sealing portions 410. In the example illustrated by FIG. 10A, the valve seat 18 is a separate component that is attached to the body of the docking station 10 and the sealing portion is integrally formed with the body of the docking station. In the example illustrated by FIG. 10B, the valve seat 18 is a separate component that is attached to the body of the docking station 10 and the sealing portion 410 is a separate component that is attached to the body of the docking station. In the example illustrated by FIG. 10C, the valve seat 18 is integrally formed with the body of the docking station 10 and the sealing portion is integrally formed with the body of the docking station. In the example illustrated by FIG. 10D, the valve seat 18 is integrally formed with the body of the docking station 10 and the sealing portion is a separate component that is attached to the body of the docking station 10.

As mentioned above, the length of the pulmonary artery PA and other anatomical structures of the circulatory system may vary greatly from patient to patient. Referring to FIGS. 11A-11D, in one exemplary embodiment the length of the docking station 10 is adjustable as indicated by arrow 1100. This adjustability 1100 refers to the ability of the implanted/expanded length of the docking station to be adjusted, rather than the inherent change in length that occurs when a stent expands from a compressed state to an expanded state. The length may be adjusted in a wide variety of different ways. In the example illustrated by FIGS. 11A-11D, the docking station 10 includes a first half 1102 and a second half 1104. The use of the word "half" as used herein with respect to two part docking stations is synonymous with "portion" and does not require the first and second half or first and second portion to be equal in size, i.e., the first half could be larger/longer than the second half and vice versa. In one embodiment, the second half 1104 can be inserted or "telescoped" into the first half 1102. The amount of insertion or "telescoping" sets the length of the docking station 10. Any of the docking stations 10 shown and described in this patent application can be adjustable in length by making the docking stations from two parts that are telescoped together or are otherwise adjustable relative to each other. In one embodiment, a length of a single-piece docking station can be collapsible and expandable. In one embodiment, a docking station may be formed of a material that can change shape to adjust the length. In one embodiment, more than two portions (e.g., 3, 4, or more portions) can be combined in similar ways and include one or more similar features as first half 1102 and second half 1104.

In one exemplary embodiment, the length of the docking station 10 can be adjusted in the pulmonary artery PA by first deploying the first half 1102 of the docking station 10 in the pulmonary artery. For example, the first half 1102 may be positioned and expanded as desired, e.g., such that a distal end 1106 of the first half is aligned with or extends somewhat past the branch of the pulmonary artery. After the first half 1102 is expanded in the pulmonary artery, the compressed second half 1104 can be positioned with a distal end 1110 disposed in the proximal end 1108 of the first half 1102. In one embodiment, the position of the second half 1104 is selected such that the sealing portion 410 and retaining portion 414 will make contact with the pulmonary artery and set the position of the docking station 10 in the pulmonary artery. Once properly positioned, the second half 1104 is expanded. In one embodiment, the distal end of 1110 of the second half 1104 frictionally engages the proximal end 1108 of the first half to secure the two halves 1102, 1104 together. In one embodiment, a lock(s), locking mechanism, suture(s), interlacing, link(s) and/or other attachment device/mechanism may be used to help secure the halves/portions together.

Figure 11A:
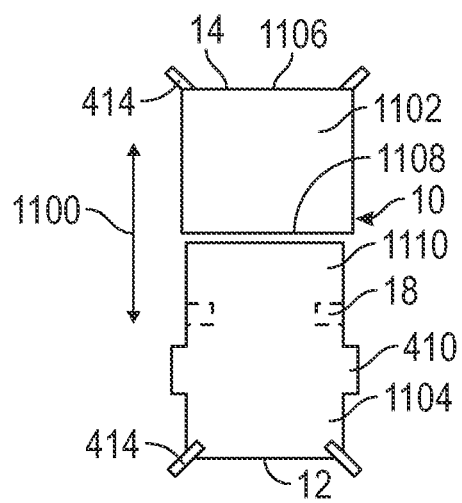
FIG. 11A illustrates an exemplary embodiment of a telescoping docking station.
Figure 11B:
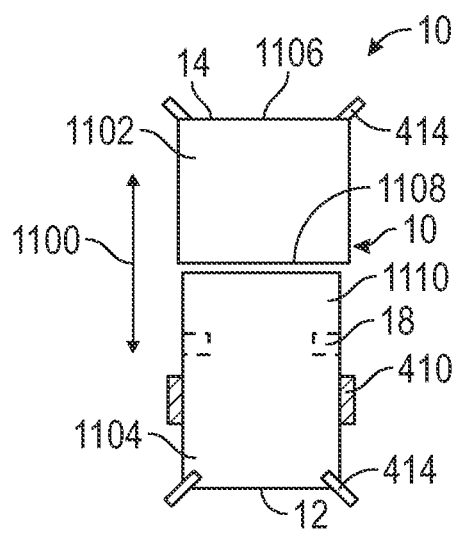
FIG. 11B illustrates an exemplary embodiment of a telescoping docking station.
Figure 11C:
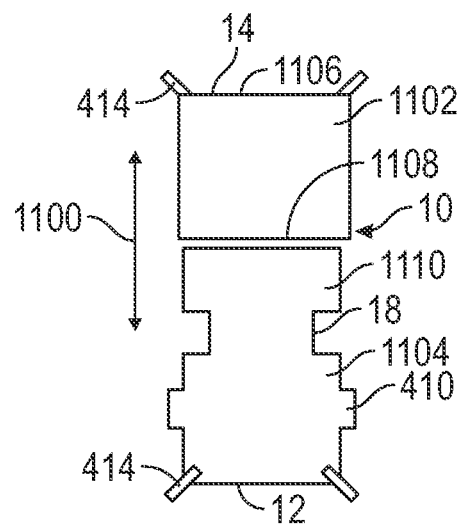
FIG. 11C illustrates an exemplary embodiment of a telescoping docking station.
Figure 11D:
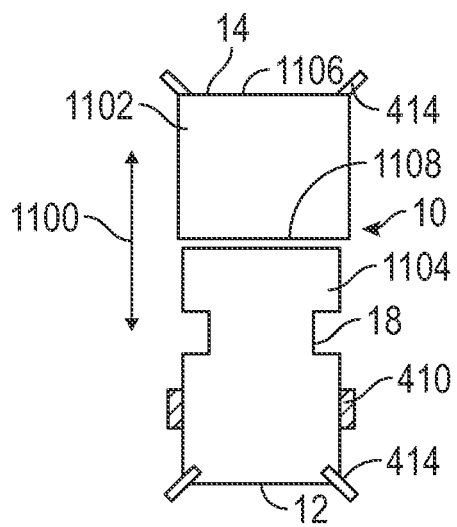
FIG. 11D illustrates an exemplary embodiment of telescoping docking station.
Figure 12A:
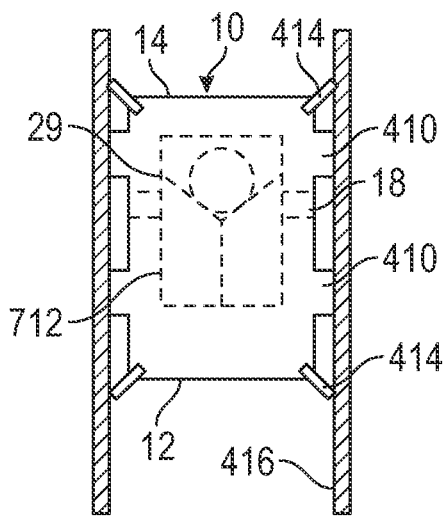
FIG. 12A illustrates an exemplary embodiment of a docking station with a transcatheter heart valve disposed inside the docking station.
Figure 12B:
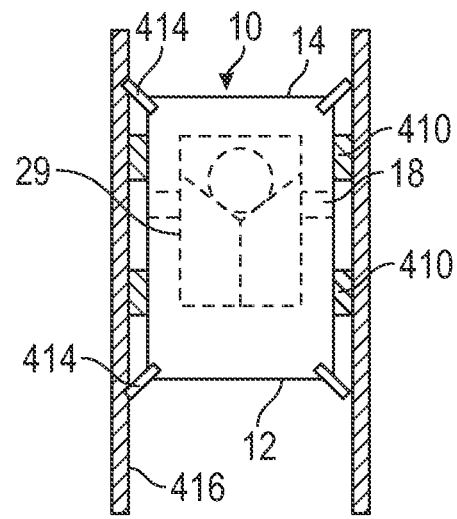
FIG. 12B illustrates an exemplary embodiment of a docking station with a transcatheter heart valve disposed inside the docking station.
Figure 12C:
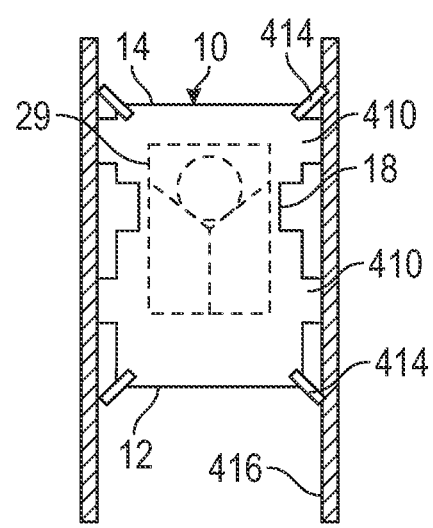
FIG. 12C illustrates an exemplary embodiment of a docking station with a transcatheter heart valve disposed inside the docking station.
Figure 12D:
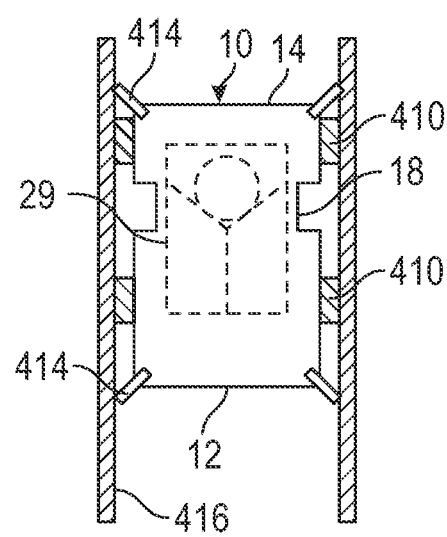
FIG. 12D illustrates an exemplary embodiment of a docking station with a transcatheter heart valve disposed inside the docking station.
Figure 13A:
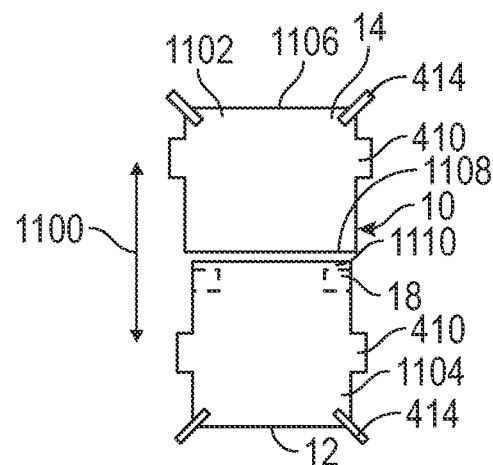
FIG. 13A illustrates an exemplary embodiment of a telescoping docking station.
Figure 13B:
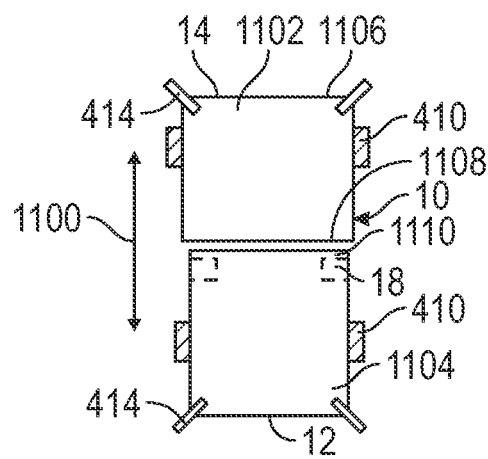
FIG. 13B illustrates an exemplary embodiment of a telescoping docking station.
Figure 13C:
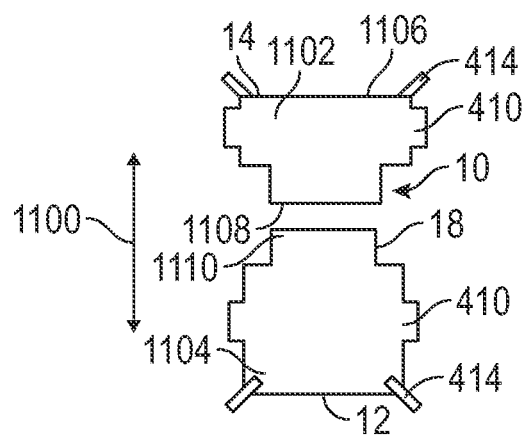
FIG. 13C illustrates an exemplary embodiment of a telescoping docking station.
Figure 13D:
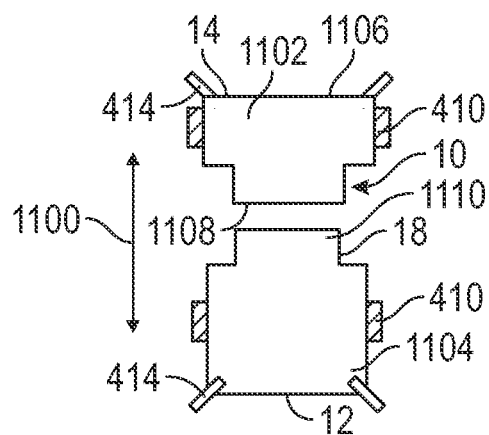
FIG. 13D illustrates an exemplary embodiment of a telescoping docking station.

In the examples illustrated by FIGS. 11A-11D, the seat 18 and the sealing portion 410 are included on the second half 1104 of the docking station 10. However, in other embodiments the seat 18 and/or the sealing portion 410 can be included on the first half 1102. FIGS. 11A-11C illustrate that the halves 1102, 1104 of the docking station 10 can have any combination of different types of valve seats 18 and sealing portions 410. In the example illustrated by FIG. 11A, the valve seat 18 is a separate component that is attached to the body of the docking station half 1104 and the sealing portion is integrally formed with the body of the docking station half 1104. In the example illustrated by FIG. 11B, the valve seat 18 is a separate component that is attached to the body of the docking station half 1104 and the sealing portion 410 is a separate component that is attached to the body of the docking station half 1104. In the example illustrated by FIG. 11C, the valve seat 18 is integrally formed with the body of the docking station half 1104 and the sealing portion is integrally formed with the body of the docking station half 1104. In the example illustrated by FIG. 11D, the valve seat 18 is integrally formed with the body of the docking station half 1104 and the sealing portion 410 is a separate component that is attached to the body of the docking station half 1104.

FIGS. 12A-12D illustrate exemplary embodiments of docking stations 10 with two sealing portions 410. The docking station 10 can have any combination of one or more than one different types of valve seats 18 and sealing portions 410. In the example illustrated by FIG. 12A, the valve seat 18 is a separate component that is attached to the body of the docking station 10 and the sealing portions 410 is integrally formed with the body of the docking station. In the example illustrated by FIG. 12B, the valve seat 18 is a separate component that is attached to the body of the docking station 10 and the sealing portions 410 are separate components that are attached to the body of the docking station. In the example illustrated by FIG. 12C, the valve seat 18 is integrally formed with the body of the docking station 10 and the sealing portions are integrally formed with the body of the docking station. In the example illustrated by FIG. 12D, the valve seat 18 is integrally formed with the body of the docking station 10 and the sealing portions are separate components that are attached to the body of the docking station 10.

FIGS. 13A-13D illustrate that the docking stations illustrated by FIGS. 12A-12D can be two-piece telescoping docking stations. The pieces 1102, 1104 of the docking station 10 can have any combination of one or more than one different types of valve seats 18 and sealing portions 410 on either or both of the two pieces. In the example illustrated by FIG. 13A, the first half 1102 includes an integral sealing portion 410. The second half 1104 includes a valve seat 18 that is a separate component that is attached to the body of the docking station 10 and the sealing portions 410 is integrally formed with the body of the docking station. In the example illustrated by FIG. 13B, the first half 1102 includes a sealing portion 410 that is separate from the body of the first half 102. The valve seat 18 is a separate component that is attached to the body of the docking station 10 and the sealing portion 410 is a separate components that is attached to the body of the docking station. In the example illustrated by FIG. 13C, the first half 1102 includes an integral sealing portion 410. The valve seat 18 is integrally formed with the body of the second half 1104 of the docking station 10 and the sealing portion 410 is integrally formed with the body of the second half 1104. In the example illustrated by FIG. 12D, the first half 1102 includes a sealing portion 410 that is separate from the body of the first half 102. The valve seat 18 is integrally formed with the body of the second half 1104 of the docking station 10 and the sealing portion 410 is a separate components that is attached to the body of the second half 1104.

Referring to FIGS. 14A-14G, in one exemplary embodiment the docking station 10 can include a permeable portion 1400 that blood can flow through as indicated by arrows 1402 and an impermeable portion 1404 that blood cannot flow through. In one exemplary embodiment, the impermeable portion 1404 extends from at least the sealing portion 410 to the valve seat 18 to prevent blood from flowing around the valve 29. In one exemplary embodiment, the permeable portion 1400 allows blood to freely flow through it, so that portions of the docking station that do not seal against the inside surface 416 of the circulatory system or seal against the valve 29 do not block the flow of blood. For example, the docking station 10 may extend into the branch of the pulmonary artery and the portion 1400 of the docking station 10 that extends into the pulmonary artery freely allows blood to flow through the docking station 10. In one exemplary embodiment, the permeable portion 1400 allows blood to freely flow through it, so that areas 1420 between the docking station and the circulatory system are flushed with blood as the heart beats, thereby preventing blood stasis in the areas 1420.

The impermeable portion 1404 can take a wide variety of different forms. The impermeable portion 1404 may be any structure or material that prevents blood to flow through the impermeable portion 1404. For example, the body of the docking station 10 can be formed from wires or a lattice, such as a nitinol wire or lattice, and cells of body are covered by an impermeable material (See FIG. 18). A wide variety of different materials may be used as the impermeable material. For example, the impermeable material may be a blood-impermeable cloth, such as a PET cloth or biocompatible covering material such as a fabric that is treated with a coating that is impermeable to blood, polyester, or a processed biological material, such as pericardium.

Figure 14E:
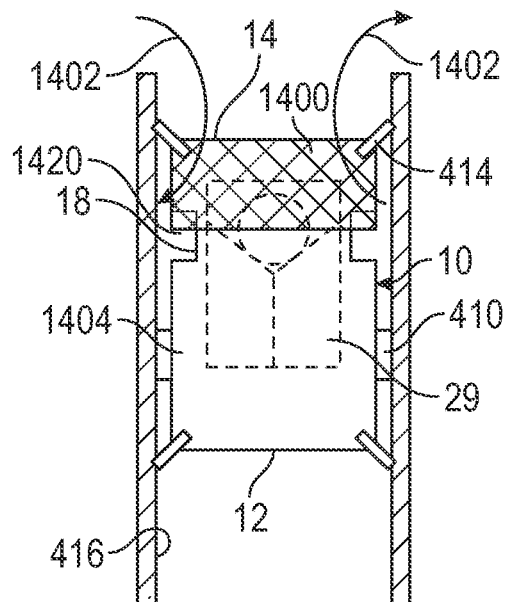
FIG. 14E illustrates an exemplary embodiment of a docking station with a transcatheter heart valve disposed inside the docking station.
Figure 14F:
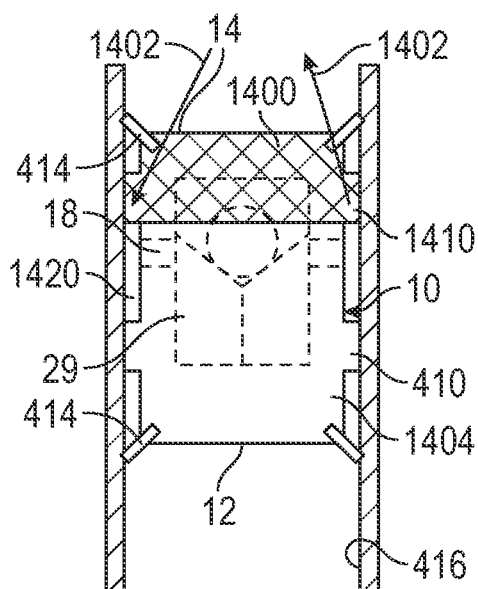
FIG. 14F illustrates an exemplary embodiment of a docking station with a transcatheter heart valve disposed inside the docking station.
Figure 14G:
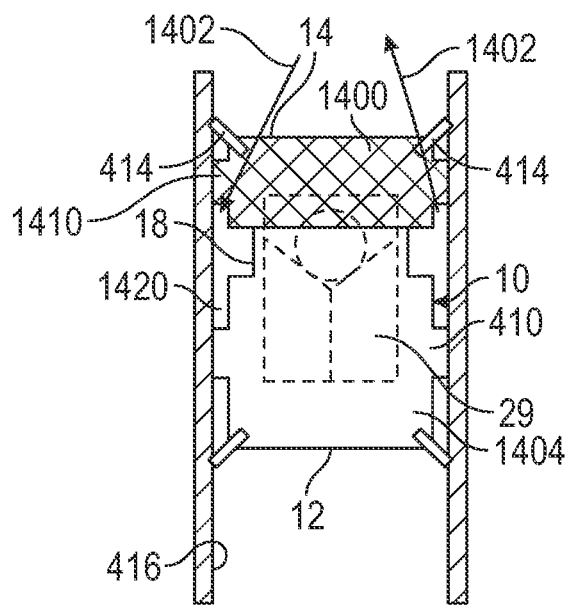
FIG. 14G illustrates an exemplary embodiment of a docking station with a transcatheter heart valve disposed inside the docking station.
Figure 15A:
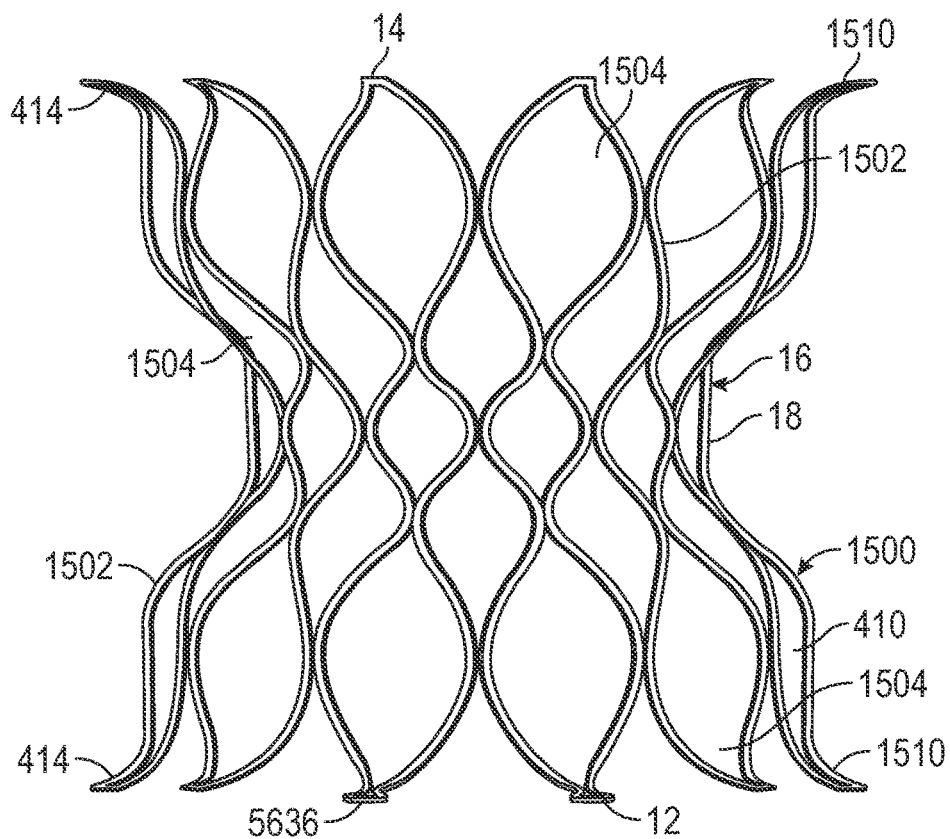
FIG. 15A is a side view of an exemplary embodiment of a frame of a docking station.
Figure 15B:
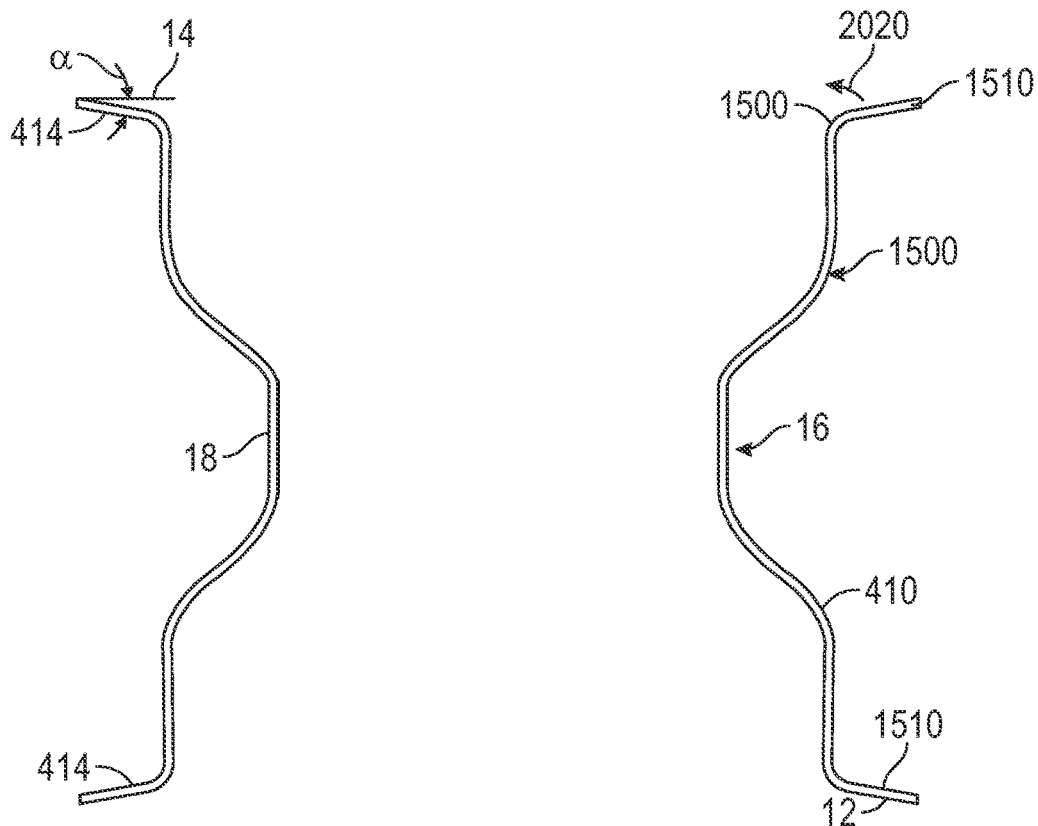
FIG. 15B illustrates a side profile of the frame of illustrated by FIG. 15A.

FIGS. 14A-14G illustrate that a wide variety of docking station configurations can be provided with a permeable portion 1402. The sealing portion 410 may be integrally formed with the body of the docking station as illustrated by FIGS. 14B, 14D, and 14F or separate as illustrated by FIGS. 14C, 14E and 14G. In FIGS. 14F and 14G the docking station 10 includes portions 1410. These portions 1410 are similar to the sealing portions 410, but a seal is not formed with the inner surface 416 of the circulatory system, because the portion 1410 is part of the permeable portion 1402. The valve seat 18 may be separately formed from the body of the docking station as illustrated by FIGS. 14A-14C or integrally formed with the body of the docking station 10 as illustrated by FIGS. 14D-14G.

FIGS. 15A, 15B, 16, 17A, and 17B illustrate an exemplary embodiment of a frame 1500 or body of a docking station 10. The frame 1500 or body can take a wide variety of different forms and FIGS. 15A, 15B, 16, 17A, and 17B illustrate just one of the many possible configurations. In the example illustrated by FIGS. 15A, 15B, 16, 17A, 17B, and 18, the docking station 10 has a relatively wider proximal inflow end 12 and distal outflow end 14, and a relatively narrower portion 16 that forms the seat 18 in between the ends 12, 14. In the example illustrated by FIGS. 15A, 15B, 17A, and 17B, the frame 1500 of the docking station 10 is preferably a wide stent comprised of a plurality of metal struts 1502 that form cells 1504. In the example of FIGS. 15A, 15B, 17A, and 17B, the frame 1500 has a generally hourglass-shape that has a narrow portion 16, which forms the valve seat 18 when covered by an impermeable material, in between the proximal and distal ends 12, 14. As described below, the valve 18 expands in the narrow portion 16, which forms the valve seat 18.

Figure 16:
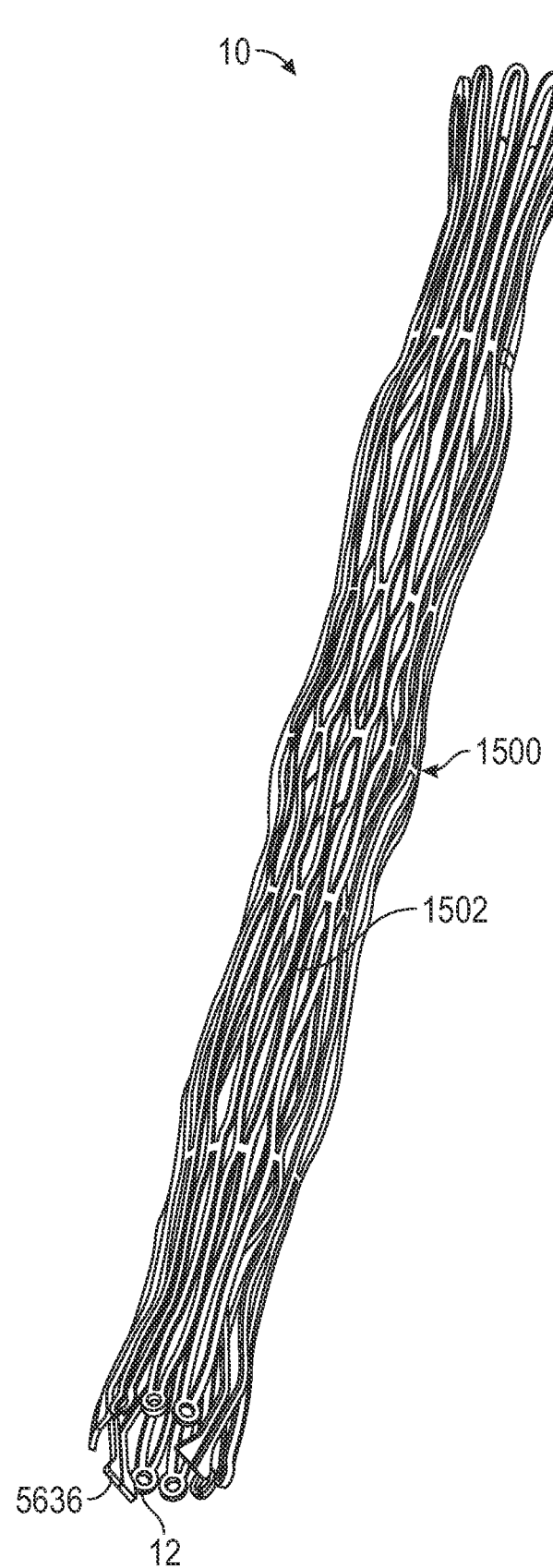
FIG. 16 illustrates the docking station frame of FIG. 15A in a compressed state.
Figure 17A:
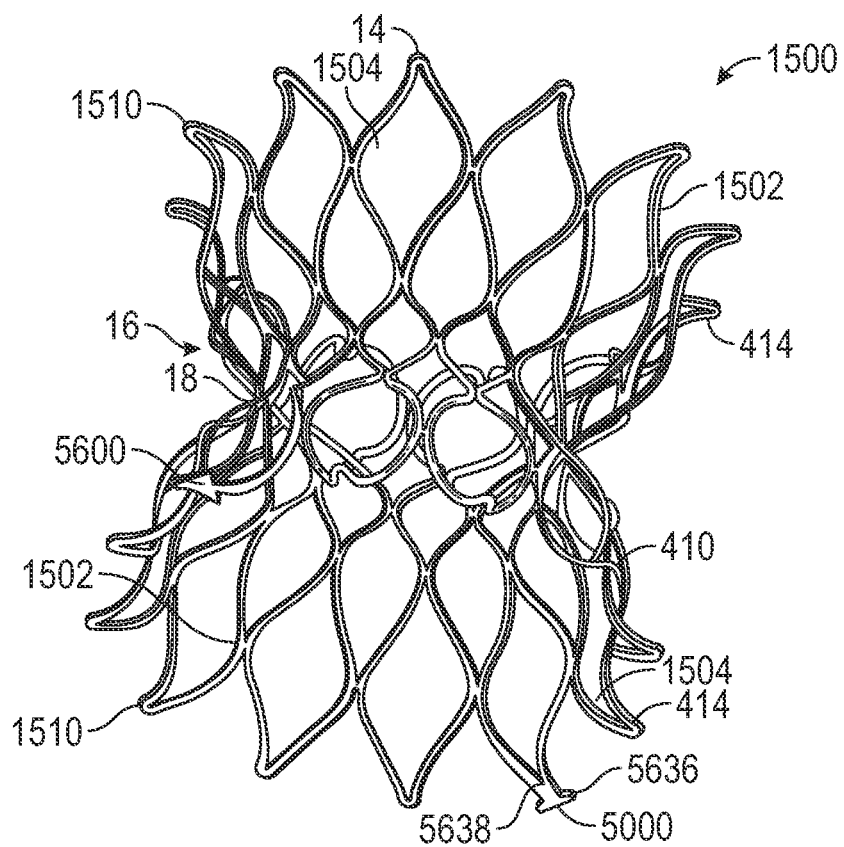
FIG. 17A is a perspective view of the docking station frame of FIG. 15A.
Figure 17B:
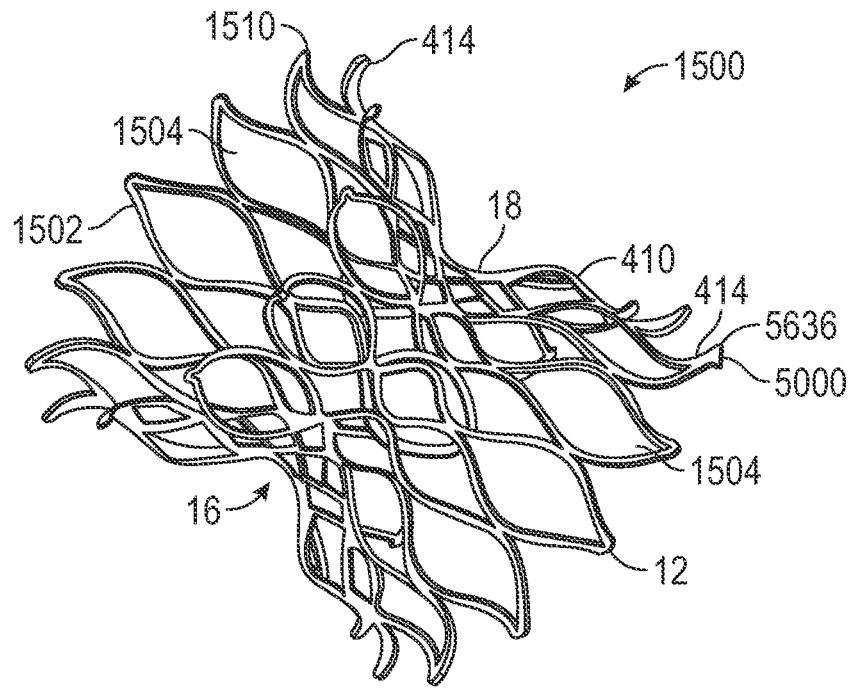
FIG. 17B is a perspective view of the docking station frame of FIG. 15A.

FIGS. 15A, 15B, 17A, and 17B illustrate the frame 1500 in its unconstrained, expanded condition. In this exemplary embodiment, the retaining portions 414 comprise ends 1510 of the metal struts 1502 at the proximal and distal ends 12, 14. The sealing portion 410 is between the retaining portions 414 and the waist 16. In the unconstrained condition, the retaining portions 414 extend generally radially outward and are radially outward of the sealing portion 410. FIG. 16 illustrates the frame 16 in the compressed state for delivery and expansion by a catheter. The docking station can be made from a very resilient or compliant material to accommodate large variations in the anatomy. For example, the docking station can be made from a highly flexible metal, metal alloy, polymer, or an open cell foam. An example of a highly resilient metal is nitinol, but other metals and highly resilient or compliant non-metal materials can be used. The docking station 10 may be self-expanding, manually expandable (e.g., expandable via balloon), or mechanically expandable. A self-expanding docking station 10 may be made of a shape memory material such as, for example, nitinol.

Figure 18:
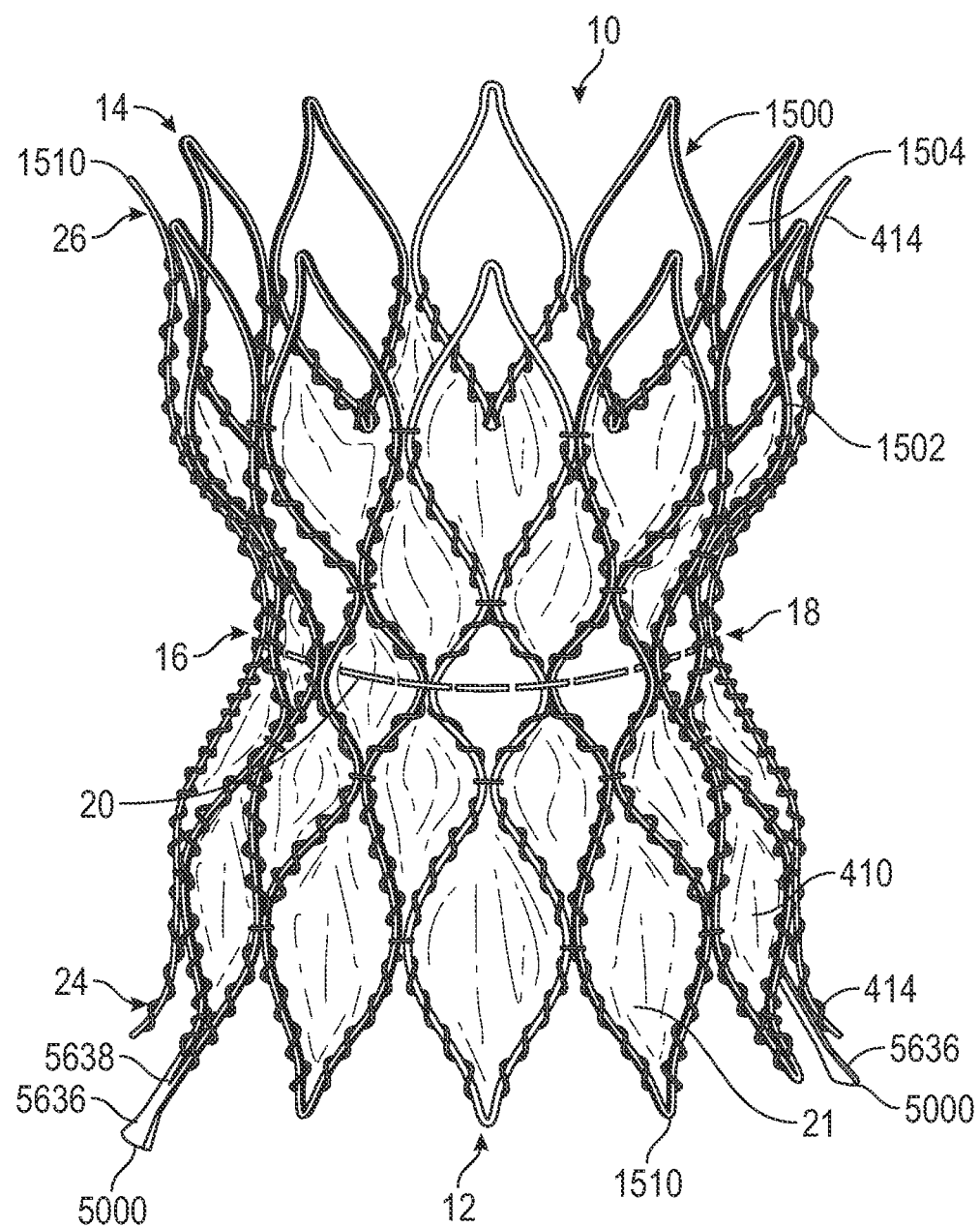
FIG. 18 is a perspective view of an exemplary embodiment of a docking station having a plurality of covered cells and a plurality of open cells.
Figure 19:
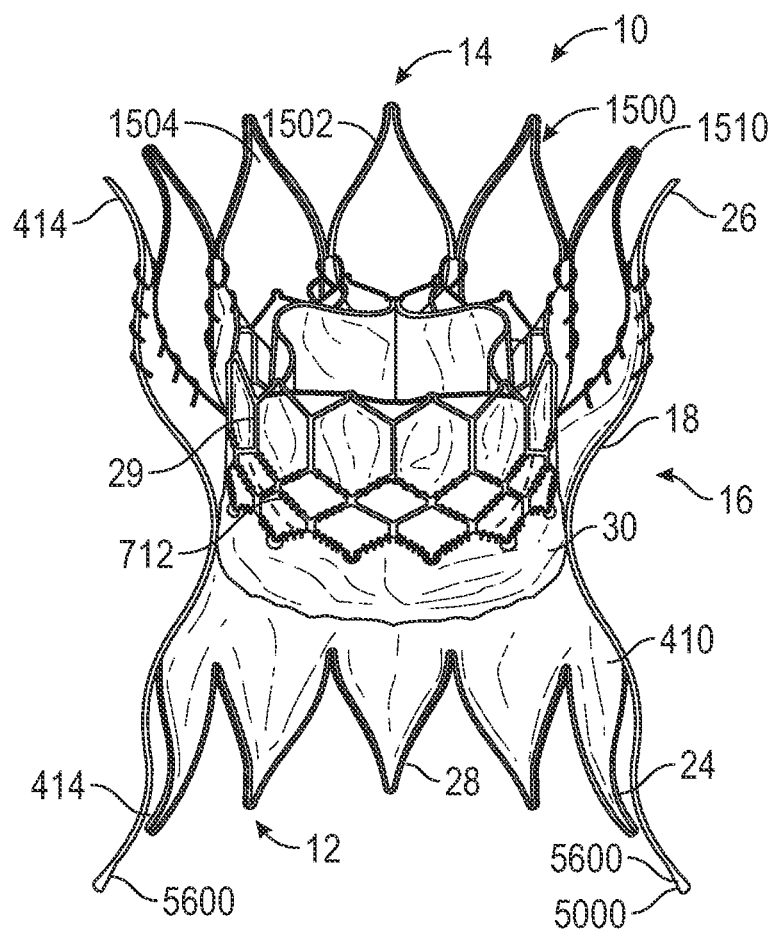
FIG. 19 is a perspective view of the docking station illustrated by FIG. 18 with a portion cut away to illustrate a transcatheter heart valve expanded into place in the docking station.

FIG. 18 illustrates the frame 1500 with impermeable material 21 attached to the frame 1500 to form the docking station 10. Referring to FIG. 18, in one exemplary embodiment a band 20 extends about the waist or narrow portion 16, or is integral to the waist to form an unexpandable or substantially unexpandable valve seat 18. The band 20 stiffens the waist and, once the docking station is deployed and expanded, makes the waist/valve seat relatively unexpandable in its deployed configuration. In the example illustrated by FIG. 19, the valve 29 is secured by expansion of its collapsible frame into the narrow portion 16, which forms the valve seat 18, of the docking station 10. As is explained above, the unexpandable or substantially unexpandable valve seat 18 prevents the radially outward force of the valve 29 from being transferred to the inside surface 416 of the circulatory system. However in another exemplary embodiment, the waist/valve seat of the deployed docking station may optionally expand slightly in an elastic fashion when the valve is deployed against it. This optional elastic expansion of the waist 18 may put pressure on the valve 29 to help hold the valve 29 in place within the docking station.

The band can take a wide variety of different forms and can be made from a wide variety of different materials. The band 20 can be made of PET, one or more sutures, fabric, metal, polymer, a biocompatible tape, or other relatively unexpandable materials known in the art that are sufficient to maintain the shape of the valve seat 18 and hold the valve 29 in place. The band can extend about the exterior of the stent, or can be an integral part of it, such as when fabric or another material is interwoven into or through cells of the stent. The band 20 may be narrow, such as the suture band in FIG. 18, or may be wider. The band can be a variety of widths, lengths, and thicknesses. In one non-limiting example, the valve seat 18 is between 27-28 mm wide, although the diameter of the valve seat should be within the operating range of the particular valve 29 that will be secured within the valve seat 18, and can be different than the foregoing example. The valve 29, when docked within the docking station, can optionally expand around either side of the valve seat slightly. This aspect, sometimes referred to as a "dogbone" (e.g., because of the shape it forms around the valve seat or band), can also help hold the valve in place.

Figure 20:
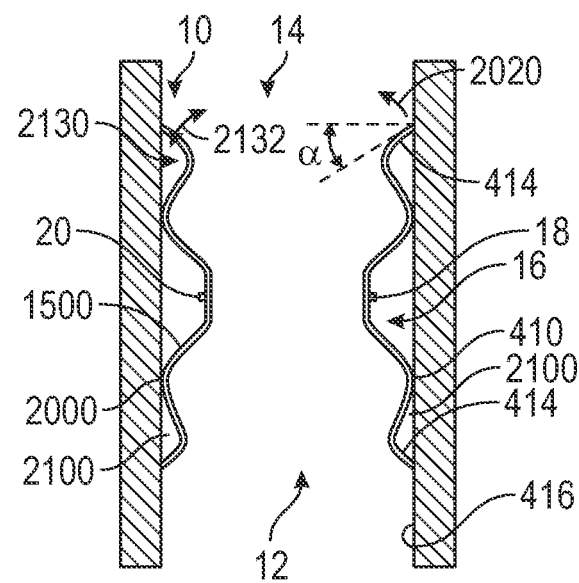
FIG. 20 illustrates a side profile of the docking station illustrated by FIG. 18 when implanted in a vessel of the circulatory system.
Figure 21:
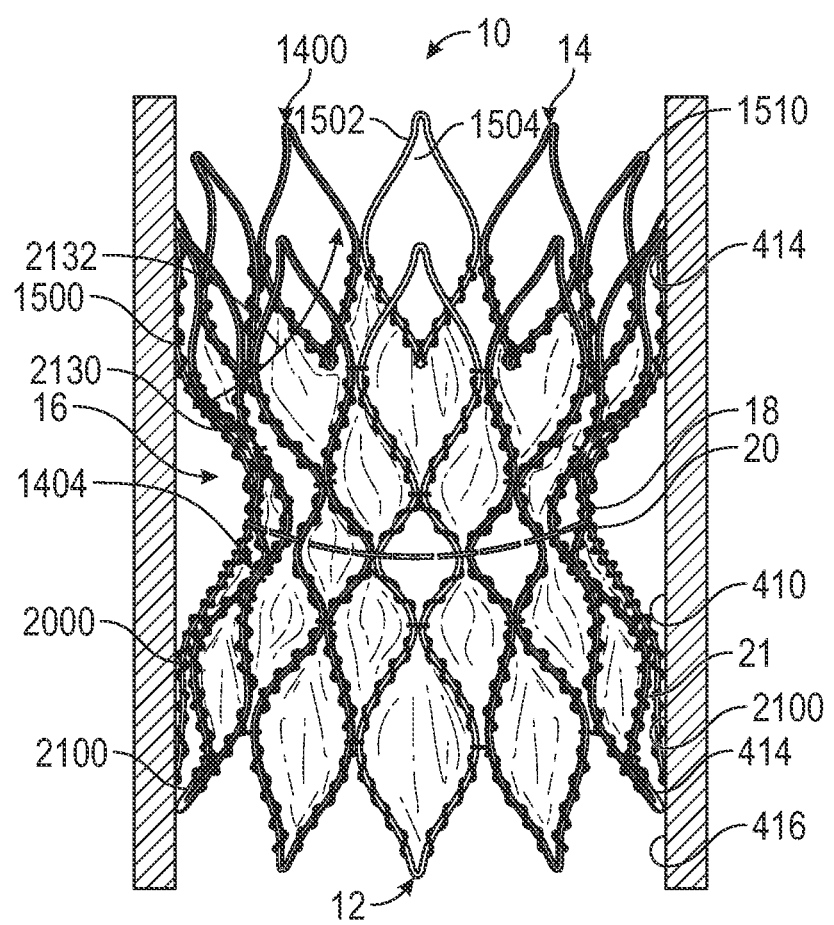
FIG. 21 illustrates a perspective view of the of the docking station illustrated by FIG. 18 when installed in a vessel of the circulatory system.

FIGS. 20 and 21 illustrate the docking station 10 of FIG. 18 implanted in the circulatory system, such as in the pulmonary artery. The sealing portions 410 provide a seal between the docking station 10 and an interior surface 416 of the circulatory system. In the example of FIGS. 20 and 21, the sealing portion 410 is formed by providing an impermeable material 21 (See FIG. 21) over the frame 1500 or a portion thereof, In particular, the sealing portion 410 can comprise the lower, rounded, radially outward extending portion 2000 of the frame 1500. In an exemplary embodiment, the impermeable material 21 extends from at least the portion 2000 of the frame 1500 to the valve seat 18. This makes the docking station impermeable from the sealing portion 410 to the valve seal 18. As such, all blood flowing in the inflow direction 12 toward the outflow direction 14 is directed to the valve seat 18 (and valve 29 once installed or deployed in the valve seat).

In a preferred embodiment of a docking station 10, the inflow portion has walls that are impermeable to blood, but the outflow portion walls are relatively open. In one approach, the inflow end portion 12, the mid-section 16, and a portion of the outflow end portion 14 are covered with a blood-impermeable fabric 21, which may be sewn onto the stent or otherwise attached by a method known in the art. The impermeability of the inflow portion of the stent helps to funnel blood into the docking station 10 and ultimately flow through the valve that is to be expanded and secured within the docking station 10.

From another perspective, this embodiment of a docking station is designed to seal at the proximal inflow section 2000 to create a conduit for blood flow. The distal outflow section, however, is generally left open, thereby allowing the docking station 10 to be placed higher in the pulmonary artery without restricting blood flow. For example, the permeable portion 1400 may extend into the branch of the pulmonary artery and not impede or not significantly impede the flow of blood past the branch. In one embodiment, blood-impermeable cloth, such as a PET cloth for example, or other material covers the proximal inflow section, but the covering does not cover any or at least a portion of the distal outflow section 14. As one non-limiting example, when the docking station 10 is placed in the pulmonary artery, which is a large vessel, the significant volume of blood flowing through the artery is funneled into the valve 29 by the cloth covering 21. The cloth 21 is fluid impermeable so that blood cannot pass through. Again, a variety of other biocompatible covering materials may be used such as, for example, foam or a fabric that is treated with a coating that is impermeable to blood, polyester, or a processed biological material, such as pericardium.

In the example illustrated by FIG. 21, more of the docking station frame 1500 is provided with the impermeable material 21, forming a relatively large impermeable portion 1404. In the example illustrated by FIG. 21, the impermeable portion 1404 extends from the inflow end 12 and stops one row of cells 1504 before the outflow end. As such, the most distal row of cells 1504 form a permeable portion 1400. However, more rows of cells 1504 can be uncovered by the impermeable material to form a larger permeable portion. The permeable portion 1400 allows blood to flow into and out of the area 2130 as indicated by arrows 2132. With respect to the inflow end 12, it should be noted that since the cells 1504 are generally diamond shaped, blood is able to flow between the docking station 10 and the surface 416, until the sealing portion 410 is reached. That is, blood can flow into and out of the areas 2100 in one exemplary embodiment.

The valve seat 18 can provide a supporting surface for implanting or deploying a valve 29 in the docking station 10. The retaining portions 414 can retain the docking station 10 at the implantation position or deployment site in the circulatory system. The illustrated retaining portions have an outwardly curving flare that helps secure the docking station 10 within the artery. "Outwardly" as used herein means extending away from the central longitudinal axis of the docking station. As can be seen in FIG. 20, when the docking station 10 is compressed by the inside surface 416, the retaining portions 414 engage the surface 416 at an angle α (normal to the surface to the tangent of the midpoint of the surface of the retaining portion 414) that can be between 30 and 60 degrees, such as about 45 degrees, rather than extending substantially radially outward (i.e. a is 0 to 20 degrees or about 10 degrees) as in the uncompressed condition (See FIG. 15B). This inward bending of the retaining portions 414 as indicated by arrow 2020 acts to retain the docking station 10 in the circulatory system. The retaining portions 14 are at the wider inflow end portion 12 and outflow end portion 14 and press against the inner surface 416. The flared retaining portions 414 engage into the surrounding anatomy in the circulatory system, such as the pulmonic space. In one exemplary embodiment, the flares serve as a stop, which locks the device in place. When an axial force is applied to the docking station 10, the flared retaining portions 414 are pushed by the force into the surrounding tissue to resist migration of the stent as described in more detail below. In a specific embodiment, the docking station generally has an hourglass shape, with wider distal and proximal end portions that have the flared retaining portion and a narrow, banded waist in between the ends, into which the valve is expanded.

Figure 22:
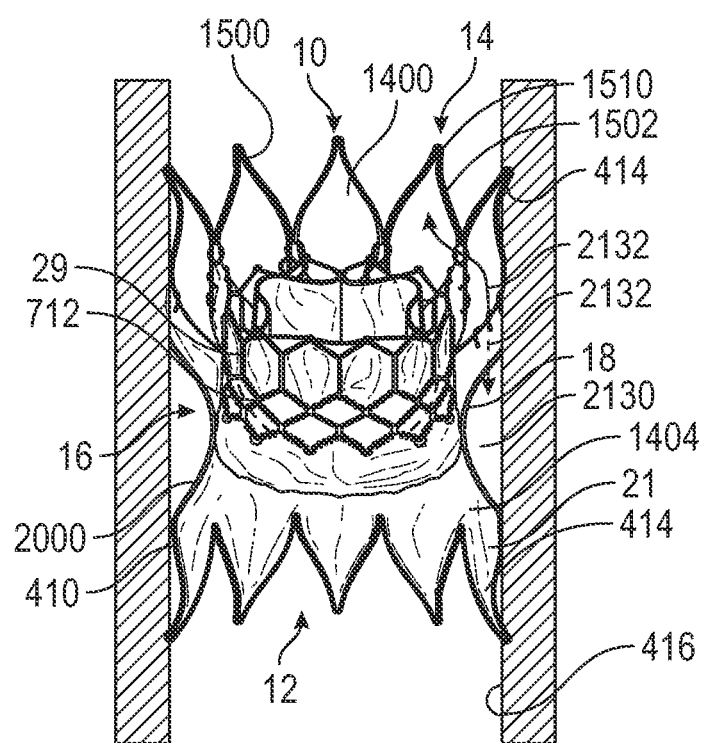
FIG. 22 illustrates a perspective view of the of the docking station and valve illustrated by FIG. 19 when implanted in a vessel of the circulatory system.

FIG. 22 illustrates the docking station 10 deployed in the circulatory system and a valve 29 deployed in the docking station 10. After the docking station 10 is deployed, the valve 29 is in a compressed form and is introduced into the valve seat 18 of the docking station 10. The valve 29 is expanded in the docking station, such that the valve 29 engages the valve seat 18. In the example illustrated by FIG. 22, the docking station 10 is longer than the valve. However, in one embodiment, the docking station 10 may be the same length or shorter than the length of the valve 10.

The valve 29 may be delivered to the site of the docking station via conventional means, such as by balloon or mechanical expansion or by self-expansion. When the valve 29 is expanded, it nests in the valve seat of the docking station 10. In one embodiment, the banded waist is slightly elastic and exerts an elastic force against the valve 29, to help hold the THV in place.

Figure 23A:
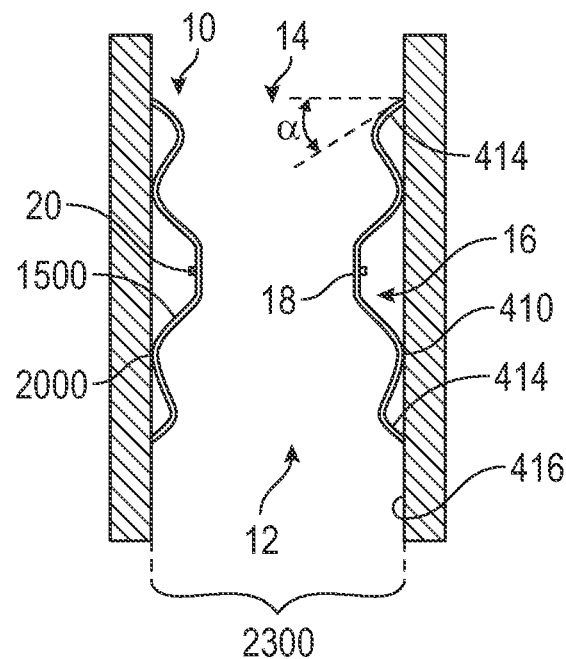
FIGS. 23A and 23B illustrate a side profiles of the docking station illustrated by FIG. 18 when implanted in different size vessels of the circulatory system.
Figure 23B:
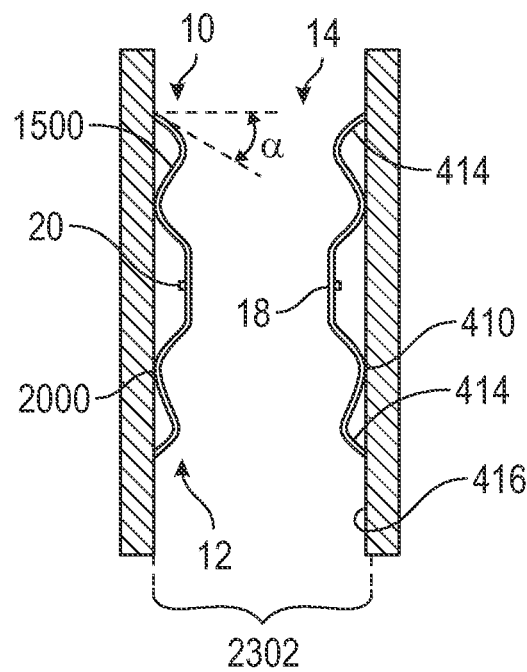

FIGS. 23A and 23B illustrate that the docking station 10 can be used to adapt a variety of different sizes of circulatory system anatomies for implantation of a valve 29 having a consistent size. In the example of FIGS. 23A and 23B, the same size docking station 10 is deployed in two different sized vessels 2300, 2302, such as two differently sized pulmonary arteries PA. In the example, the vessel 2300 illustrated by FIG. 23A has a larger effective diameter than the vessel 2302 illustrated by FIG. 23B. (Note that in this patent application the size of the anatomy of the circulatory system is referred to by the term "diameter" or "effective diameter." The anatomy of the circulatory system is often not circular. The terms "diameter" and "effective diameter" herein refers to the diameter of a circle or disc that could be deformed to fit within the non-circular anatomy.) In the example illustrated by FIGS. 23A and 23B, the sealing portion 410 and the retaining portions 414 conform to contact each vessel 2300, 2302. However, the valve seat 18 remains the same size, even though the sealing portion 410 and the retaining portions 414 are compressed. In this manner, the docking station 10 adapts a wide variety of different anatomical sizes for implantation of a standard or single sized valve. For example, the docking station may conform to vessel diameters of 25 mm and 40 mm, such as 27 mm and 38 mm and provide a constant or substantially constant diameter valve seat of mom to 30 mm, such as 27 mm to 28 mm. However, the valve seat 10 can be adapted for applications where the vessel diameter is larger or smaller than 25 mm to 40 mm and provide valve seats that are larger or smaller than mom to 30 mm.

Referring to FIGS. 23A and 23B, a band 20 maintains a constant or substantially constant diameter of the valve seat 18, even as the proximal and distal ends of the docking station expand to respective diameters necessary to engage with the inside surface 416. The diameter of the pulmonary artery PA can vary considerably from patient to patient, but the valve seat 18 in the deployed configuration consistently has a diameter that is within an acceptable range for the valve 29.

Figure 24:
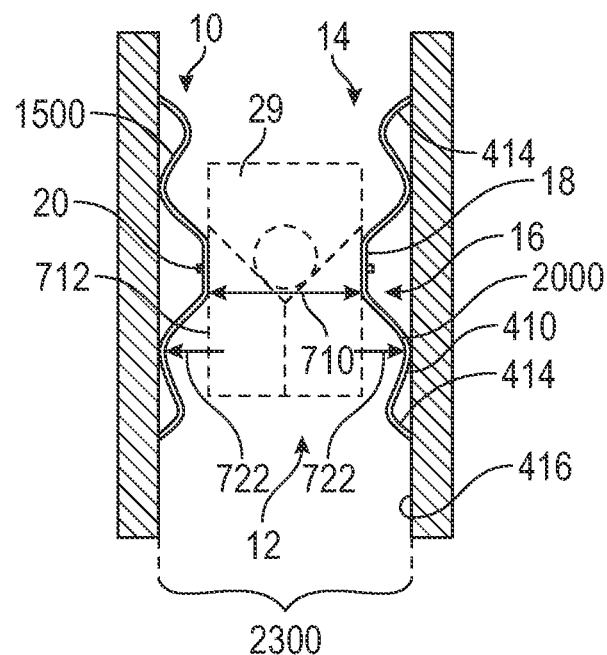
FIGS. 24 and 25 illustrate side profiles of the docking station illustrated by FIG. 18 when implanted different sized vessels of the circulatory system with a schematically illustrated transcatheter heart valve having the same size installed or deployed in each docking station.
Figure 25:
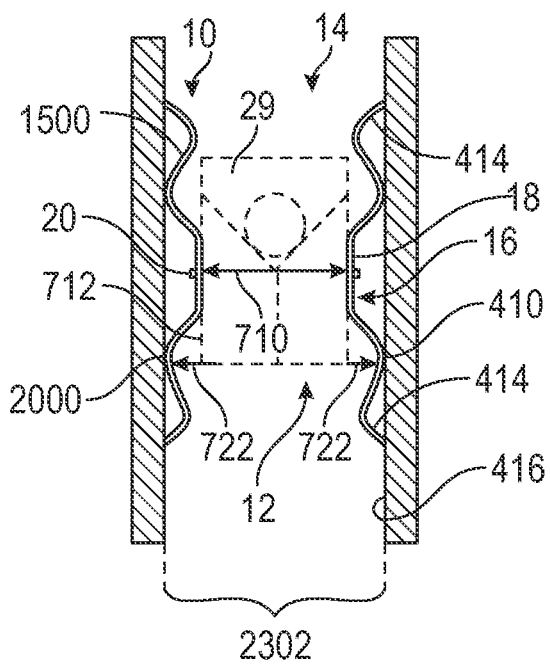

FIGS. 24 and 25 illustrate side profiles of the docking station 10 illustrated by FIG. 18 when implanted in different sized vessels 2300, 2302 of the circulatory system with a schematically illustrated transcatheter heart valve 29 having the same size installed or deployed in each docking station 10. In this example, the docking station 10 both accommodates vessels 2300, 2302 having a variety of different sizes and acts as an isolator that prevents or substantially prevents radial outward forces of the valve 29 from being transferred to the vessels. The valve seat 18 is not expanded radially outwardly or is not substantially expanded radially outward by the radially outward force of the valve 29 and the anchoring/retaining portions 414 and the sealing portions 410 impart only relatively small radially outward force on the vessels 2300, 2302 (as compared to the radially outward force applied to the valve seat 18 by the valve 29), even when the docking station is deployed in a vessel 2302 having a smaller diameter.

In the example illustrated by FIGS. 24 and 25, the stent or frame 712 of the valve 29 expands radially outward or is expanded radially outward to import the high force 710 on the valve seat 18 of the docking station 10. This high radially outward force 710 secures the valve 29 to the valve seat 18 of the docking station 10. However, since the valve seat 18 is not expanded or is not substantially expanded by the force 710, the force 710 is isolated from the circulatory system, rather than being used to secure the docking station in the circulatory system.

In an exemplary embodiment, the radially outward force 722 of the sealing portions 410 to both the larger vessel 2300 and the smaller vessel is substantially smaller than the radially outward force 710 applied by the valve 29 to the valve seat 18. For example, for the smallest vessel to be adapted by the docking station 10 for valve implantation, the radially outward sealing force 722 can be less than ½ the radially outward force 710 applied by the valve, less than ⅓ the radially outward force 710 applied by the valve, less than ¼ the radially outward force 710 applied by the valve, less than ⅛, or even less than ¹⁄₁₀ the radially outward force 710 applied by the valve. In one exemplary embodiment, the radially outward force 722 of the sealing portions 410 is selected to provide a seal between the inner surface 416 and the sealing portion 410, but is not sufficient by itself to retain the position of the valve 29 and docking station 10 in the circulatory system. In one embodiment, the radially outward force 722 is sufficient to retain the position of the valve 29 and docking station 10 in the circulatory system.

In an exemplary embodiment, the docking station 10 illustrated by FIG. 18 also includes anchoring/retaining portions 414 that apply radially outward forces 720 that are substantially smaller than the radially outward force 710 applied by the valve 29 to the valve seat 18. For example, for the smallest vessel to be adapted by the docking station 10 for valve implantation, the radially outward sealing force 720 can be less than ½ the radially outward force 710 applied by the valve, less than ⅓ the radially outward force 710 applied by the valve, less than ¼ the radially outward force 710 applied by the valve, less than ⅛, or even less than ¹⁄₁₀ the radially outward force 710 applied by the valve. In one embodiment, the radially outward force 720 of the anchoring/retaining portions 414 is not sufficient by itself to retain the position of the valve 29 and docking station 10 in the circulatory system. In one embodiment, the radially outward force 720 is sufficient to retain the position of the valve 29 and docking station 10 in the circulatory system.

In one exemplary embodiment, the docking station 10 frame 1500 is made from an elastic or superelastic material or metal. One such metal is nitinol. When the frame 1500 of the docking station 10 is made from a lattice of metal struts, the body can have the characteristics of a spring. Referring to FIG. 7C, like a spring, when the frame 1500 of the docking station 10 illustrated by FIGS. 24 and 25 is unconstrained and allowed to relax to its largest diameter the frame of the docking station applies little or no radially outward force. As the frame 1500 of the docking station 10 is compressed, like a spring, the radially outward force applied by the docking station increases. As is illustrated by FIG. 7C, in one exemplary embodiment the relationship of the radially outward force of the docking station frame 1500 to the expanded diameter of the docking station is non-linear, though it can also be linear. In the example illustrated by FIG. 7C, the curve 750 illustrates the relationship between the radially outward force exerted by the docking station 10 and the compressed diameter of the docking station. In the region 752, the curve 750 has a low slope. In this region 752 the radially outward force is low and changes only a small amount. In one exemplary embodiment, the region 752 corresponds to a diameter between 25 mm and 40 mm, such as between 27 mm and 38 mm. The radially outward force is small in the region 752, but is not zero. In the region 754, the curve 750 has a higher slope. In this region 754 the radially outward force increases significantly as the docking station is compressed. In one exemplary embodiment, the body of the stent is constructed to be in the low slope region 752 for both a largest vessel 2300 (FIG. 24) accommodated by the docking station 10 and a smallest vessel 2302 (FIG. 25). This allows the sealing portions 710 to apply only a small radially outward force to the inner surface 416 of the circulatory system over a wide range of diameters.

Figure 26A:
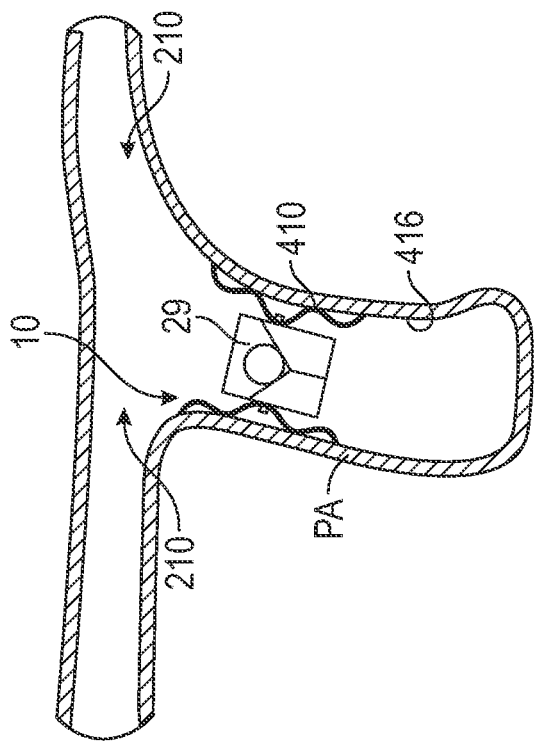
FIG. 26A is a sectional view illustrating a side profile of an exemplary embodiment of a docking station placed in a pulmonary artery.
Figure 26B:
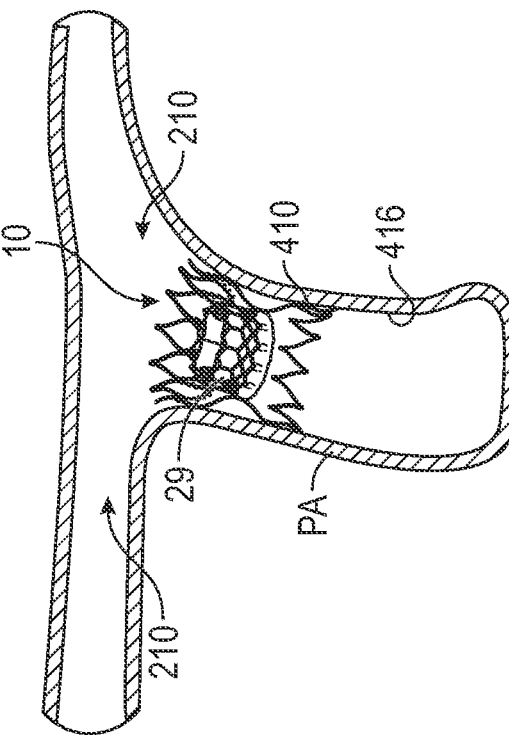
FIG. 26B is a sectional view illustrating a side profile of an exemplary embodiment of a docking station placed in a pulmonary artery and a schematically illustrated valve placed in the docking station.
Figure 26C:
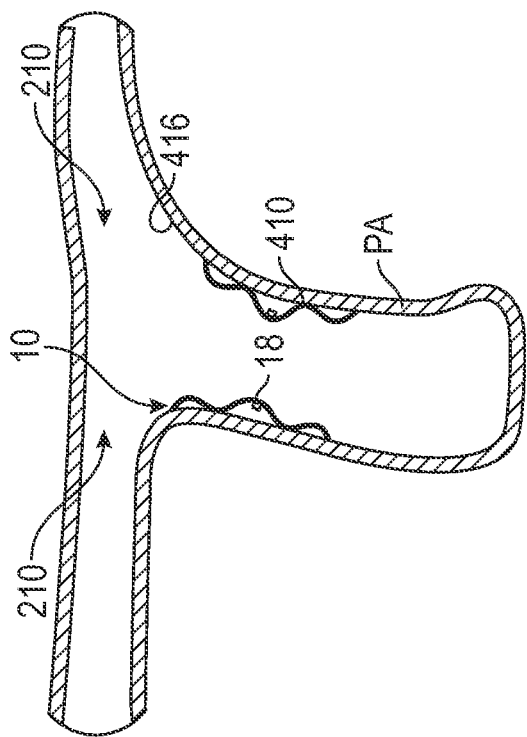
FIG. 26C is a sectional view illustrating an exemplary embodiment of a docking station placed in a pulmonary artery and a valve placed in the docking station.

FIGS. 26A-26C illustrate the docking station 10 of FIG. 18 implanted in a pulmonary artery. FIG. 26A illustrates the profile of the docking station 10 implanted in the pulmonary artery PA. FIG. 26B illustrates the profile of the docking station 10 implanted in the pulmonary artery PA with a schematically illustrated valve 29 installed or deployed in the docking station 10. FIG. 26C illustrates the docking station 10 and valve 29 as depicted in FIG. 22 implanted in the pulmonary artery PA. As mentioned with respect to FIGS. 2A-2E and 3A-3D, the shape of the pulmonary artery may vary significantly along its length. In one exemplary embodiment, the docking station 10 is configured to conform to the varying shape of the pulmonary artery PA. The docking station 10 is illustrated as being positioned below the pulmonary artery bifurcation or branch. However, often the docking station 10 will be positioned such that the end 14 extends into the pulmonary artery bifurcation 210. When it is contemplated that the docking station 10 will extend into the pulmonary artery bifurcation, the docking station 10 can have a blood permeable portion 1400 (e.g., as shown in FIG. 21).

Figure 27:
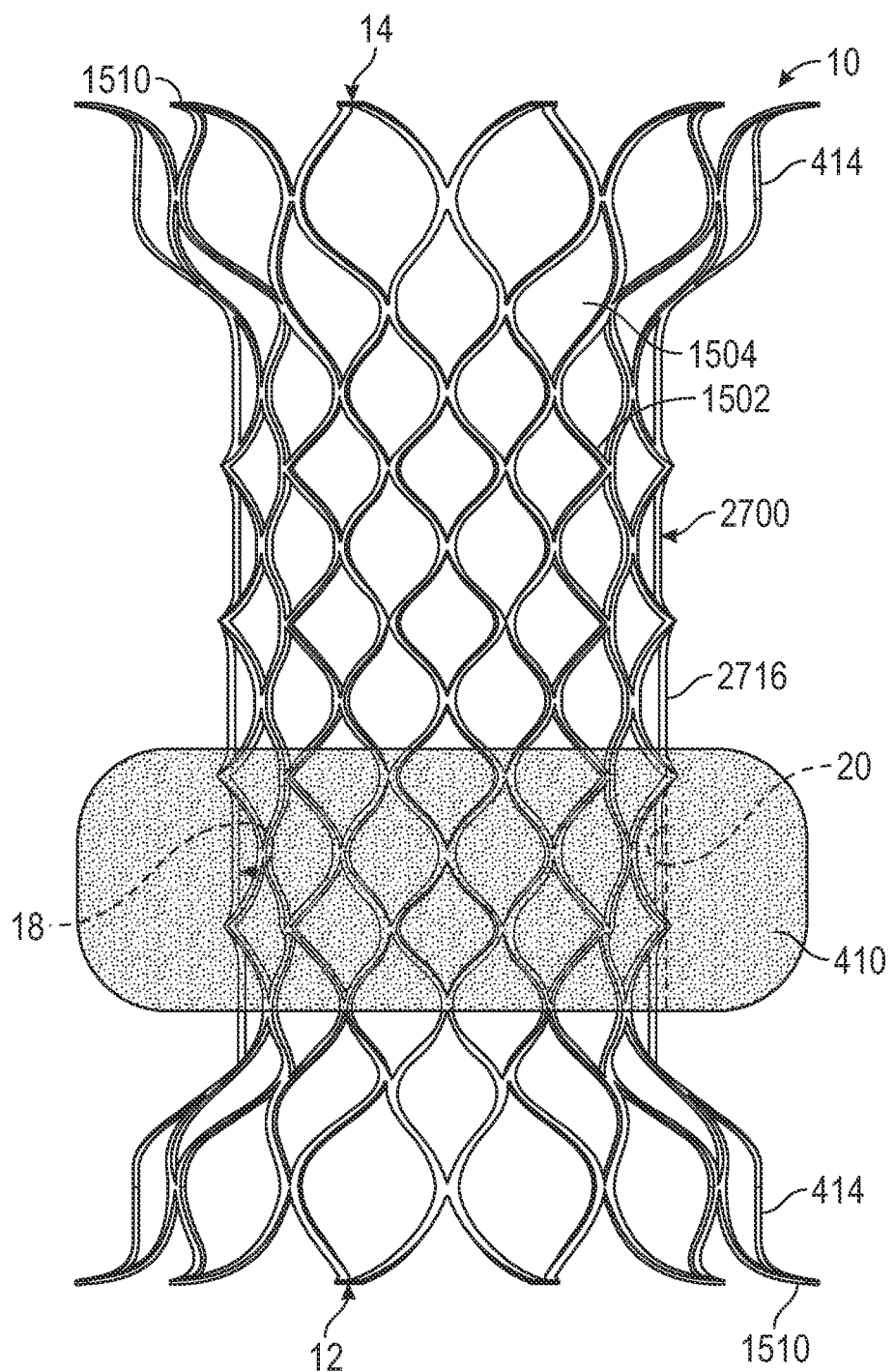
FIG. 27 is a side view of an exemplary embodiment of a docking station.

FIG. 27 illustrates another exemplary embodiment of a docking station 10. The docking station 10 includes a frame 2700 and an external sealing portion 410. The frame 2700 or body can take a wide variety of different forms and FIG. 27 illustrates just one of the many possible configurations. In the example illustrated by FIG. 27 the docking station 10 has a relatively wider proximal inflow end 12 and distal outflow end 14, and an elongated relatively narrower portion 2716. The seat 18 and sealing portion 410 can be provided anywhere along the length of the elongated relatively narrow portion 2716. In the example illustrated by FIG. 27, the frame 2700 of the docking station 10 is preferably a stent comprised of a plurality of metal struts 1502 that form cells 1504. The frame 2700 or portion(s) of the frame can optionally be covered by an impermeable material 21 (e.g., as shown in FIG. 18).

FIG. 27 illustrates the frame 2700 and sealing portion 410 in their unconstrained, expanded condition/configuration or deployed configuration. In this exemplary embodiment, the retaining portions 414 comprise ends 1510 of the metal struts 1502 at the proximal and distal ends 12, 14. The sealing portion 410 can be a separate component that is disposed around the frame 2700 between the retaining portions 414. In the unconstrained condition, the retaining portions 414 extend generally radially outward and may be radially outward of the sealing portion 410.

The docking station 10 illustrated by FIG. 27 may be made from a very resilient or compliant material to accommodate large variations in the anatomy. For example, the docking station may be made from a highly flexible metal (e.g., the frame in the FIG. 27 example) and cloth and/or an open cell foam (e.g., the sealing portion in the FIG. 27 example). An example of a highly resilient metal is nitinol, but other metals and highly resilient or compliant non-metal materials can be used. An example of an open cell foam that can be used is a biocompatible foam, such as a polyurethane foam (e.g., as may be obtained from Biomerix, Rockville, Md.). In one embodiment, a foam forming the sealing portion may also form a valve seat on its inner surface.

Still referring to FIG. 27, the frame 2700 and/or the separate sealing portion 410 may include an optional a band 20 to form an unexpandable or substantially unexpandable valve seat 18. In another exemplary embodiment, the frame 2700 may be configured to be substantially unexpandable in the area of the valve seat 18 without the use of a band 20. The optional band 20 stiffens the frame 2700 and/or sealing portion and makes the valve seat relatively unexpandable.

The optional band 20 can take a wide variety of different forms, can be made from a wide variety of different materials, and can be the same as or similar to bands discussed elsewhere in this disclosure. The band 20 can be made of PET, one or more sutures, fabric, metal, polymer, a biocompatible tape, or other relatively unexpandable materials known in the art that are sufficient to maintain the shape of the valve seat 18 and hold the valve 29 in place. The band can extend about the exterior of the stent, or can be an integral part of it, such as when fabric or another material is interwoven into or through cells of the stent. The band 20 can be narrow, such as the suture band in FIG. 18, or can be wider as illustrate by the dashed line in FIG. 27. In one non-limiting example, the valve seat 18 is between 27-28 mm in diameter, although the diameter of the valve seat should be within the operating range of the particular valve 29 that will be secured within the valve seat 18, and may be different than the foregoing example.

Figure 29:
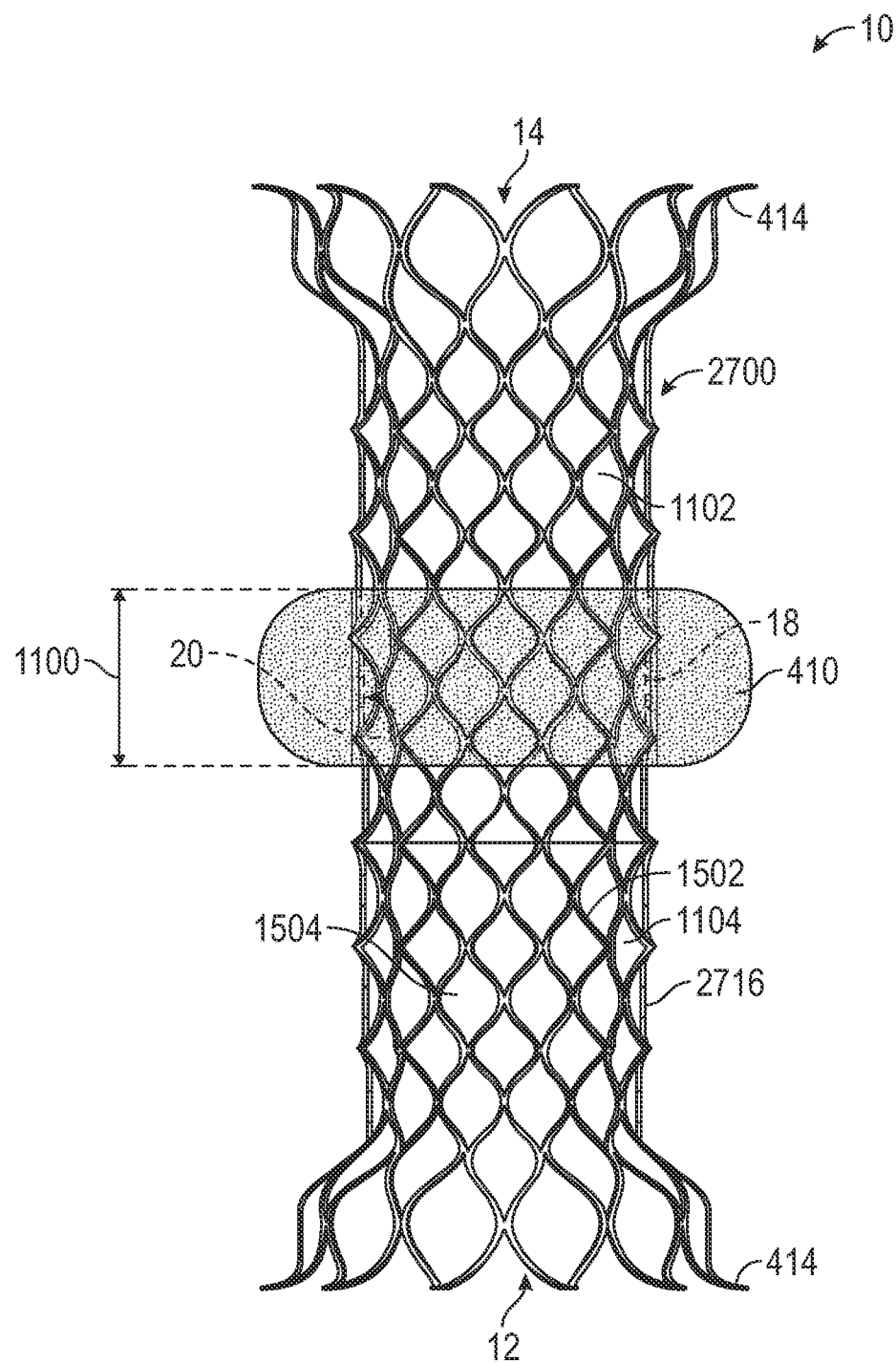
FIG. 29 is a side view of the docking station of FIG. 28 where two parts of the docking station have been telescoped together.

FIGS. 28 and 29 illustrate a modified version of the docking station 10 illustrated by FIG. 27 that is expandable in length. As mentioned above, the length of the pulmonary artery PA and other anatomical structures of the circulatory system may vary greatly from patient to patient. Referring to FIG. 29, in one exemplary embodiment the length of the docking station 10 is adjustable as indicated by arrow 1100. The length may be adjusted in a wide variety of different ways, e.g., it can be adjustable in any of the ways described elsewhere in this disclosure. In the example illustrated by FIGS. 28 and 29, the docking station 10 includes a first half 1102 and a second half 1104. The second half 1104 can be inserted or "telescoped" into the first half 1102. The amount of insertion or "telescoping" sets the length of the docking station 10.

In one exemplary embodiment, the length of the docking station 10 is adjusted in the pulmonary artery PA by first deploying the first half 1102 of the docking station 10 in the pulmonary artery. For example, the first half 1102 may be positioned and expanded such that a distal end 1106 of the first half is aligned with or extends somewhat past the branch of the pulmonary artery. After the first half 1102 is expanded in the pulmonary artery, the compressed second half 1104 is positioned with a distal end 1110 disposed in the proximal end 1108 of the first half 1102. The position of the second half 1104 is selected such that the sealing portion 410 and retaining portion 414 will make contact with the pulmonary artery and set the position of the docking station 10 in the pulmonary artery. Once properly positioned, the second half 1104 is expanded. The distal end of 1110 of the second half 1104 frictionally engages the proximal end 1108 of the first half to secure the two halves 1102, 1104 together. In one embodiment, a lock(s), locking mechanism, suture(s), interlacing, link(s) and/or other attachment device/mechanism may (also or alternatively) be used to secure the two halves together.

In the examples illustrated by FIGS. 28 and 29, the seat 18 and the sealing portion 410 are included on the first half 1102 of the docking station 10. However, in other embodiments the seat 18 and/or the sealing portion(s) 410 can be included on the second half 1104 or in different locations on the first half and/or the second half.

Figure 30:
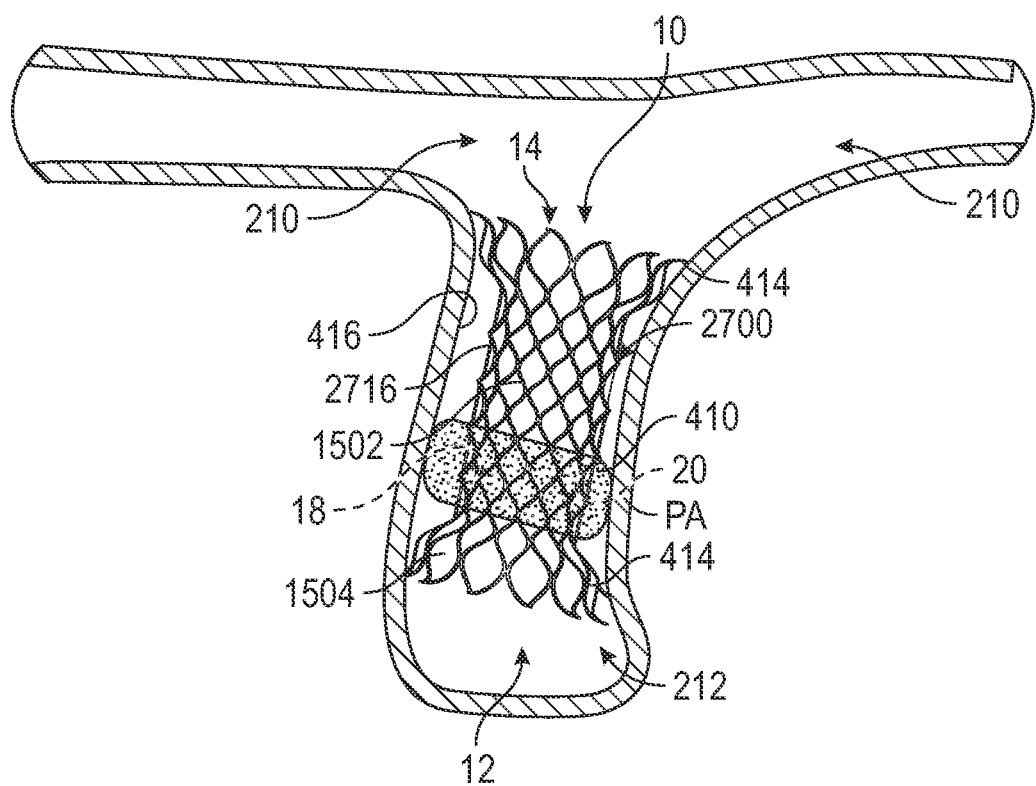
FIG. 30 is a sectional view illustrating a docking station placed in a pulmonary artery.
Figure 31A:
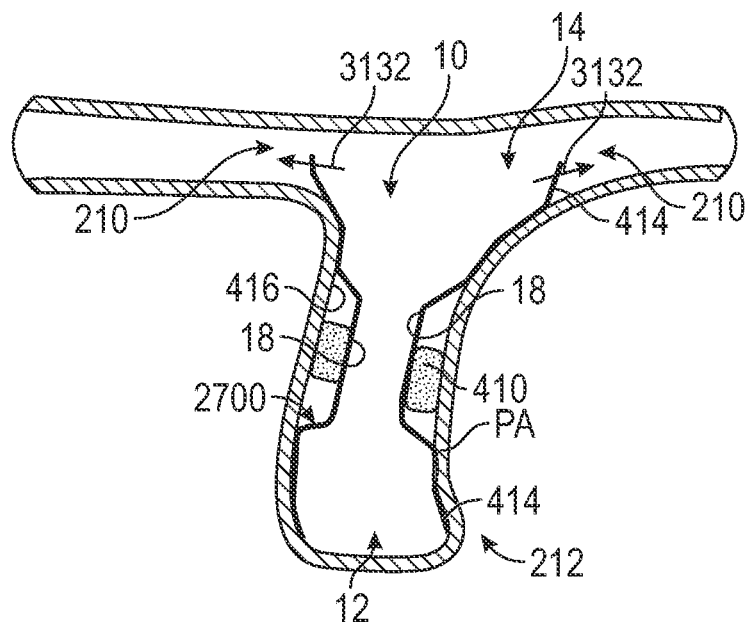
FIG. 31A is a sectional view illustrating a side profile of an exemplary embodiment of a docking station placed in a pulmonary artery.

FIGS. 30 and 31A illustrate the docking station 10 of FIG. 27 of FIGS. 28 and 29 implanted in the circulatory system, such as in the pulmonary artery PA. The sealing portion 410 provides a seal between the docking station 10 and an interior surface 416 of the pulmonary artery PA. In the example of FIGS. 30 and 31A, the sealing portion 410 is an expanding material, such as an expandable open cell foam over the frame 2700. In an exemplary embodiment, the sealing portion 410 coincides or at least overlaps with the valve seat 18. When the sealing portion 410 does not overlap with the valve seat 18, an impermeable material 21 may be provided over a portion of the frame (e.g., from the sealing portion 410 to the valve seat 18 to make the docking station impermeable from the sealing portion 410 to the valve seal 18). Whether the sealing portion 410 overlaps with the valve seat 10 or an impermeable material is provided from the sealing portion 410 to the valve seat 18, all blood flowing in the inflow direction 12 toward the outflow direction 14 is directed to the valve seat 18 (and valve 29 once installed or deployed in the valve seat).

In one exemplary embodiment of a docking station 10, at least the outflow portion 14 of the frame 2700 is relatively open. Referring to FIG. 31A, this allows the docking station 10 to be placed higher in the pulmonary artery without restricting blood flow. For example, the open cells 1504 may extend into the branch or bifurcation of the pulmonary artery and not impede or not significantly impede the flow of blood past the branch. The open cells 1504 allow blood to flow through the frame 1500 as indicated by arrows 3132 in FIG. 31A.

In the example illustrated by FIGS. 30 and 31A, the docking station 10 is retained in the pulmonary artery PA by expanding one or more of the retaining portions 414 radially outward into an area 210, 212 of the pulmonary artery PA where the inside surface 416 also extends outward. For example, the retaining portions 414 may be configured to extend radially outward into the pulmonary bifurcation 210 and/or the opening 212 of the pulmonary artery to the right ventricle RV. In one exemplary embodiment, the docking station 10 can be an adjustable docking station. For example, docking station 10 can be a telescoping docking station as illustrated by FIG. 28 and the first portion 1102 is deployed such that the retaining portions 414 extend radially outward into the pulmonary bifurcation 210). The second portion 1104 can then be positioned in the first portion 1102 such that its retaining portions 414 coincide with the opening of the pulmonary artery or another outwardly extending area of the pulmonary artery. Once in position, the second portion 1104 can be expanded to secure the second section 1104 to the first section 1102 and to secure the second section to the pulmonary artery at the opening 212 or other outwardly extending area.

Figure 31B:
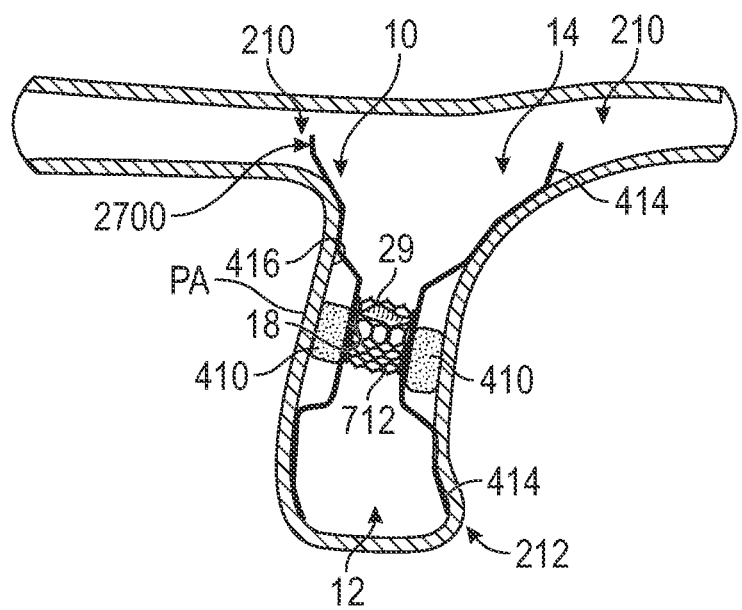
FIG. 31B is a sectional view illustrating a side profile of an exemplary embodiment of a docking station placed in a pulmonary artery and a valve placed in the docking station.

Referring to FIG. 31B, the valve seat 18 provides a supporting surface for installing or deploying a valve 29 in the docking station 10. The valve may be installed or deployed in the valve seat using the steps disclosed here or elsewhere in this disclosure. The anchoring/retaining portions 414 retain the docking station 10 at the implantation or deployed site/position in the circulatory system. After the docking station 10 is deployed, the valve 29 is in a compressed form and can be introduced into the valve seat 18 of the docking station 10. The valve 29 can be expanded in the docking station, such that the valve 29 engages the valve seat 18. The valve 29 can be delivered to the site of the docking station via conventional means, such as by balloon or mechanical expansion or by self-expansion. When the valve 29 is expanded, it nests in the valve seat of the docking station 10.

Figure 32A:
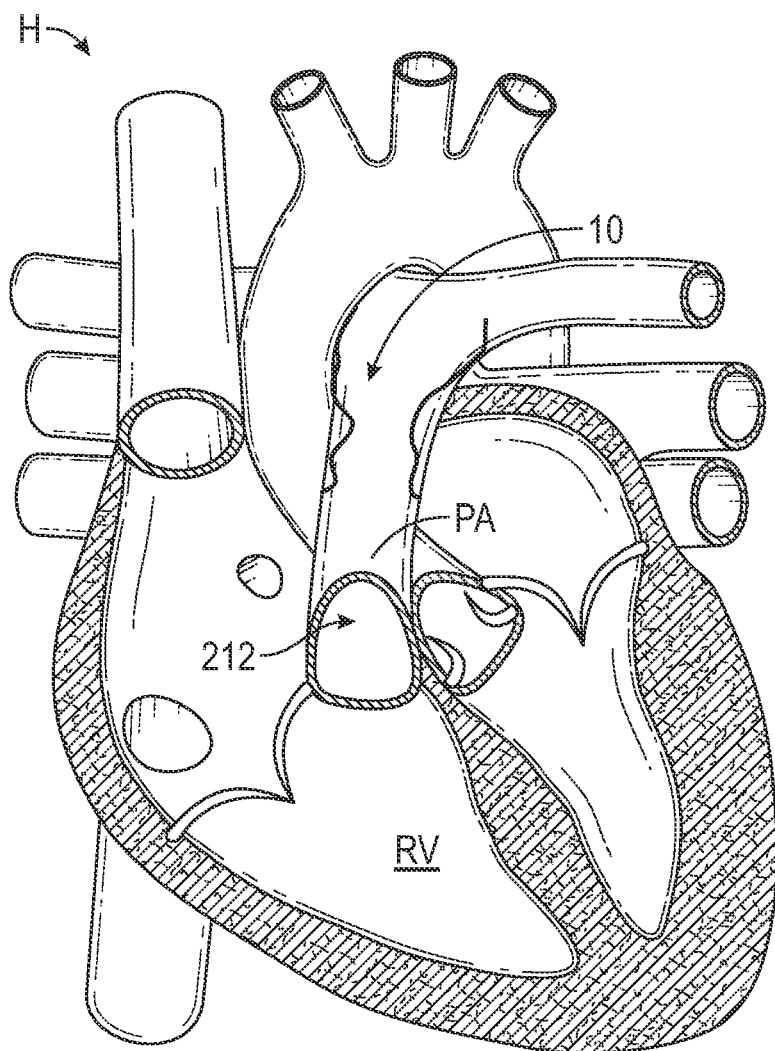
FIG. 32A is a cutaway view of the human heart in a systolic phase with a docking station and deployed in a pulmonary artery.
Figure 32B:
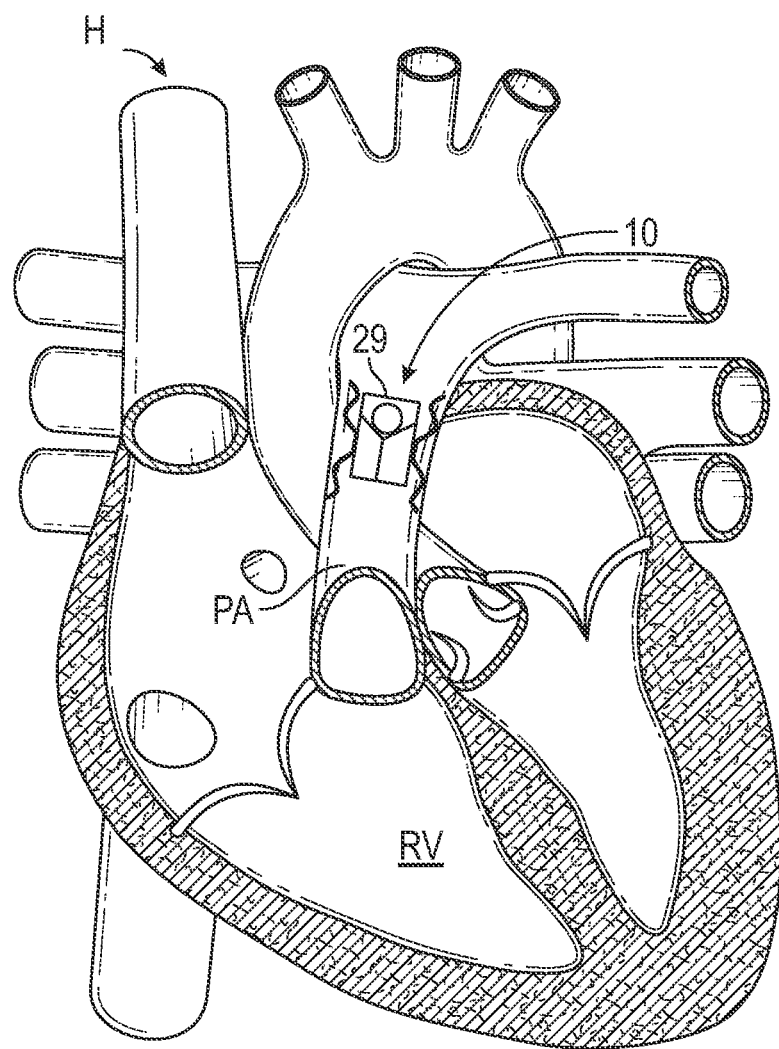
FIG. 32B is a cutaway view of the human heart in a systolic phase with a docking station and transcatheter heart valve deployed in a pulmonary artery.
Figure 33A:
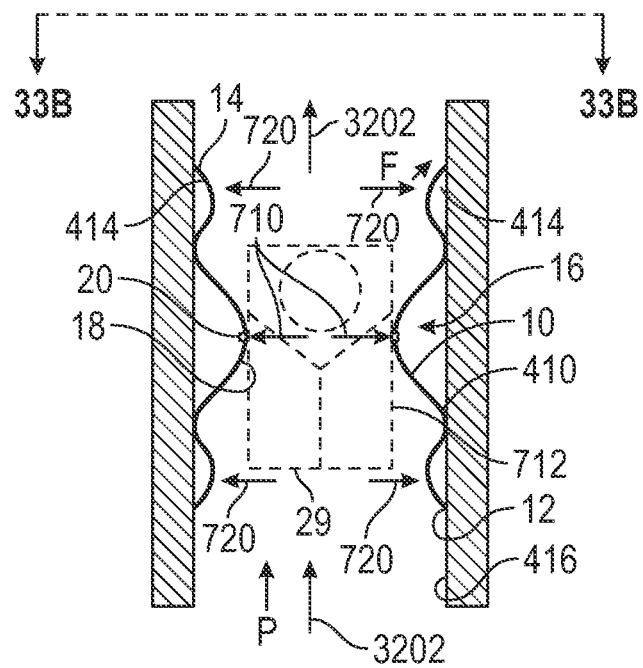
FIG. 33A is an enlarged schematic illustration of the docking station and transcatheter heart valve of FIG. 32B when the heart is in the systolic phase.
Figure 33B:
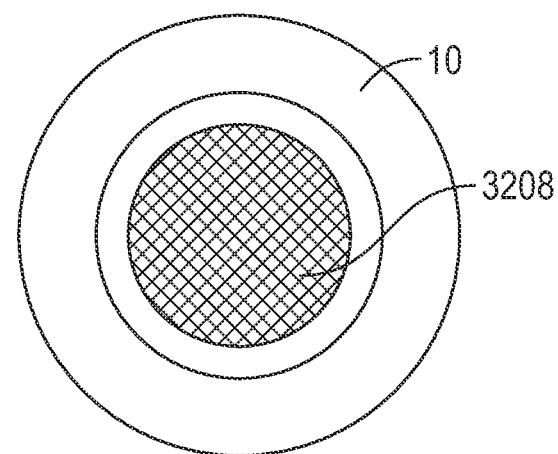
FIG. 33B is a view taken in the direction indicated by lines 33B-33B in FIG. 33A.

Referring to FIG. 32A, the docking station illustrated by FIG. 18 is deployed in the pulmonary artery PA of a heart H. FIG. 32B illustrates a generically illustrated valve 29 deployed in the docking station 10 illustrated by FIG. 32A. In FIGS. 32A and 32B, the heart is in the systolic phase. FIG. 33A is an enlarged representation of the docking station 10 and valve 29 in the pulmonary artery 29 of FIG. 32B. When the heart is in the systolic phase, the valve 29 opens. Blood flows from the right ventricle RV and through the pulmonary artery PA, docking station 10, and valve 29 as indicated by arrows 3202. FIG. 33B illustrates space 3208 that represents the valve 29 being open when the heart is in the systolic phase. FIG. 33B does not show the interface between the docking station 10 and the pulmonary artery to simplify the drawing. The cross-hatching in FIG. 33B illustrates blood flow through the open valve. In an exemplary embodiment, blood is prevented from flowing between the pulmonary artery PA and the docking station 10 by the seal 410 and blood is prevented from flowing between the docking station 10 and the valve 29 by seating of the valve 29 in the seat 18 of the docking station 10. In this example, blood is substantially only or only able to flow through the valve 29 when the heart is in the systolic phase.

Figure 34:
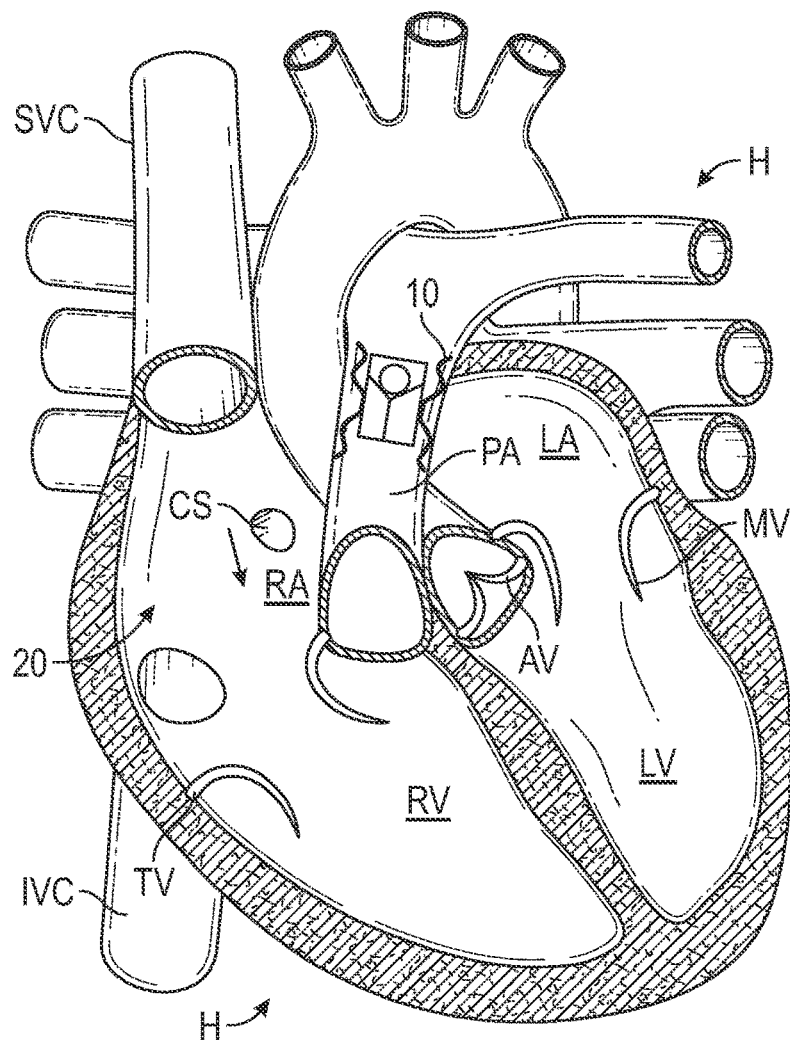
FIG. 34 is a cutaway view of the human heart, docking station, and transcatheter heart valve deployed in the pulmonary artery illustrated by FIG. 32B when the heart is in the diastolic phase.
Figures 35A, 35B:
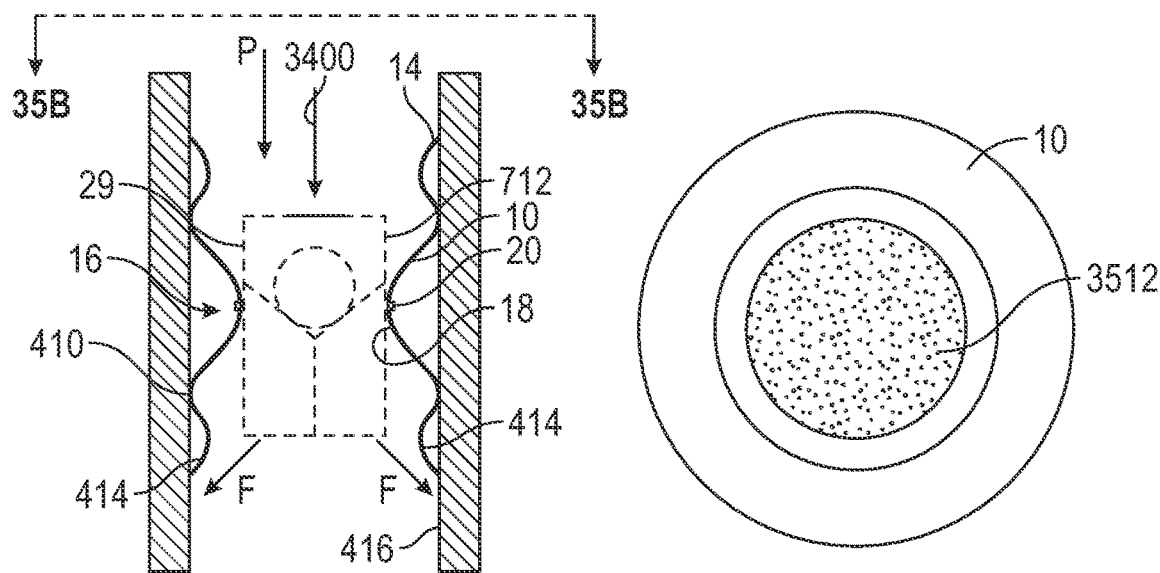
FIG. 35A is an enlarged schematic illustration of the docking station and transcatheter heart valve of FIG. 34 when the heart is in the diastolic phase.
FIG. 35B is a view taken in the direction indicated by lines 35B-35B in FIG. 35A.

FIG. 34 illustrates the valve 29, docking station 10 and heart H illustrated by FIG. 32B, when the heart is in the diastolic phase. Referring to FIG. 34, when the heart is in the diastolic phase, the valve 29 closes. FIG. 35A is an enlarged representation of the docking station 10 and valve 29 in the pulmonary artery 29 of FIG. 34. Blood flow in the pulmonary artery PA above the valve 29 (i.e. in the pulmonary branch 210) is blocked by the valve 29 being closed and blocking blood flow as indicated by arrow 3400. The solid area 3512 in FIG. 35B represents the valve 29 being closed when the heart is in the diastolic phase.

Referring to FIG. 33A, the radially outward force 720 of the anchoring/retaining portions 414 to the inside surface 416 is substantially smaller than the radially outward force 710 applied by the valve 29 to the valve seat 18. For example, the radially outward sealing force 720 can be less than ½ the radially outward force 710 applied by the valve, less than ⅓ the radially outward force 710 applied by the valve, less than ¼ the radially outward force 710 applied by the valve, less than ⅛, or even less than ¹/₁₀ the radially outward force 710 applied by the valve.

Referring to FIGS. 33A and 35A, in one exemplary embodiment the radially outward force 720 of the retaining portions 414 is not sufficient by itself to retain the position of the valve 29 and docking station 10 in the circulatory system. Rather, the pressure of the blood 3208 is used to enhance the retention of the retaining portions 414 to the inside surface 416. Referring again to FIG. 33A, when the heart is in the systolic phase, the valve 29 is open and blood flows through the valve as indicated by arrows 3202. Since the valve 29 is open and blood flows through the valve 29, the pressure P applied to the docking station 10 and valve 29 by the blood is low as indicated by the small P and arrow in FIG. 33A. Even though small, the pressure P forces the docking station and its upper retaining portions 414 against the surface 416 generally in the direction indicated by arrow F (the small F represents a relatively low force). This blood flow assisted force F applied by the retaining portions F to the surface 416 prevents the docking station 10 and valve 29 from moving in the direction 3302 of blood flow in the systolic phase of the heart H.

Referring to FIG. 35A, when the heart is in the diastolic phase, the valve 29 is closed and blood flow is blocked as indicated by arrow 3400. Since the valve 29 is closed and the valve 29 and docking station 10 block the flow of blood, the pressure P applied to the docking station 10 and valve 29 by the blood is high as indicated by the large arrow P in FIG. 35A. This large pressure P forces the lower retaining portions 414 against the surface 416 generally in the direction indicated by the large arrows F (the large F represents a relatively larger force). This blood flow assisted force F applied by the retaining portions F to the surface 416 prevents the docking station 10 and valve 29 from moving in the direction indicated by arrow 3400.

Referring to FIGS. 33A and 35A, since the force applied by the upper and lower retaining portions 414 is determined by amount of pressure applied to the valve 29 and docking station 10 by the blood, the force applied to the surface 416 is automatically proportioned. That is, the upper retaining portions are less forcefully pressed against the surface 416 when the heart is in the systolic phase than the lower retaining portions are pressed against the surface 416 when the heart is in the diastolic phase. This is because the pressure against the open valve 29 and docking station 10 in the systolic phase is less than the pressure against the closed valve and docking station in the diastolic phase.

Figure 36A:
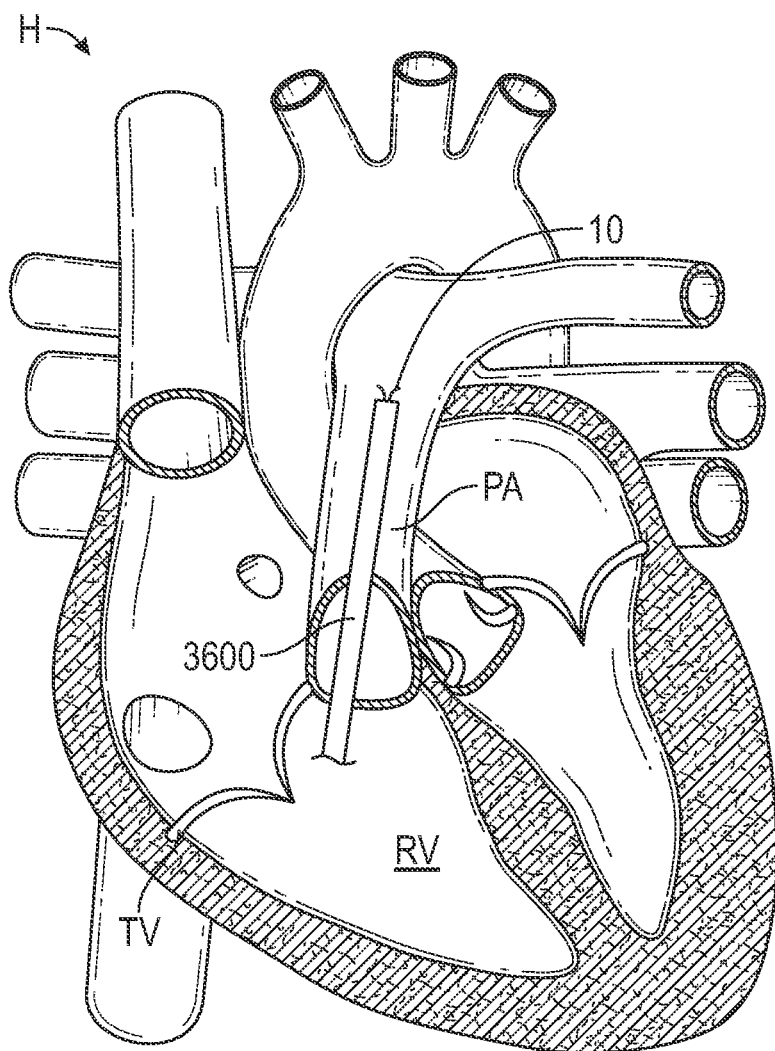
FIG. 36A is a cutaway view of the human heart in a systolic phase with a docking station being deployed in a pulmonary artery.

Methods of treating a patient (e.g., methods of treating heart valve dysfunction/regurgitation/etc.) may include a variety of steps, including steps associated with introducing and deploying a docking station in a desired location/ treatment area and introducing and deploying a valve in the docking station. For example, FIG. 36A illustrates the docking station illustrated by FIG. 18 being deployed by a catheter 3600. The docking station 10 can be positioned and deployed in a wide variety of different ways. Access can be gained through the femoral vein or access can be percutaneous. Generally, any vascular path that leads to the pulmonary artery may be used. In one exemplary embodiment, a guidewire followed by a catheter 3600 is advanced to the pulmonary artery PA by way of the femoral vein, inferior vena cava, tricuspid valve, and right ventricle RV. The docking station 10 can be placed in the right ventricular outflow tract/pulmonary artery PA to create an artificial conduit and landing zone for a valve (e.g., a transcatheter heart valve) 29.

Figure 36B:
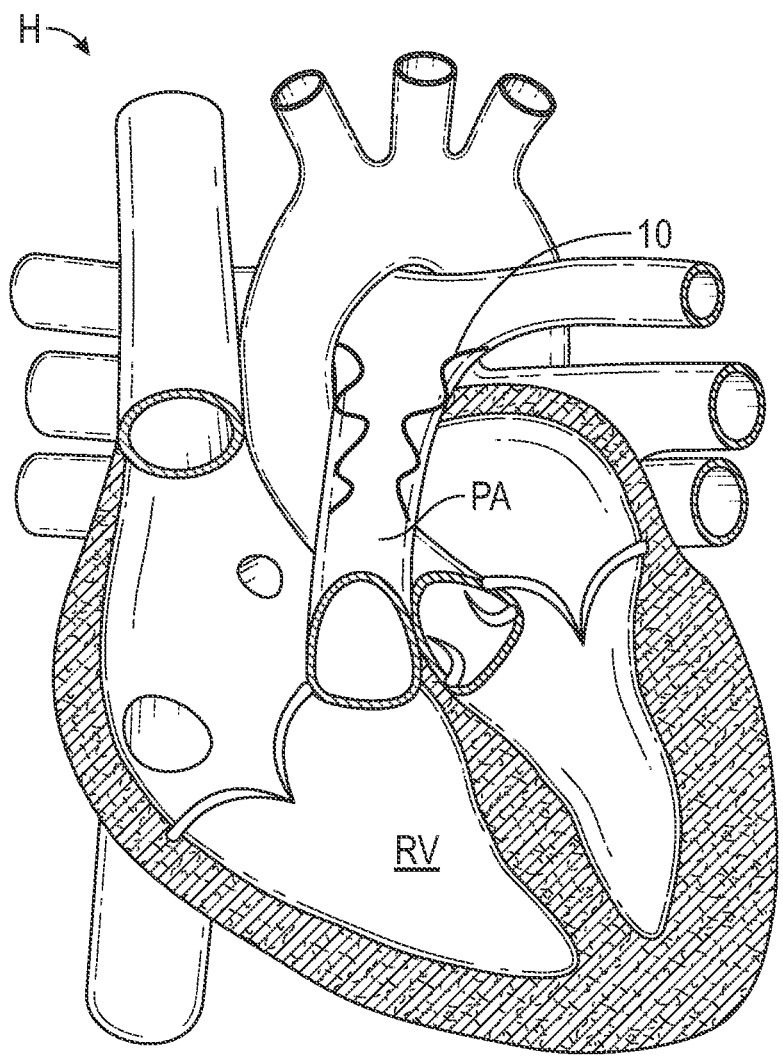
FIG. 36B is a cutaway view of the human heart in a systolic phase with a docking station deployed in a pulmonary artery.
Figure 36C:
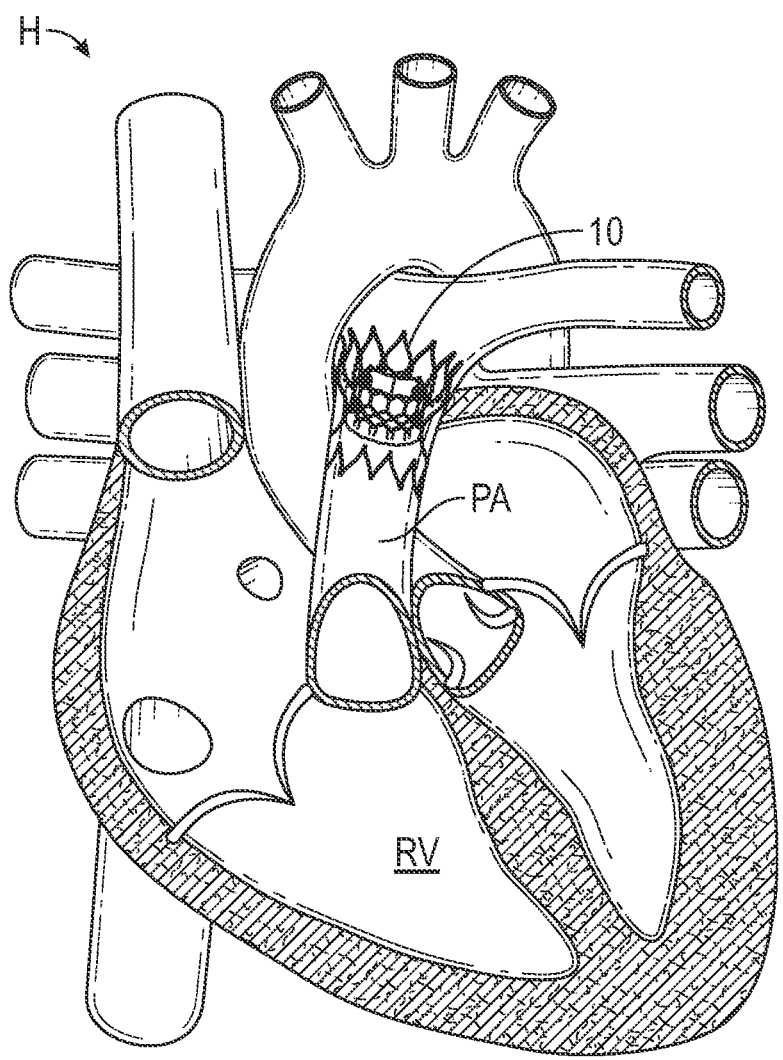
FIG. 36C is a cutaway view of the human heart in a systolic phase with a docking station and transcatheter heart valve deployed in a pulmonary artery.
Figure 37A:
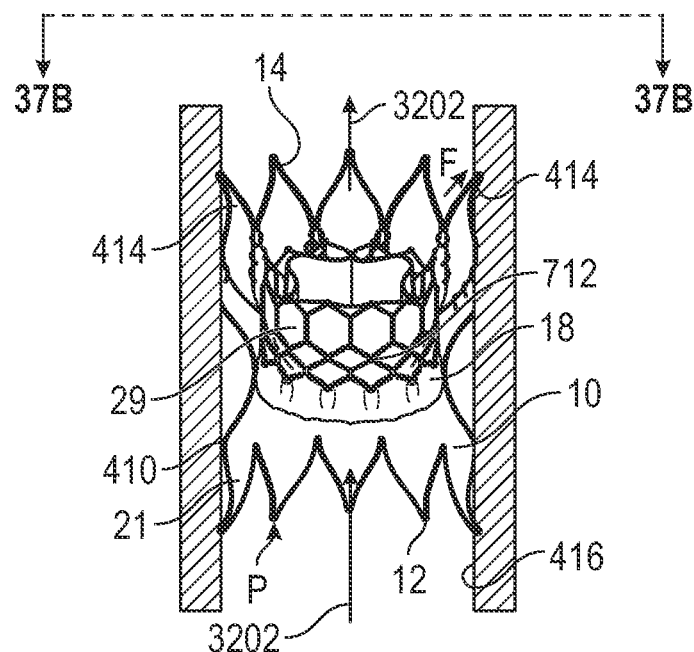
FIG. 37A is an enlarged schematic illustration of the docking station and transcatheter heart valve of FIG. 36C when the heart is in the systolic phase.
Figure 37B:
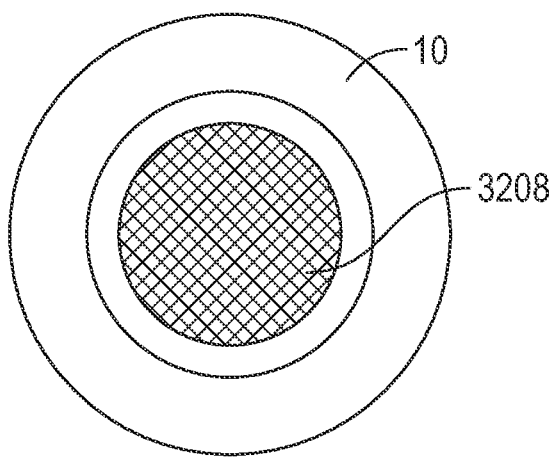
FIG. 37B is a view taken in the direction indicated by lines 37B-37B in FIG. 37A.

Referring to FIG. 36B, the docking station illustrated by FIG. 18 is deployed in the pulmonary artery (PA) of a heart H. FIG. 36C illustrates a valve 29 deployed in the docking station 10 illustrated by FIG. 32A. In the example illustrated by FIGS. 36C, 37A, 38, 39A, and 39B, the valve 29 is depicted as a SAPIEN 3 THV provided by Edwards Lifesciences; however, a variety of other valves may also be used. In FIGS. 36A-36C, the heart is in the systolic phase. FIG. 37A is an enlarged representation of the docking station 10 and valve 29 in the pulmonary artery 29 of FIG. 36C. When the heart is in the systolic phase, the valve (e.g., Sapien 3 valve) is open. Blood flows from the right ventricle RV and through the pulmonary artery PA, docking station 10, and valve as indicated by arrows 3202. FIG. 37B illustrates space 3208 that represents the valve being open when the heart is in the systolic phase. FIG. 37B does not show the interface between the docking station 10 and the pulmonary artery to simplify the drawing. The cross-hatching in FIG. 37B illustrates blood flow through the valve. In an exemplary embodiment, blood is prevented from flowing between the pulmonary artery PA and the docking station 10 by the seal 410 and blood is prevented from flowing between the docking station 10 and the valve by seating of the valve in the seat 18 of the docking station 10. In this example, blood is substantially only or only able to flow through the valve when the heart is in the systolic phase.

Figure 38:
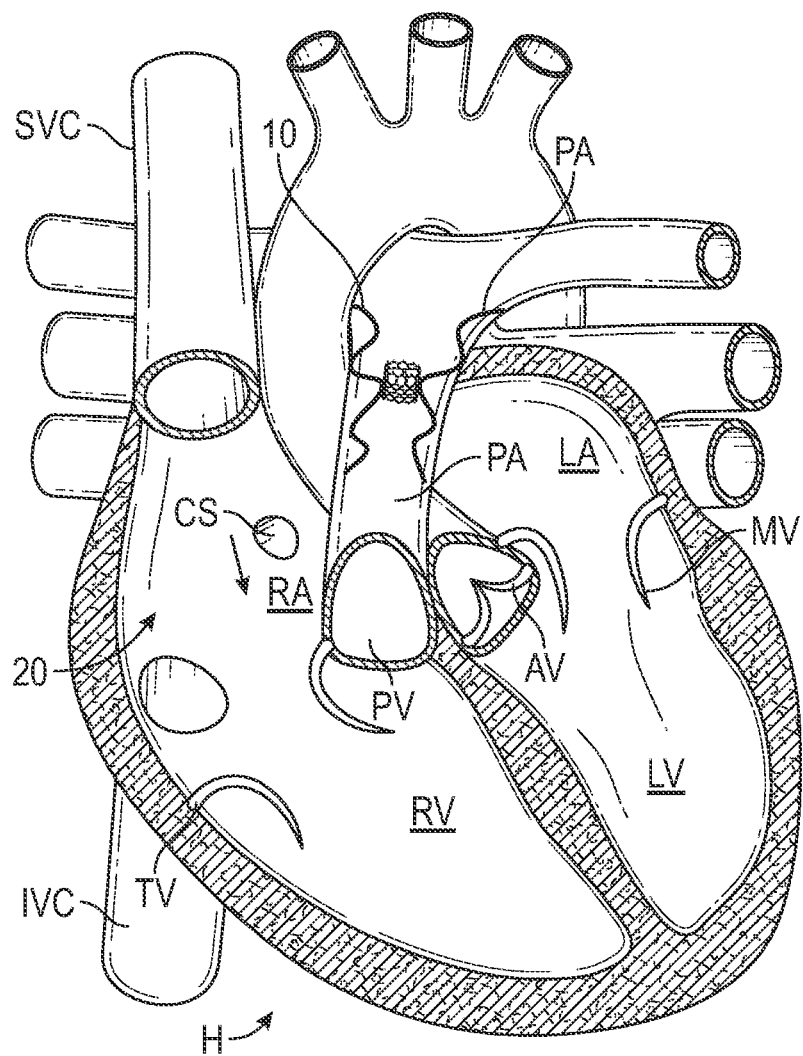
FIG. 38 is a cutaway view of the human heart, docking station, and transcatheter heart valve deployed in the pulmonary artery illustrated by FIG. 36C when the heart is in the diastolic phase.
Figure 39A:
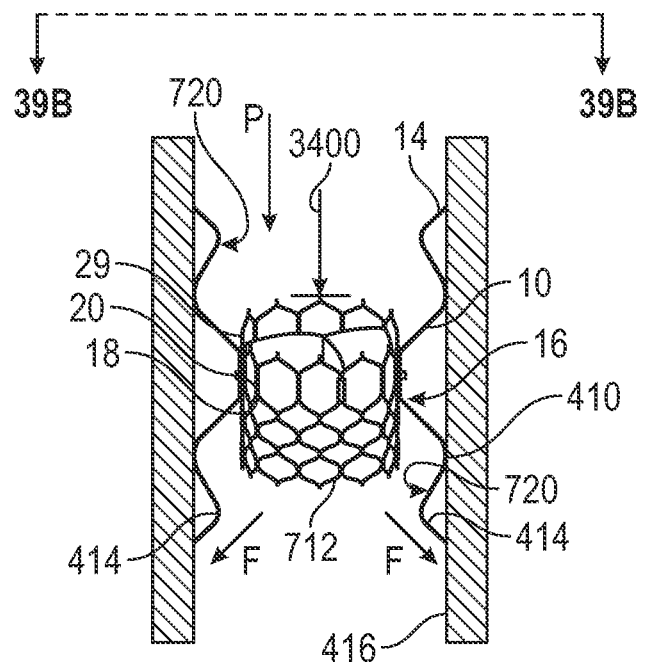
FIG. 39A is an enlarged schematic illustration of the docking station and transcatheter heart valve of FIG. 38 when the heart is in the diastolic phase.
Figure 39B:
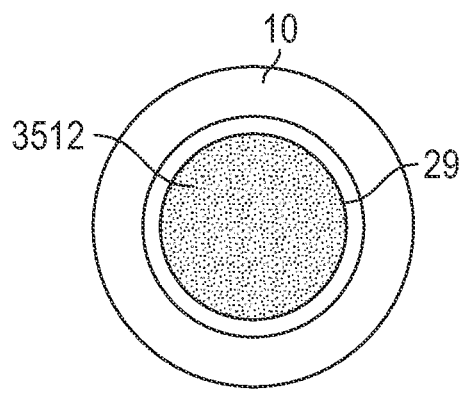
FIG. 39B is a view taken in the direction indicated by lines 39B-39B in FIG. 39A.

FIG. 38 illustrates the valve 29, docking station 10 and heart H illustrated by FIG. 36C, when the heart is in the diastolic phase. Referring to FIG. 38, when the heart is in the diastolic phase, the valve 29 closes. FIG. 39A is an enlarged representation of the docking station 10 and valve (e.g., Sapien 3 valve) in the pulmonary artery 29 of FIG. 38. Blood flow in the pulmonary artery PA above the valve 29 (i.e. in the pulmonary branch 210) is blocked by the valve 29 being closed and blocking blood flow as indicated by arrow 3400. The solid area 3512 in FIG. 39B represents the valve 29 being closed when the heart is in the diastolic phase.

Referring to FIG. 39A, the radially outward force 720 of the anchoring/retaining portions 414 to the inside surface 416 is substantially smaller than the radially outward force 710 applied by the valve (e.g., Sapien 3 valve) to the valve seat 18. For example, the radially outward sealing force 720 can be less than ½ the radially outward force 710 applied by the valve, less than ⅓ the radially outward force 710 applied by the valve, less than ¼ the radially outward force 710 applied by the valve, less than ⅛, or even less than 1/10 the radially outward force 710 applied by the valve. The 29 mm size Sapien 3 valve typically applies radially outward force 710 of about 42 Newtons. In one embodiment, the radially outward force of deployed docking stations described herein or one or more portions of a deployed docking stations can be between about 4 to 16 Newtons, though other forces are also possible.

Figure 40A:
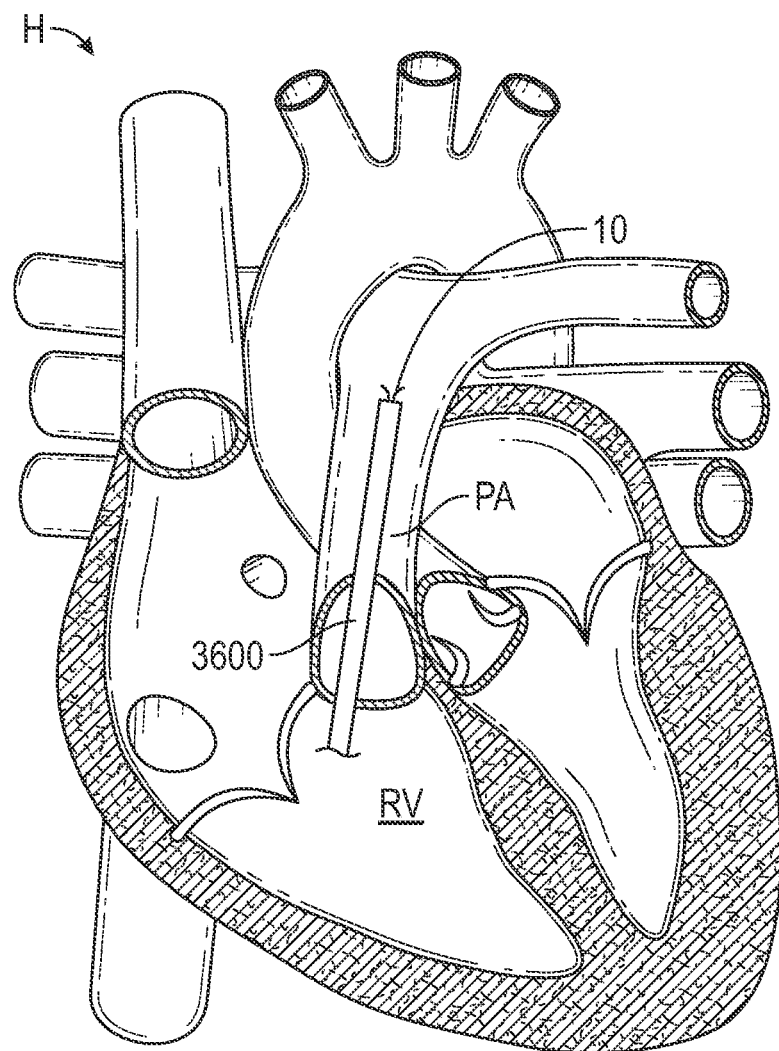
FIG. 40A is a cutaway view of the human heart in a systolic phase with a docking station being deployed in a pulmonary artery.
Figure 40B:
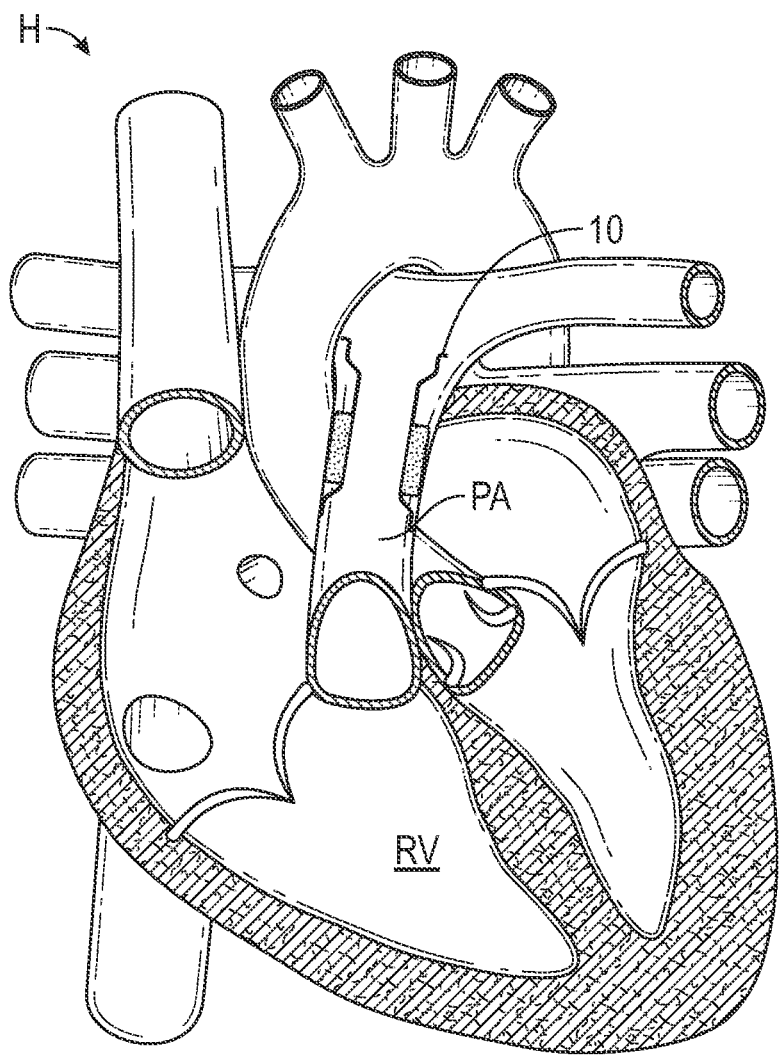
FIG. 40B is a cutaway view of the human heart in a systolic phase with a docking station deployed in the pulmonary artery.
Figure 40C:
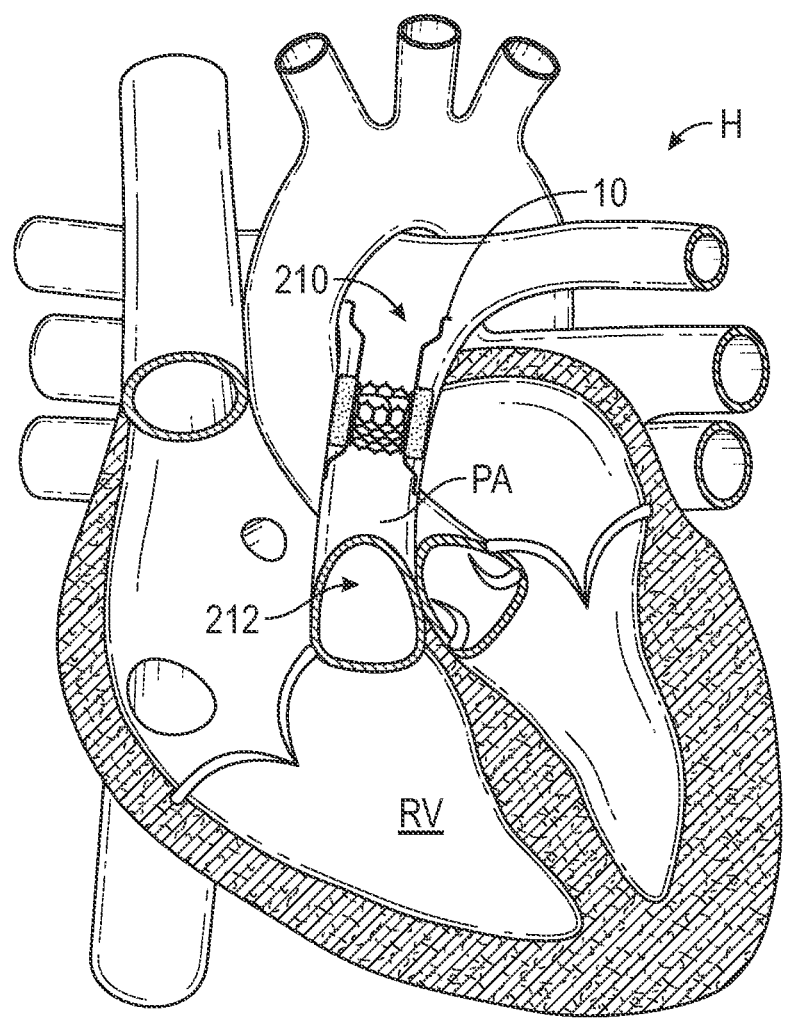
FIG. 40C is a cutaway view of the human heart in a systolic phase with the docking station and a transcatheter heart valve deployed in the pulmonary artery.
Figure 41A:
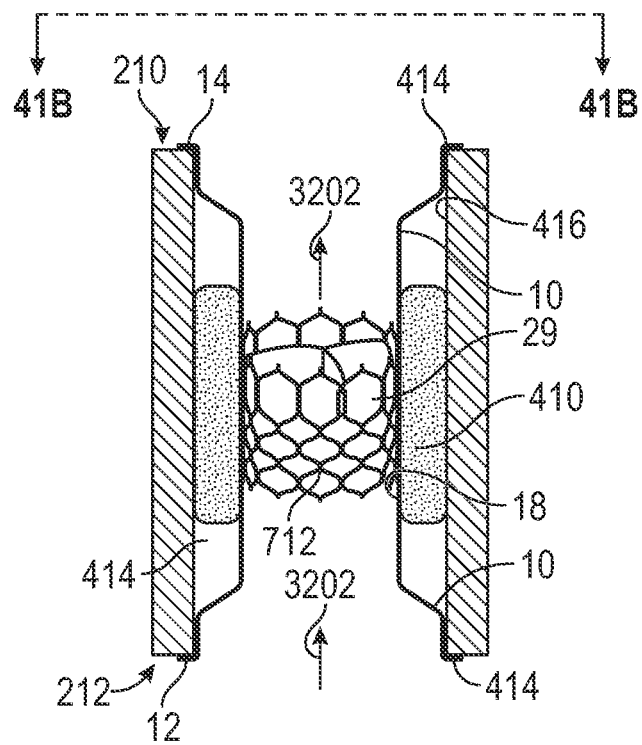
FIG. 41A is an enlarged schematic illustration of the docking station and transcatheter heart valve of FIG. 40C when the heart is in the systolic phase.
Figure 41B:
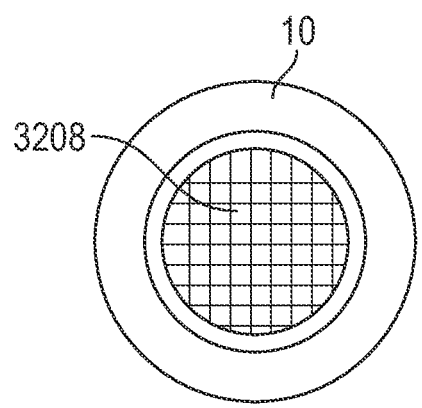
FIG. 41B is a view taken in the direction indicated by lines 41B-41B in FIG. 41A.

FIG. 40A illustrates the docking station illustrated by FIG. 27 or 28 being deployed by a catheter 3600. Referring to FIG. 40B, the docking station illustrated by FIG. 27 or 28 is deployed in the pulmonary artery PA of a heart H. FIG. 40C illustrates a valve 29 deployed in the docking station 10 illustrated by FIG. 40A. In the example illustrated by FIGS. 36C, 37A, 38, 39A, and 39B, the valve 29 is a SAPIEN 3 THV provided by Edwards Lifesciences, though a variety of different valves may be used. In FIGS. 40A-40C, the heart is in the systolic phase. FIG. 41A is an enlarged representation of the docking station 10 and valve 29 in the pulmonary artery 29 of FIG. 40C. When the heart is in the systolic phase, blood flows from the right ventricle RV and through the pulmonary artery PA, docking station 10, and valve 29 as indicated by arrows 3202. FIG. 41B illustrates space 3208 that represents the valve 29 being open when the heart is in the systolic phase. FIG. 41B does not show the interface between the docking station 10 and the pulmonary artery to simplify the drawing. The cross-hatching in FIG. 41B illustrates blood flow through the valve 29. In an exemplary embodiment, blood is prevented from flowing between the pulmonary artery PA and the docking station 10 by the seal 410 and blood is prevented from flowing between the docking station 10 and the valve 29 by seating of the valve in the seat 18 of the docking station 10. In this example, blood is substantially only or only able to flow through the valve when the heart is in the systolic phase.

Figure 42:
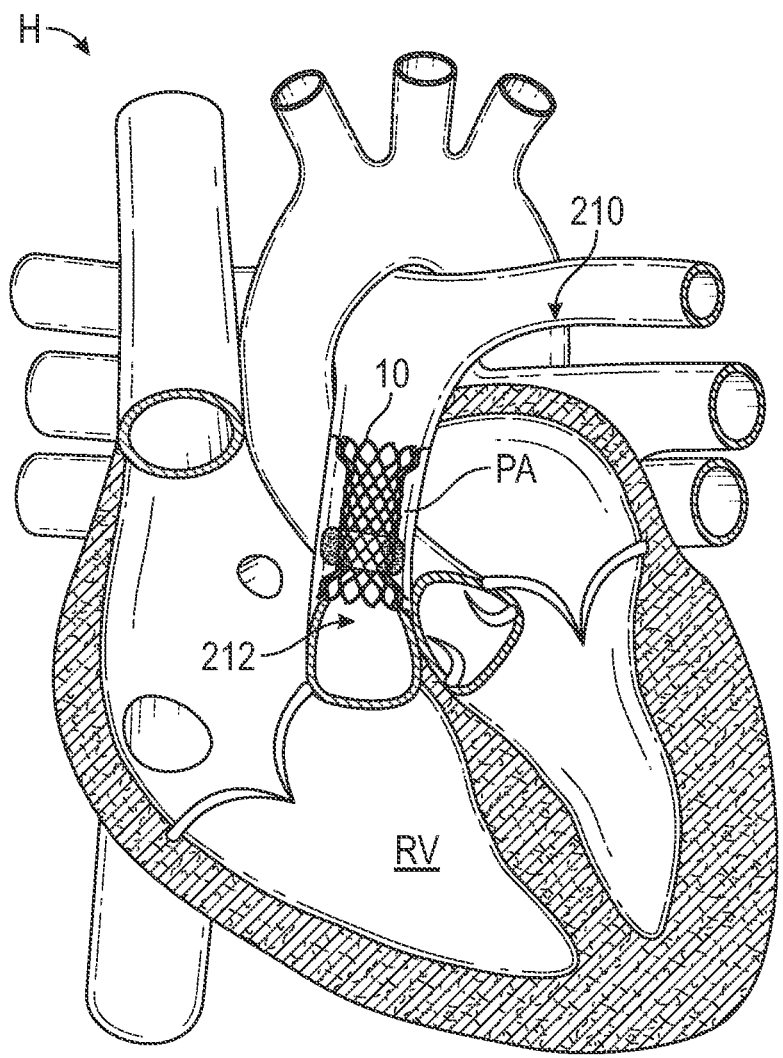
FIG. 42 is a cutaway view of the human heart, docking station, and transcatheter heart valve deployed in the pulmonary artery illustrated by FIG. 40C when the heart is in the diastolic phase.
Figure 43A:
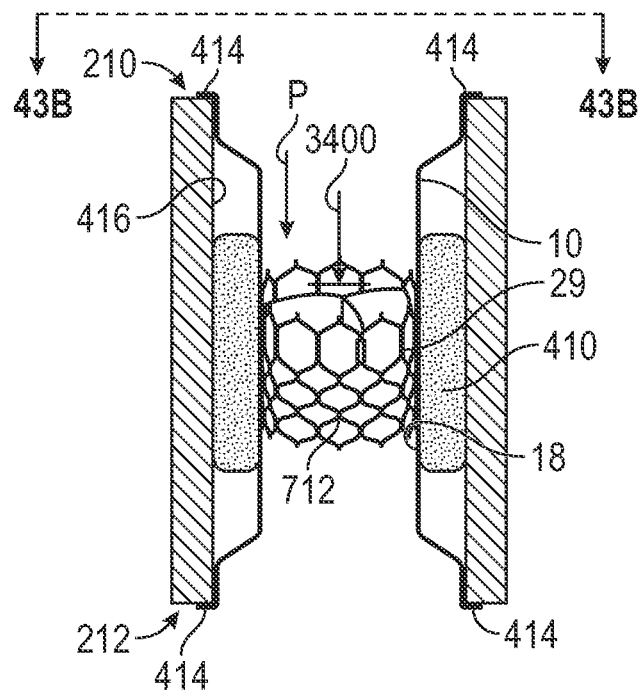
FIG. 43A is an enlarged schematic illustration of the docking station and transcatheter heart valve of FIG. 42 when the heart is in the diastolic phase.
Figure 43B:
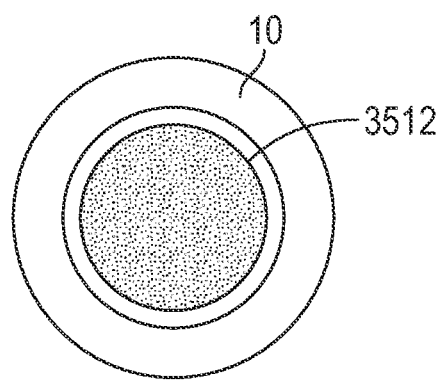
FIG. 43B is a view taken in the direction indicated by lines 43B-43B in FIG. 43A.

FIG. 42 illustrates the valve 29, docking station 10 and heart H illustrated by FIG. 40C, when the heart is in the diastolic phase. Referring to FIG. 42, when the heart is in the diastolic phase, the valve 29 closes. FIG. 43A is an enlarged representation of the docking station 10 and valve 29 in the pulmonary artery 29 of FIG. 42. Blood flow in the pulmonary artery PA above the valve 29 (i.e. in the pulmonary branch 210) is blocked by the valve 29 being closed and blocking blood flow as indicated by arrow 3400. The solid area 3512 in FIG. 43B represents the valve 29 being closed when the heart is in the diastolic phase.

Referring to FIG. 43A, the docking station 10 is retained in the pulmonary artery PA by expanding one or more of the retaining/anchoring portions 414 radially outward into an area 210, 212 of the pulmonary artery PA where the inside surface 416 also extends outward. For example, the retaining portions 414 may be configured to extend radially outward into the pulmonary bifurcation 210 and/or the opening 212 of the pulmonary artery to the right ventricle RV. In one exemplary embodiment, the docking station 10 can be an adjustable and/or multiple component docking station. For example, docking station 10 can be a telescoping docking station as illustrated by FIG. 28 and the first portion 1102 can be deployed such that the retaining portions 414 extend radially outward into the pulmonary bifurcation 210 and the second portion 1104 can be positioned in the first portion 1102 such that its retaining portions 414 coincide with the opening 212 of the pulmonary artery. The extension of the retaining portions 414 into the areas 210, 212 set the position of the docking station 10 in the pulmonary artery PA and help prevent the pressure P shown in FIG. 43A from moving the docking station.

The valve 29 used with the docking station 10 can take a wide variety of different forms. In one exemplary embodiment, the valve 29 is configured to be implanted via a catheter in the heart H. For example, the valve 29 may be expandable and collapsible to facilitate transcatheter application in a heart. However, in other embodiments, the valve 29 may be configured for surgical application. Similarly, the docking stations described herein may be placed using transcatheter application/placement or surgical application/placement.

Figure 44:
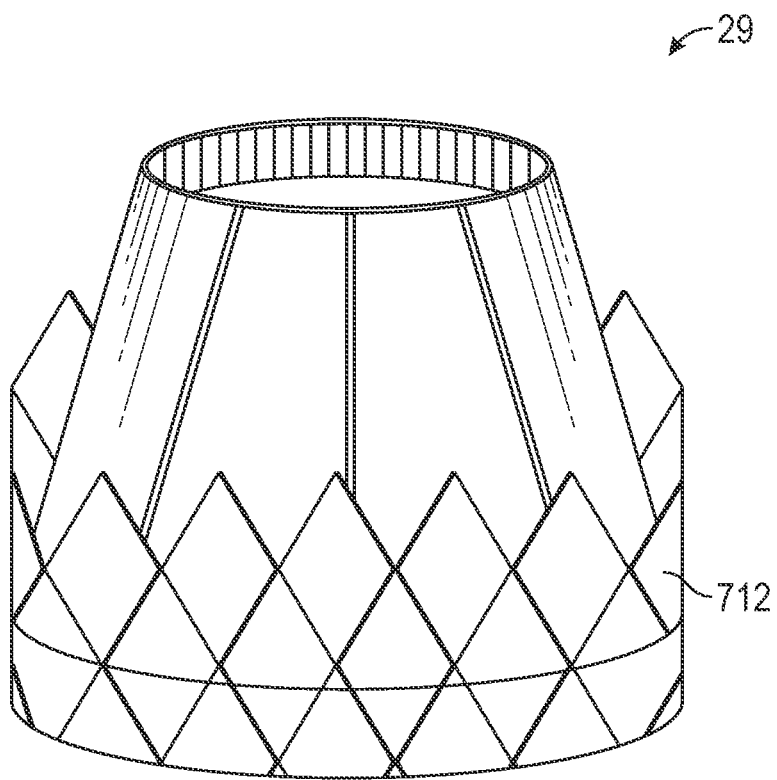
FIGS. 44-47, and 48A-48C illustrate examples of valve types that may be deployed in a docking station, e.g., one of the docking stations described or depicted herein.
Figure 45:
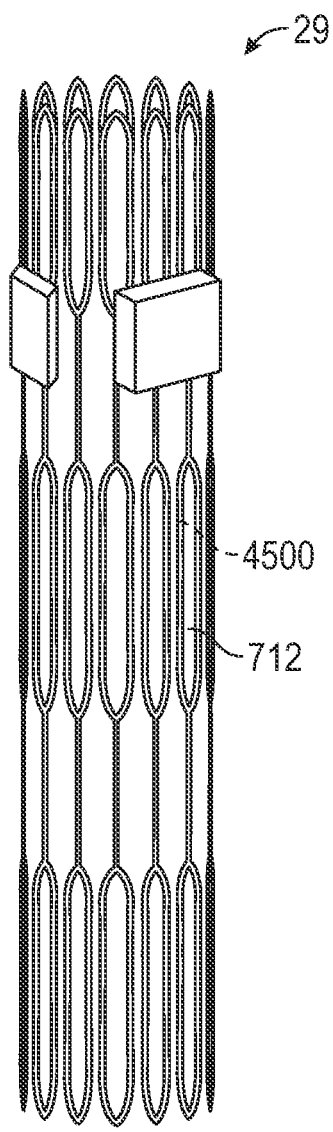
Figure 46:
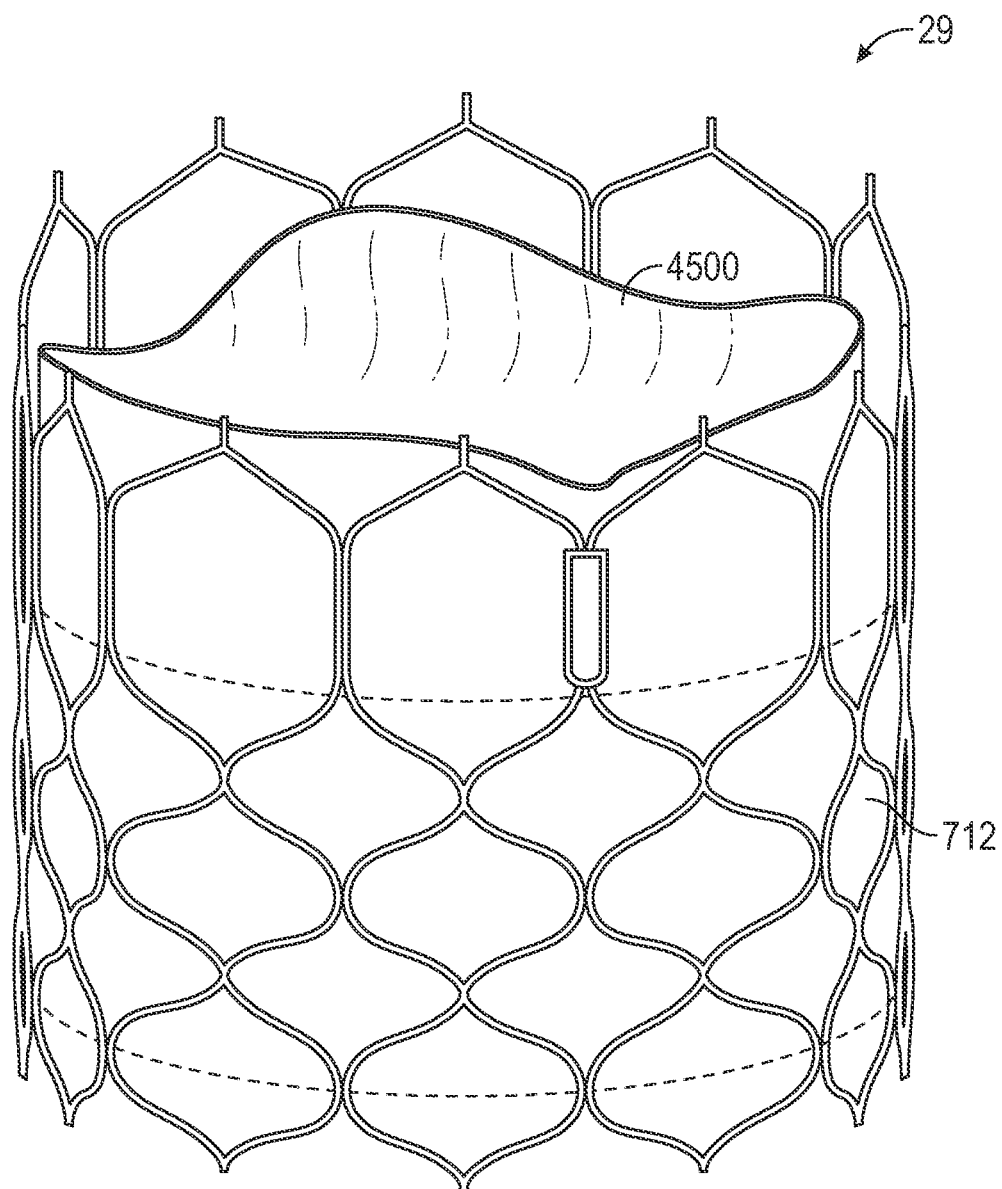
Figure 47:
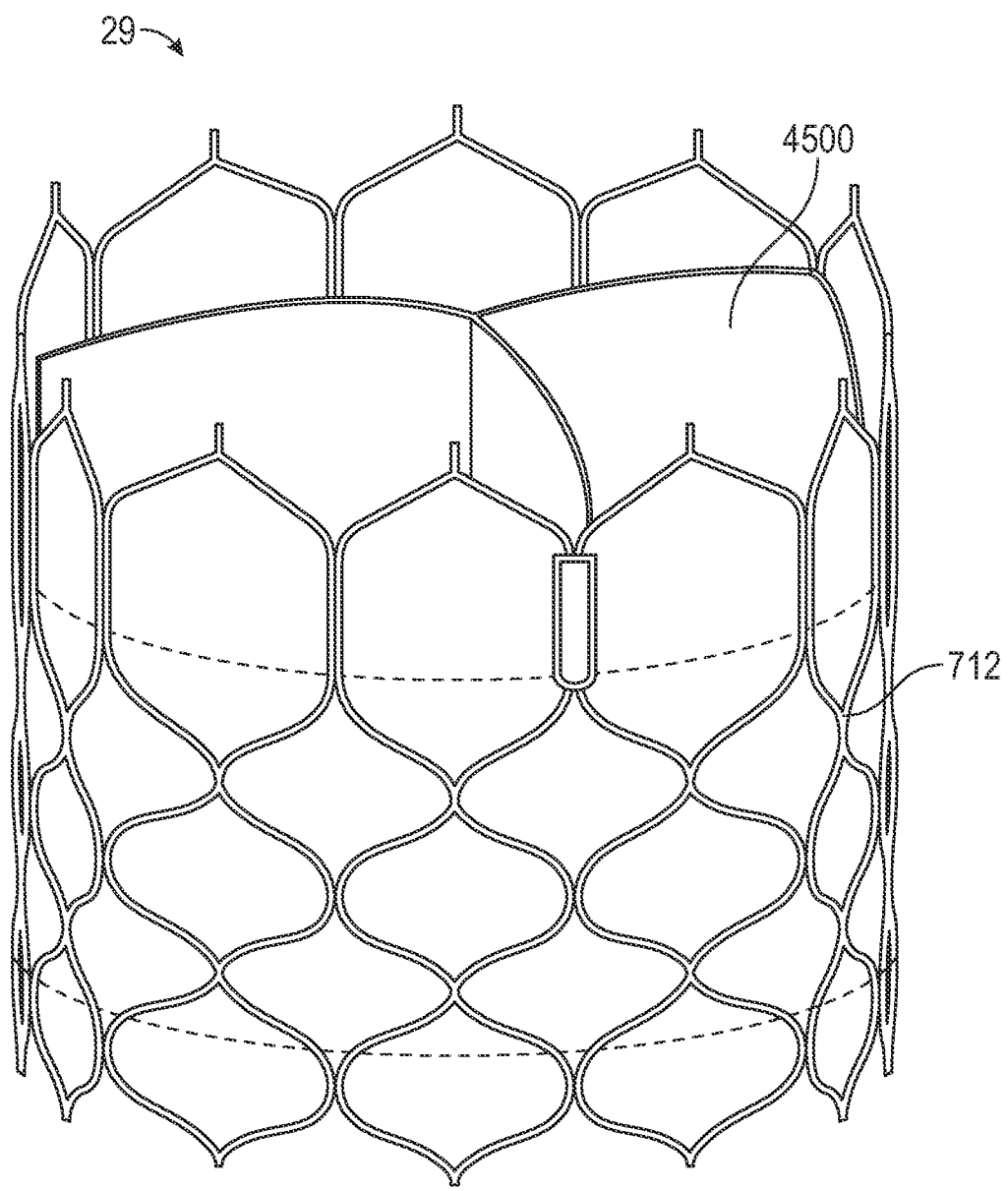
Figure 48A:
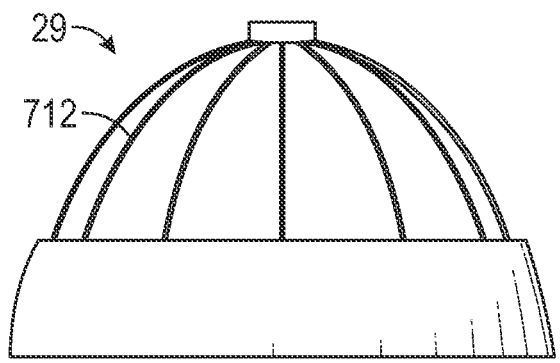
Figure 48B:
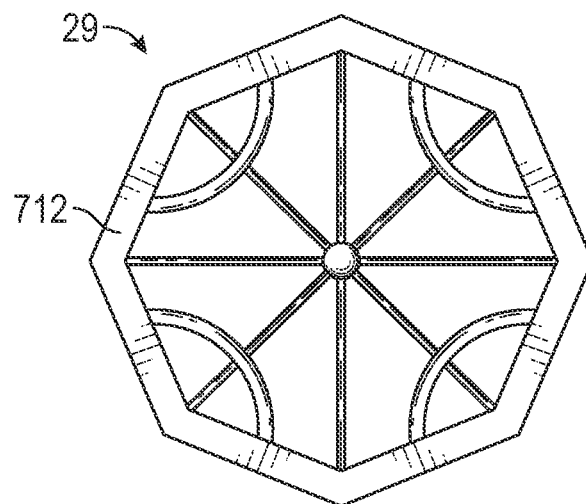
Figure 48C:
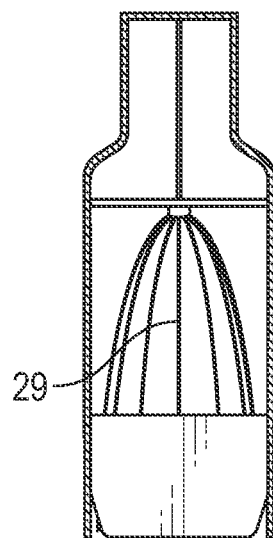

FIGS. 44-48 illustrate a few examples of the many valves or valve configurations that can be used. Any valve type may be used and some valves that are traditionally applied surgically may be modified for transcatheter implantation. FIG. 44 illustrates an expandable valve 29 for transcatheter implantation that is shown and described in U.S. Pat. No. 8,002,825, which is incorporated herein by reference in its entirety. An example of a tri-leaflet valve is shown and described in Published Patent Cooperation Treaty Application No. WO 2000/42950, which is incorporated herein by reference in its entirety. Another example of a tri-leaflet valve is shown and described in U.S. Pat. No. 5,928,281, which is incorporated herein by reference in its entirety. Another example of a tri-leaflet valve is shown and described in U.S. Pat. No. 6,558,418, which is incorporated herein by reference in its entirety. FIGS. 45-47 illustrate an exemplary embodiment of an expandable tri-leaflet valve 29, such as the Edwards SAPIEN Transcatheter Heart Valve. Referring to FIG. 45, in one exemplary embodiment the valve 29 comprises a frame 712 that contains a tri-leaflet valve 4500 (See FIG. 46) compressed inside the frame 712. FIG. 46 illustrates the frame 712 expanded and the valve 29 in an open condition. FIG. 47 illustrates the frame 712 expanded and the valve 29 in a closed condition. FIGS. 48A, 48B, and 48C illustrate an example of an expandable valve 29 that is shown and described in U.S. Pat. No. 6,540,782, which is incorporated herein by reference in its entirety. An example of a valve is shown and described in U.S. Pat. No. 3,365,728, which is incorporated herein by reference in its entirety. Another example of a valve is shown and described in U.S. Pat. No. 3,824,629, which is incorporated herein by reference in its entirety. Another example of a valve is shown and described in U.S. Pat. No. 5,814,099, which is incorporated herein by reference in its entirety. Any of these or other valves may be used as valve 29 in the various embodiments disclosed herein.

FIGS. 49A, 49B and 50A-50D illustrate a distal portion of an exemplary embodiment of a catheter 3600 for delivering and deploying the docking station 10. The catheter 3600 can take a wide variety of different forms. In the illustrated example, the catheter 3600 includes an outer tube/sleeve 4910, an inner tube/sleeve 4912, a docking station connector 4914 that is connected to the inner tube 4912, and an elongated nosecone 28 that is connected to the docking station connector 4914 by a connecting tube 4916.

The docking station 10 can be disposed in the outer tube/sleeve 4910 (See FIG. 49B). Elongated legs 5000 can connect the docking station 10 to the docking station connector 4914 (See FIG. 49B). The elongated legs 5000 can be retaining portions that are longer than the remainder of the retaining portions 414. The catheter 3600 can be routed over a guidewire 5002 to position the docking station 10 at the delivery site.

Figure 50A:
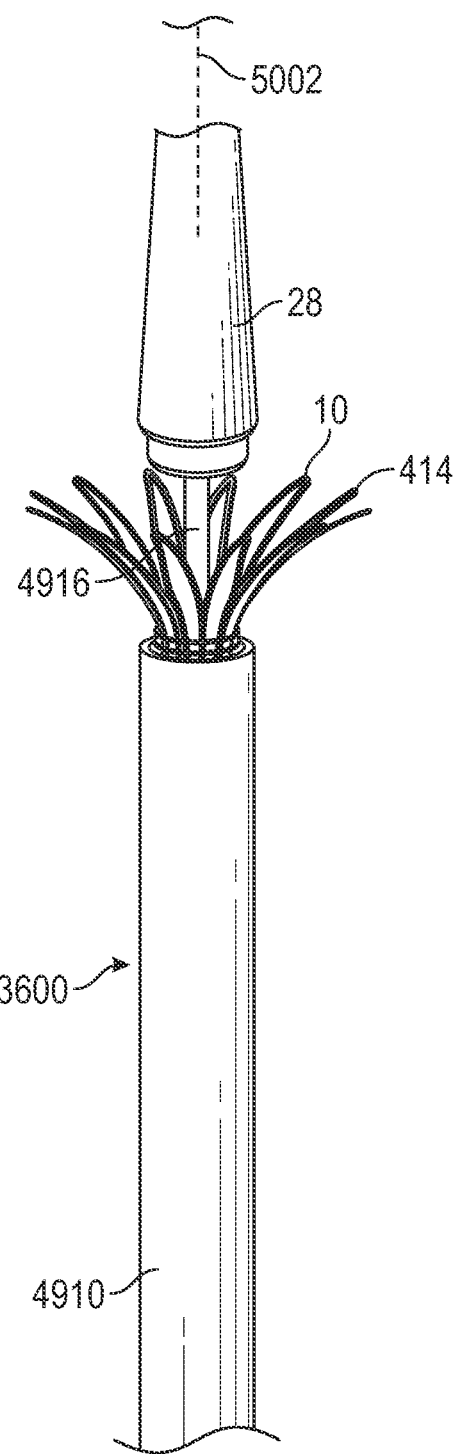
FIGS. 50A-50D illustrate deployment of a docking station from a catheter.
Figure 50B:
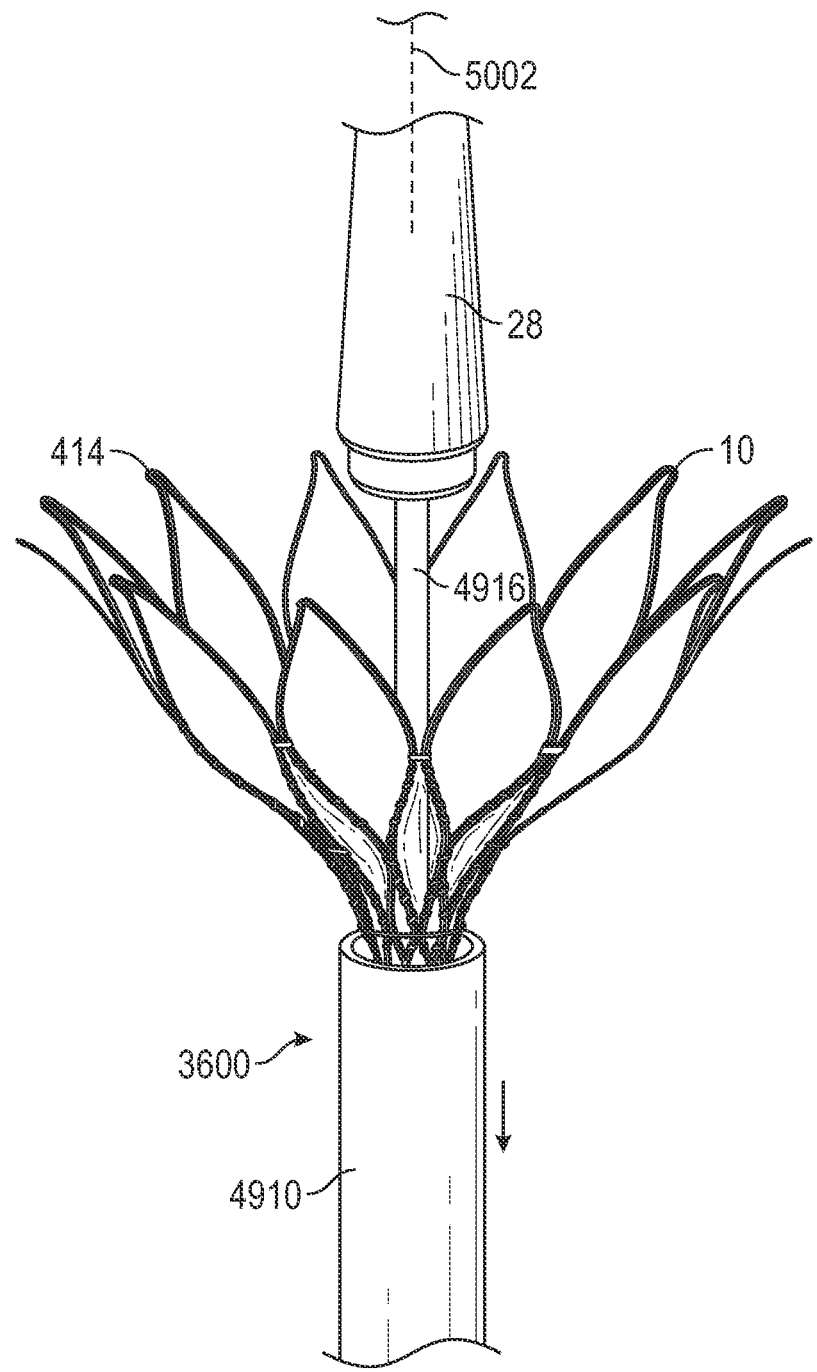
Figure 50C:
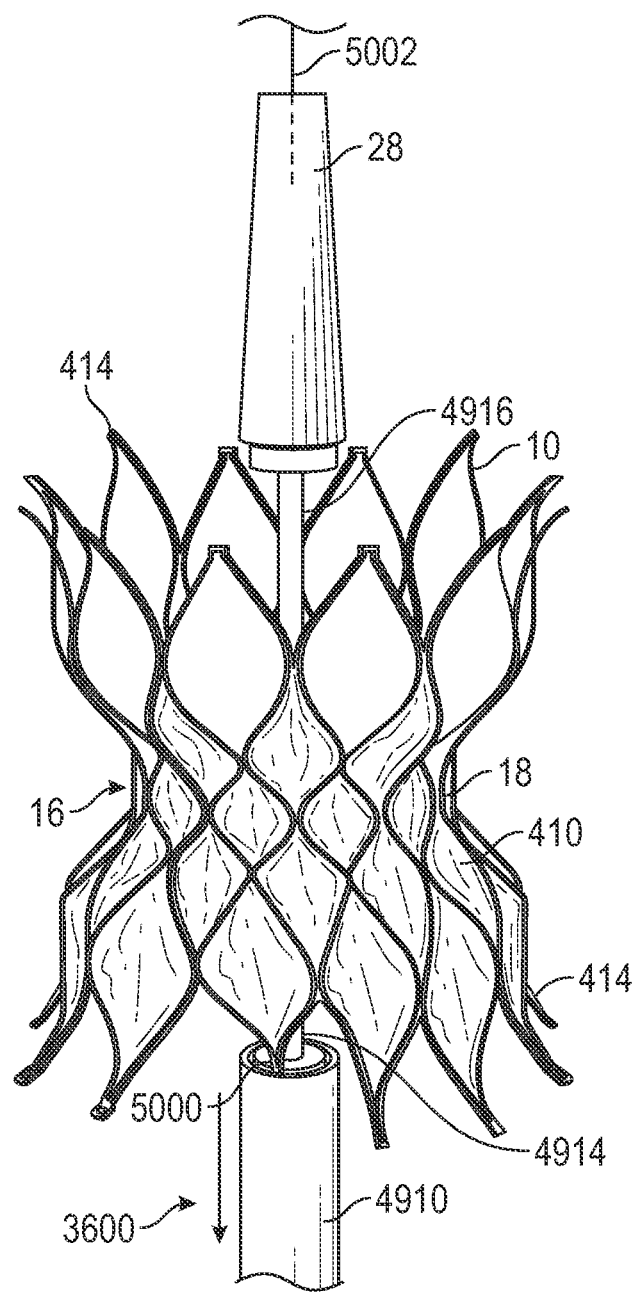
Figure 50D:
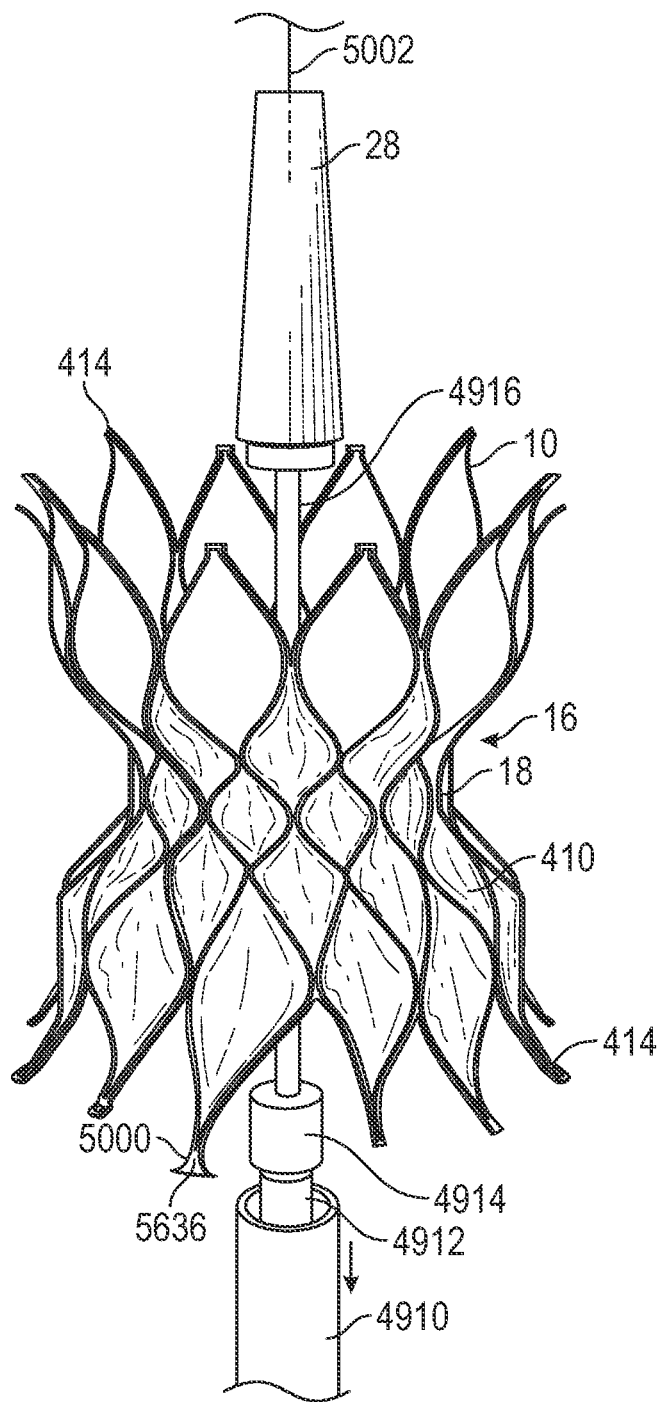

Referring to FIGS. 50A-50D, the outer tube 4910 is progressively retracted with respect to inner tube 4912, the docking station connector 4914, and the elongated nosecone 28 to deploy the docking station 10. In FIG. 50A, the docking station 10 begins to expand from the outer tube 4910. In FIG. 50B, a distal end 14 of the docking station 10 expands from the outer tube 4910. In FIG. 50C, the docking station 10 is expanded out of the outer tube, except the elongated legs 5000 remain retained by the docking station connector 4914 in the outer tube 4910. In FIG. 50D, docking station connector 4914 extends from the outer tube 4910 to release the legs 5000, thereby fully deploying the docking station. During deployment of a docking station in the circulatory system, similar steps may be used and the docking station may be deployed in a similar way.

Figure 51:
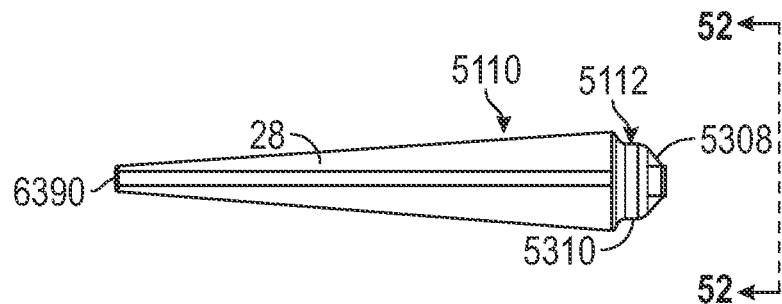
FIG. 51 is a side view of an exemplary embodiment of a nosecone of a catheter.
Figure 52:
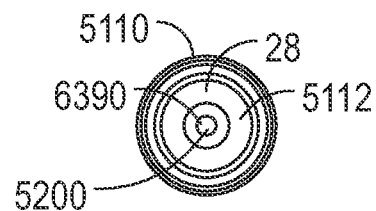
FIG. 52 is a view taken as indicated by lines 52-52 in FIG. 51.

FIGS. 51 and 54 illustrate exemplary embodiments of the nosecone 28. In one exemplary embodiment, the nosecone 28 is an elongated flexible tip or distal end 5110 on a catheter used to assist feeding the catheter 3600 into the heart. In the illustrated examples, nosecone 28 is a long, gradually-tapering cone, with the narrow, distal end of the cone being relatively flexible. In one non-limiting embodiment, a nosecone has a length of 1.5 inches, with an inner lumen 5200 of the nosecone 28 having an inner diameter of 0.04 inches to accommodate the guidewire 5002. In one embodiment, as the diameter of the nosecone 100 increases from the narrow distal end to the wider proximal end, the cone becomes gradually more stiff. This may be due to the increase in thickness and/or the nosecone may be constructed from different materials having different durometers. Optionally, the stiffness of the nose cone at the point it connects with the outer tube 4910 may be approximately the same as the stiffness of the outer tube 4910, in order to prevent a sudden change in stiffness. In the examples illustrated by FIGS. 51 and 54, the elongated distal ends 5110 of the nosecone 28 are the same. In one embodiment, the taper of the nosecone 28 extends the full length or only a portion of the length of the nosecone 28 from end to end. To form the taper an outer diameter of the nosecone 28 can increase in a distal to proximal direction. The taper can take a variety of shapes and the outer surface of the taper can be at a variety of angles with respect to a longitudinal axis of the nosecone 28.

In one exemplary embodiment, a longer distal end 5110 of the nosecone 28 assists in navigating around a bend or curve in the patient's vasculature. Because of the increased length of the nosecone 28 more of the tip gets around the bend, and creates a "follow-the-leader" effect with the remainder of the nose cone.

Figure 53:
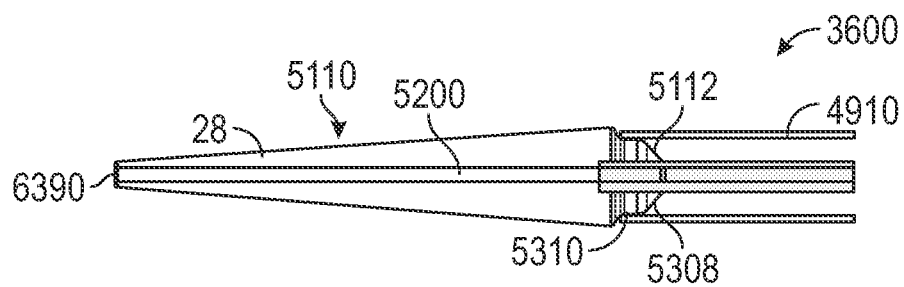
FIG. 53 is a sectional view of an exemplary embodiment of a distal portion of a catheter.

In the example illustrated by FIG. 51, the base or proximal end 5112 of the nosecone 28 has a proximal angled portion 5308 adjacent to a shelf 5310. The proximal angled portion does not catch on the docking station 10 that has been implanted in the heart, when the delivery catheter is retrieved. Thus, the proximal base portion 5112 allows for easier removal of the delivery system. Referring to FIG. 53, as the angled portion 5308 (or "ramp") of the base portion 5112 is retracted into the outer tube 4910, the ramp 5308 enters the delivery catheter first, followed by the shelf 5310. When the nose cone 28 engages with the outer sleeve/tube 4910, the inner diameter of the outer sleeve rides up the ramp 5308, and then rests on the shelf 5310 (which can be flat or substantially flat, e.g., 180° or 180°±5° with respect to a longitudinal axis of the nosecone 28). The inner diameter of the outer sleeve/tube 4910 can be slightly less than the diameter of the shelf 5310, to ensure a snug fit.

In one non-limiting example, the shelf 5310 of the nosecone 28 fits snugly into a lumen or outer lumen of the catheter assembly 3600 which, in one non-limiting example, can have a diameter of approximately 0.2 inches or between 0.1 inches and 0.4 inches. In one embodiment, the outer diameter of the largest portion of the nosecone 28 can be 0.27 inches or between 0.2 inches and 0.4 inches, with a diameter at the distal tip of the nosecone of 0.069 inches or between 0.03 inches and 0.1 inches. Again, these dimensions are for illustrative purposes only. For example, the outer diameter or largest outer diameter of the nosecone 28 can be larger than the outer diameter of the outer tube 4910 (e.g., slightly larger as illustrated), the outer diameter of the nosecone 28 can be the same as the outer diameter of the outer tube 4910, or the outer diameter of the nosecone 28 can be smaller (e.g., slightly smaller) than the outer diameter of the outer tube 4910.

In the example illustrated by FIG. 54, the entire base or proximal end/portion 5112 of the nosecone 28 is angled. The continuously angled proximal end 5112 does not catch on the docking station 10 that has been implanted in the heart, when the delivery catheter is retrieved. Thus, the base portion 5112 allows for easier removal of the delivery system. Referring to FIG. 55, the outer tube 4910 may include a chamfer 5500 to accept and mate with the continuously angled proximal end 5112.

In one non-limiting example, the continuously angled proximal end 5112 of the nosecone 28 fits snugly into the outer tube/sleeve 4910 (which can optionally be chamfered) of the catheter assembly 3600. The outer diameter or largest outer diameter of the nosecone 28 can be larger (e.g., slightly larger) than the outer diameter of the outer tube 4910, the outer diameter of the nosecone 28 can be the same as the outer diameter of the outer tube 4910 as illustrated, or the outer diameter of the nosecone 28 can be smaller (e.g., slightly smaller) than the outer diameter of the outer tube 4910.

The docking station 10 can be coupled to the catheter assembly, or a docking station connector 4914 of the catheter assembly, in a wide variety of different ways. For example, the docking station 10 could be coupled with the catheter assembly with a lock(s), locking mechanism, suture(s) (e.g., one or more sutures releasably attached, tied, or woven through one or more portion of the docking station), interlocking device(s), a combination of these, or other attachment mechanisms. Some of these coupling or attachment mechanisms may be configured to allow for the docking station to be retracted back into the catheter assembly without causing the docking station to catch on edges of the catheter assembly, e.g., by constraining the proximal end of the docking station to a smaller profile or collapsed configuration, to allow for adjustment, removal, replacement, etc. of the docking station. FIGS. 56, 57, 57A, and 57B illustrate one non-limiting example of how docking station 10 may be coupled to the docking station connector 4914. As is illustrated by FIGS. 50A-50D, when the docking station 10 is pushed out of the outer tube, it self-expands in one exemplary embodiment. One approach to controlling expansion of the docking station 10 is to anchor at least one end, such as the proximal end 12, of the stent to the docking station connector 4914. This approach allows a distal end 14 of the stent to expand first, without the proximal end expanding (See FIG. 50B). Then when the stent is moved relatively forward with respect to the outer tube 4910, the proximal end 12 disengages from the docking station connector 4914, and the proximal end 12 of the docking station is permitted to expand (See FIG. 50D).

One way of accomplishing this approach is to include one or more extensions 5000 on at least the proximal end of the stent 12. In the illustrated examples, two extensions are included. However, any number of extensions 5000, such as two, three, four, etc. can be included. The extensions 5000 can take a wide variety of different forms. The extensions 5000 can engage with the docking station connector 4914 within the outer tube 4910. In one exemplary embodiment, the docking station connector 4914 may engage an inner face 5600 of the extensions 5000. In one exemplary embodiment, other than possible engagement of an inner face 5600 (See FIG. 57A) of the extensions 5000 with the docking station connector 4914, the extensions 5000 and docking station connector 4914 are configured to limit the retaining engagement therebetween to two points when the distal portion of the catheter assembly and/or docking station are in a straight or substantially straight configuration, but these could similarly be configured to limit the retaining engagement another number of points, e.g., three to six points. In one exemplary embodiment, the inner face 5600 of the extensions 5000 do not contact with the docking station connector 4914 when the distal portion of the catheter assembly and/or the docking station is in a straight or substantially straight configuration, due to the radially outward biasing force of the compressed extensions. In this embodiment, the inner face 5600 of the extensions 5000 could contact the docking station connector 4914 due to bending of the catheter assembly 3600 and/or the docking station. The extensions 5000 may include heads 5636 with sides 5640 that extend away from a straight portion 5638 at an angle β (See FIG. 57A), such as between 30 and 60 degrees. Such heads 5636 may be generally triangular as illustrated or the angularly extending sides 5640 may be connected together by another shape, such as a rounded shape, a rectangular shape, pyramidal shape, or another shape. That is, the heads 5636 may function in the same manner as the illustrated triangular head, without being triangular.

Figure 57:
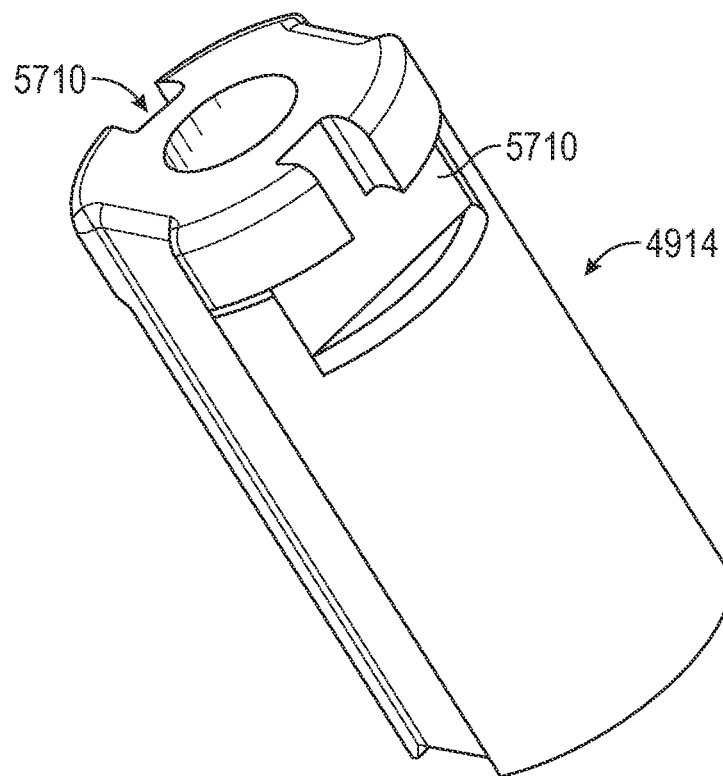
FIG. 57 is a perspective view of a holder for retaining a docking station in a catheter.
Figure 57B:
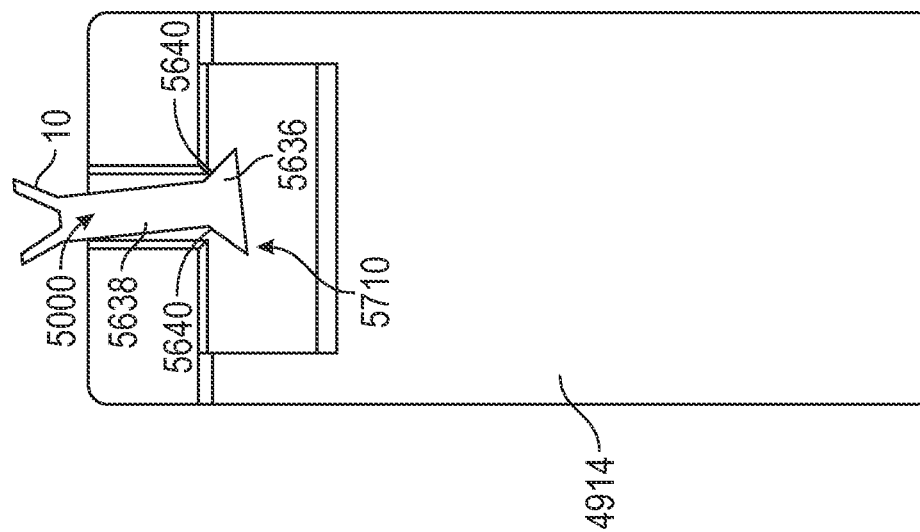
FIGS. 57A and 57B illustrate side views of extensions of a docking station disposed in the holder.
Figure 57A:
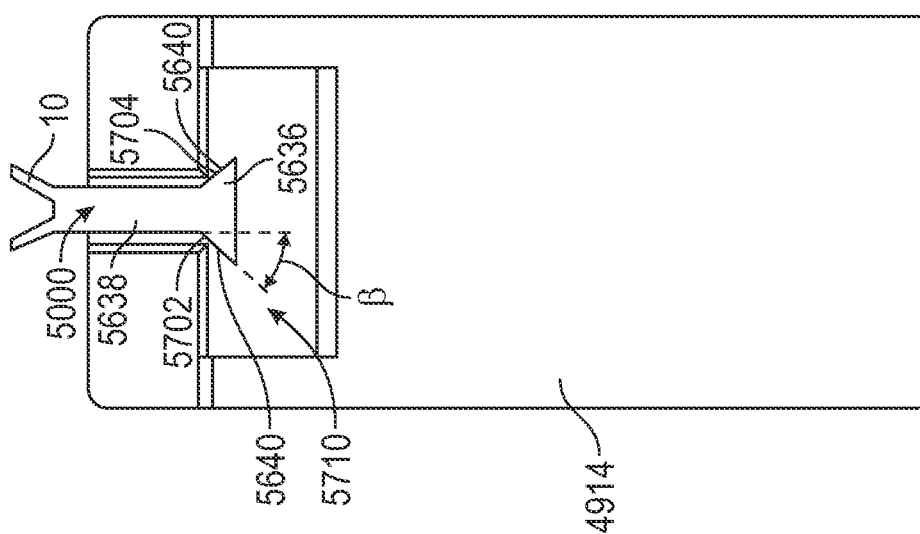
Figure 58:
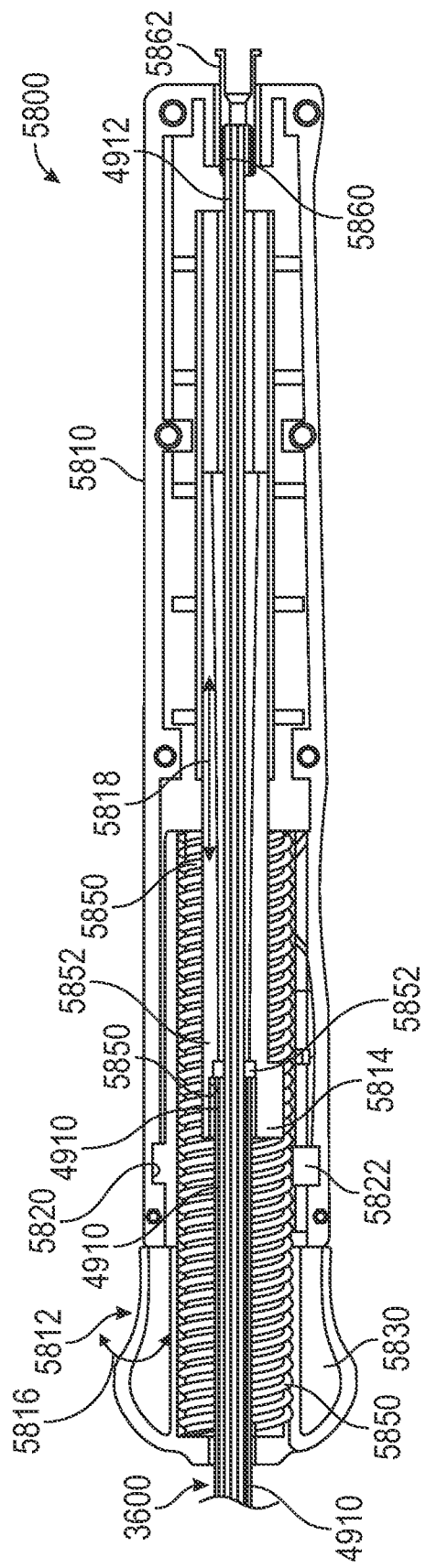
FIG. 58 is a sectional view of an exemplary embodiment of a handle for a docking station catheter.

The delivery catheter 3600 constantly bends and curves as it moved through the vasculature of the patient's body. A head 5636 that transitions directly from an straight portion 5638 of the extension 5000 to a T-shape, curved T-shaped, circular or spherical shape will generally have more than two point retaining contact with its holder (other than possible engagement of an inner face 5600 (See FIG. 17A) of the extension 5000 with the docking station connector 4914). Referring to FIGS. 57A and 57B, a head 5636 with sides 5640 that extend away from one another at an angle β, such as a triangular head, results in the head 5636 only touching the docking station connector 4914 at two points 5702, 5704. In the example illustrated by FIG. 57A, the two points are corners formed by a T-shaped recess 5710. As shown in FIG. 57B, the extension 5000 can tilt as the catheter 3600 and docking station 10 moves through the body during delivery. In one exemplary embodiment, this tilting can also result in only two point contact between the extension 5000 and the docking station connector 4914 as illustrated by FIG. 57B (other than possible engagement of an inner face 5600 (See FIG. 17A) of the extension 5000 with the docking station connector 4914). As such, the extension 5000 can tilt during delivery, increasing the flexibility of the catheter 3600 in the area of the docking station 10, while the two point contact prevents binding between the extension 5000 and the connector 4914.

Figure 56:
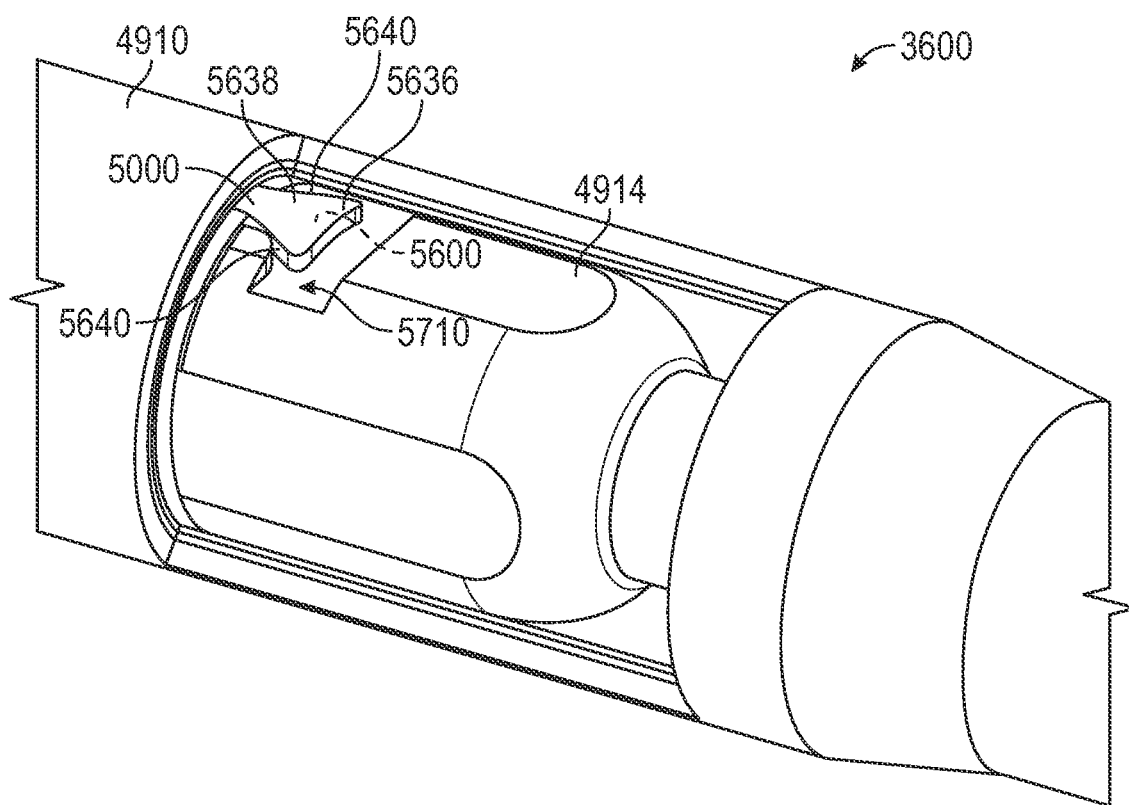
FIG. 56 is a perspective view of a holder for retaining a docking station in a catheter.

Referring to FIGS. 56, 57, 57A, and 57B, the heads 5636 fit into the T-shaped recesses 5710 in a holder to holds the proximal end 12 of the docking station while the distal end self-expands within the body. The docking station connector 4914 remains in the delivery catheter until moved relatively out of the catheter (i.e. by retracting the outer tube/sleeve 4910 or by advancing the connector 4914, See FIG. 50D). Referring to FIG. 56, the outer tube/sleeve 4910 of the catheter 3600 can be closely disposed over the connector 4914, such that the heads 5636 are captured in the recesses 5710, between the outer tube/sleeve 4910 and the body of the connector 4914. This capturing in the recesses 5710 holds the end of the docking station 10 as the docking station expands. In this manner, delivery of the docking station 10 is controlled.

Referring back to FIG. 50D, at the end of the expansion of the docking station 10—when the distal end of the stent has already expanded—the connector 4914 is moved relatively out of the outer sleeve. The heads 5636 are then free to move radially outward and disengage with the respective recesses 5710 (see FIG. 56).

In one embodiment, all of the extensions 5000 are the same length. As the connector is moved relatively out of the outer tube/sleeve 4910, the recesses 5710 are simultaneously relatively moved out of the outer sleeve 4910. Since the extensions 5000 are all the same length, the recesses 5710 with the heads 5636 will all emerge from the delivery outer sleeve 4910 at the same time. Consequently, the heads 5636 of the docking station will move radially outward and release all at once.

In an alternative embodiment, the docking station 10 is provided with extensions 5000 having heads 5636, but at least some of the extensions 5000 are longer than others. That way, as the connector 4914 is gradually moved relatively out of the outer sleeve 4910, the shortest extensions 5000 are released first from their respective recess(es) 5710. Then, as the connector 4914 is moved relatively further out of the outer sleeve 4910, the longer of the extensions 5000 are released from the respective recess(es) 5710. As is described above, in one exemplary embodiment the docking station 10 can be deployed with a catheter/catheter assembly 3600. The catheter/catheter assembly 3600 is advanced in the circulatory system to a delivery site or treatment area. Once at the delivery site, the docking station 10 is deployed by moving an outer sleeve or tube 4910 relative to an inner sleeve or tube 4912 and attached connector 4914 and docking station 10 (See FIGS. 50A-50D). The outer sleeve 4910 can be moved relative to the inner sleeve 4912 in a wide variety of different ways. FIGS. 58-61 and 62-73 illustrate examples of tools or handles 5800, 6200 that can be used for moving a catheter 3600 in the circulatory system and relatively moving an outer sleeve 4910 relative to an inner sleeve 4912 of the catheter 3600, e.g., to deploy/place a docking station.

Figure 59:
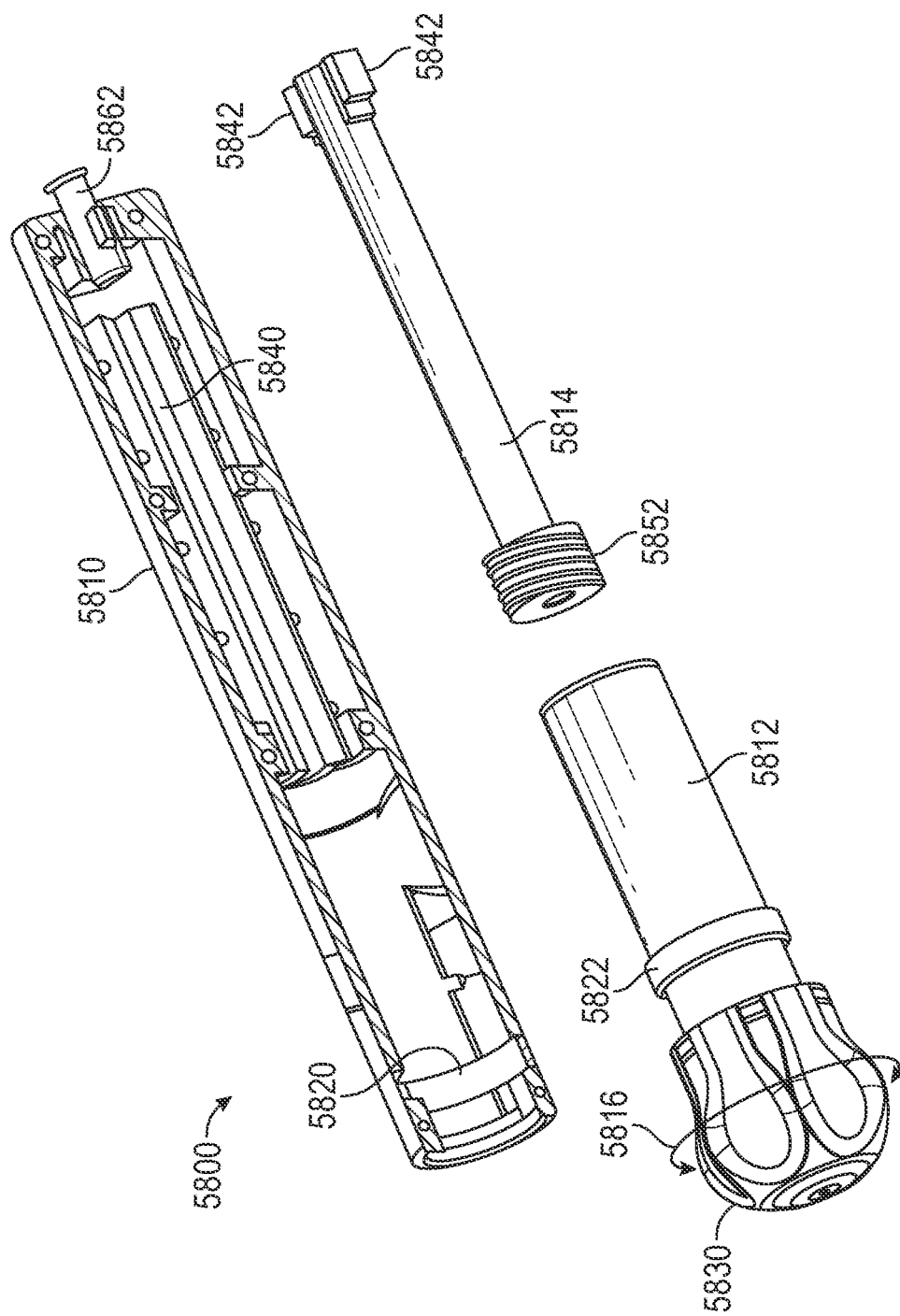
FIG. 59 is an exploded perspective view of parts of the handle of FIG. 58.
Figure 60:
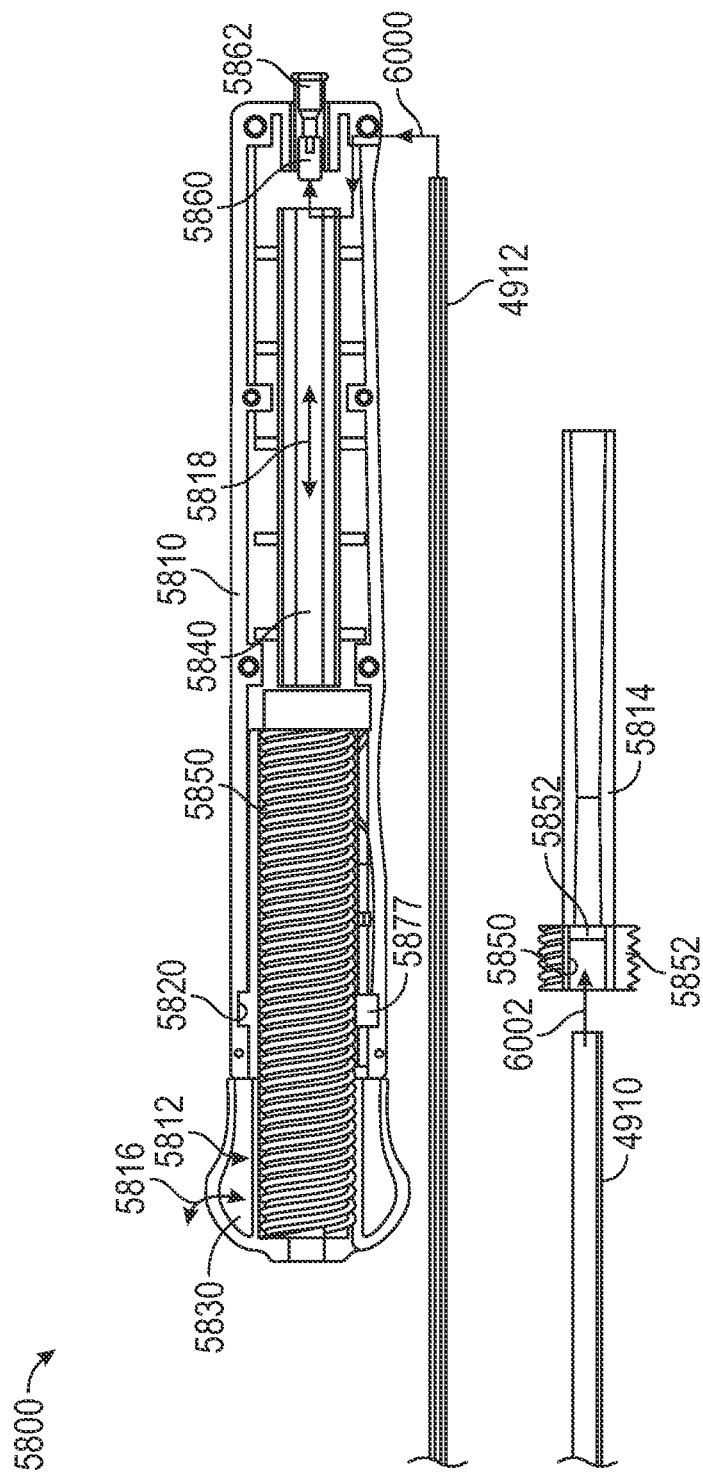
FIG. 60 is an exploded sectional view of parts of the handle of FIG. 58.
Figure 61:
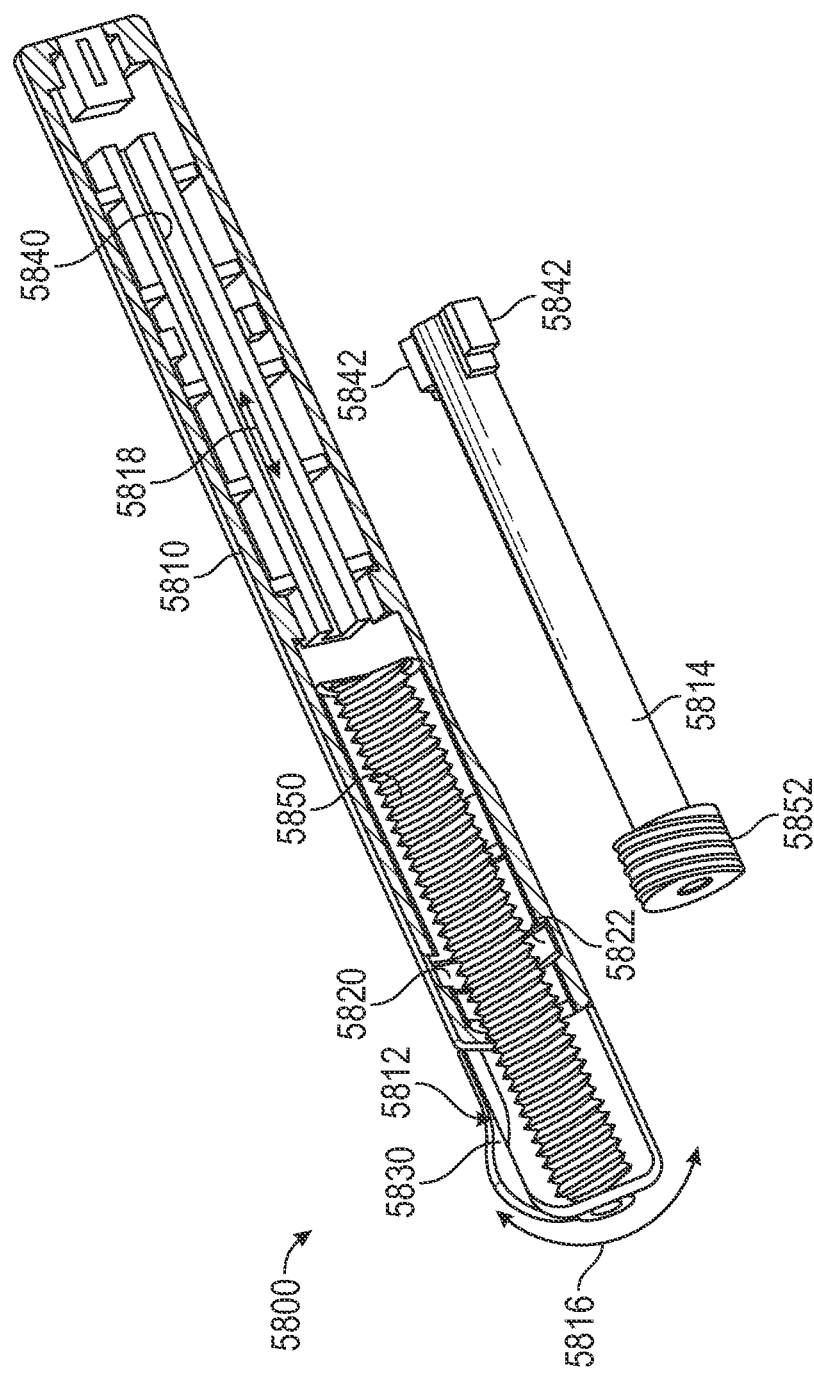
FIG. 61 is an exploded perspective sectional view of parts of the handle of FIG. 58.
Figure 64A:
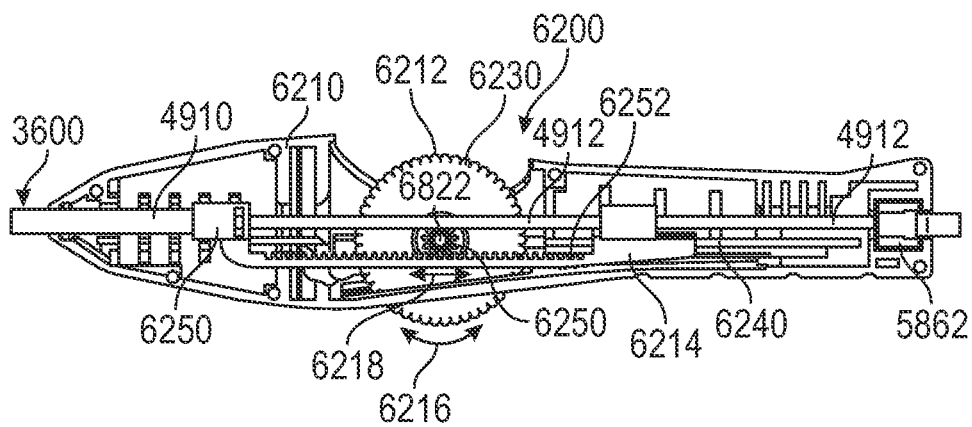
FIGS. 64A and 64B are views of the handle illustrated by FIG. 62 with an opposite side cover removed to illustrate extension and retraction of an outer sleeve of a docking station catheter.
Figure 64B:
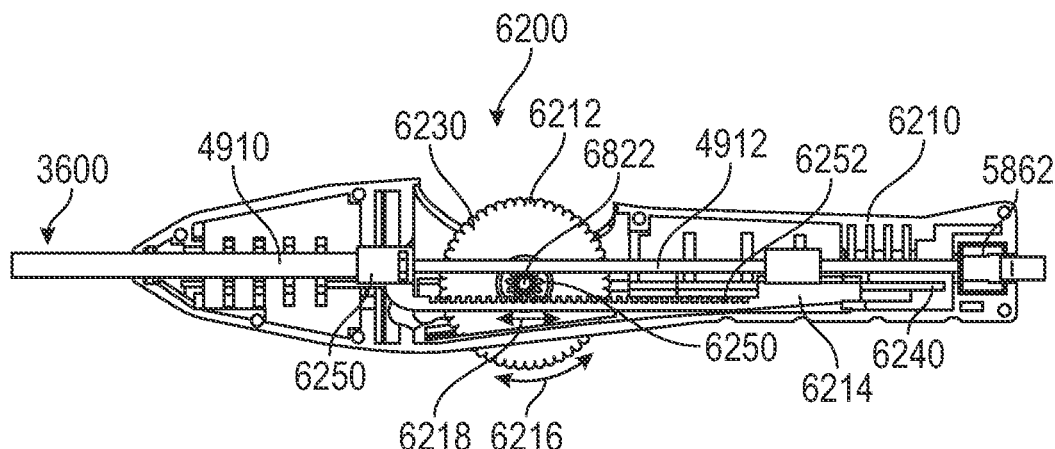
Figure 65:
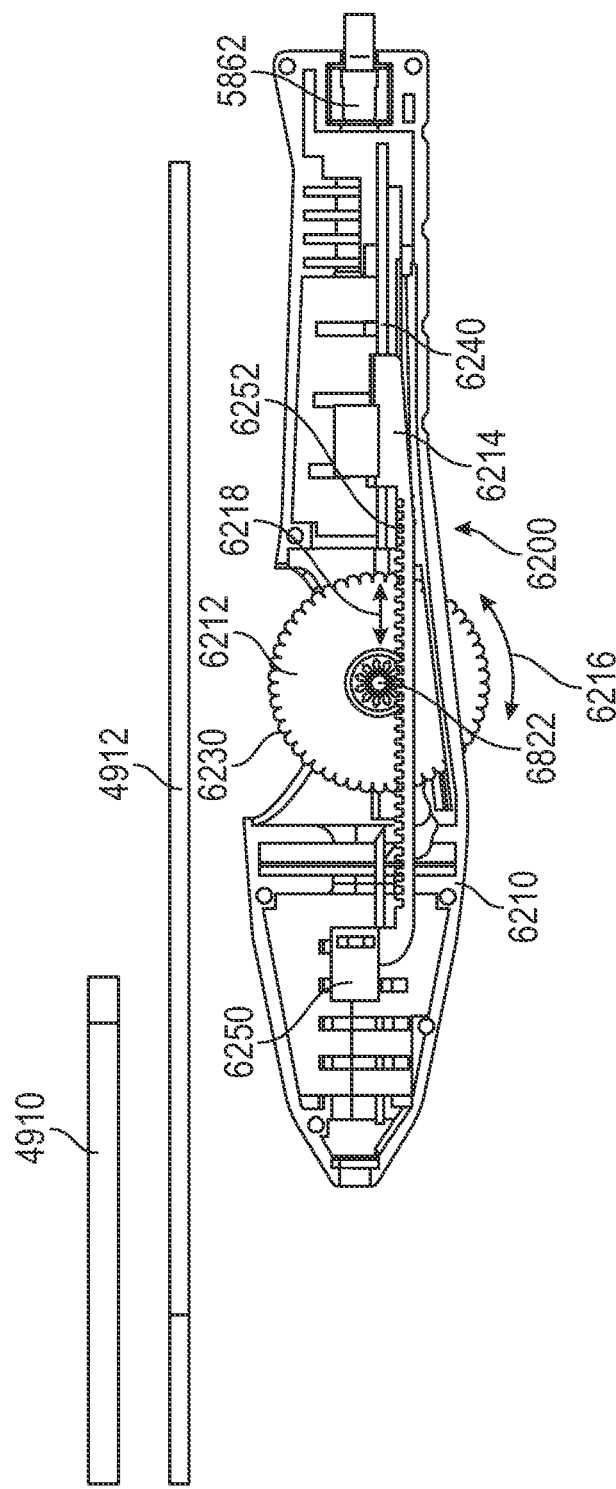
FIG. 65 is an exploded view of the handle of FIG. 62.

In the example illustrated by FIGS. 58-61, the handle 5800 includes a housing 5810, a drive member 5812, and a driven shaft 5814. In the illustrated example, rotation of the drive member 5812 as indicated by arrow 5816 relative to the housing 5810 moves the driven shaft 5814 linearly as indicated by arrow 5818. Referring to FIG. 60, the inner sleeve 4912 is fixedly connected to the housing 5810 as indicated by arrow 6000 and the outer sleeve 4910 is fixedly connected to the driven shaft 5814 as indicted by arrow 6002. As such, rotating the drive member 5812 in a first direction retracts the outer sleeve 4910 relative to the inner sleeve 4912 and rotating the drive member 5812 in the opposite direction advances the outer sleeve 4910 relative to the inner sleeve 4912.

In the example illustrated by FIGS. 58-61, the housing 5810 includes an annular recess 5820. The drive member 5812 includes an annular projection 5822. The annular projection 5822 fits within the annular recess to rotatably couple the drive member 5812 to the housing 5810. The drive member 5812 includes an engagement portion 5830 that extends from the housing to allow a user to rotate the drive member 5812 relative to the housing 5810.

In the example illustrated by FIGS. 58-61, the housing 5810 includes a linear recess 5840 or groove (See FIG. 59). The driven shaft 5814 includes a linear projection 5842. The linear projection 5842 fits within the linear recess 5840 to slideably couple the driven shaft 5814 to the housing 5810.

In the example illustrated by FIGS. 58-61, the drive member 5812 includes internal threads 5850. The driven shaft 5814 includes an externally threaded portion 5852. The externally threaded portion 5852 mates with the internal threads 5850 to operationally couple the drive member 5812 to the driven shaft 5814. That is, when the drive member 5812 is rotated relative to the housing 5810 as indicated by arrow 5816, the driven shaft 5814 is prevented from rotating due to the linear projection 5842 that fits within the linear recess 5840. As such, rotation of the drive member 5812 in the housing 5810 causes the driven shaft 5814 to linearly slide 5818 along the linear recess 5840 due to the engagement of the externally threaded portion 5852 mates with the internal threads 5850. Since the outer shaft/tube 4910 is connected to the driven shaft 5814 and the inner shaft/tube 4912 is connected to the housing 5810, the outer shaft/tube 4910 is advanced and retracted relative to the inner shaft/tube 4912 by rotation of the drive member 5812.

In the example illustrated by FIGS. 58-61, the outer shaft/tube 4910 is fixedly connected in a recess 5850 in the driven shaft 5814 and an optional seal 5852 is provided between the outer shaft/tube 4910 and the inner shaft/tube 4912 and/or between the outer shaft/tube 4910 and the driven shaft 5814. A luer port 5862 is fixedly connected to the housing 5810, e.g., a proximal end of the housing 5810 as shown. The inner shaft/tube 4912 is fixedly connected in a recess 5860 in the luer port 5862. The luer port 5862 is configured to accept a guide wire 5002 (See FIG. 49) that extends through the inner shaft/tube 4912.

In the example illustrated by FIG. 62-67, the handle 6200 includes a housing 6210, a drive wheel 6212, and a driven member 6214. In the illustrated example, rotation of the drive wheel 6212 as indicated by arrow 6216 relative to the housing 6210 moves the driven member 6214 linearly as indicated by arrow 6218 (compare the position of the driven member 6214 in FIGS. 64A and 64B). Referring to FIG. 62, the inner sleeve/tube 4912 is fixedly connected to the housing 6210 and the outer sleeve/tube 4910 is fixedly connected to the driven member 6214. As such, rotating the drive wheel 6212 in a first direction retracts the outer sleeve 4910 relative to the inner sleeve 4910 and rotating the drive wheel 6212 in the opposite direction advances the outer sleeve/tube 4910 relative to the inner sleeve/tube 4912. Although, in the various embodiments shown in FIGS. 58-73, the inner sleeve/tube 4912 is shown and described as being connected unmovably relative to the handle or a proximal end of the handle while the outer sleeve/tube 4910 is movable relative to the handle or a proximal end of the handle, in one embodiment using similar concepts, the inner sleeve/tube 4912 could be moveable relative to the handle or a proximal end of the handle while the outer sleeve/tube 4910 is connected unmovably relative to the handle or a proximal end of the handle, or both the inner sleeve/tube 4912 and outer sleeve/tube 4910 may be configured to be movable relative to each other and relative to the handle or proximal end of the handle.

In the example illustrated by FIGS. 62-67, the housing 6210 rotatably accepts an axle 6822 of the drive wheel 6212 to rotatably couple the drive wheel to the housing 6210. The drive wheel 6212 includes an engagement portion 6230 that extends from the housing 6210 to allow a user to rotate the drive wheel 6212 relative to the housing 6210.

Figure 66:
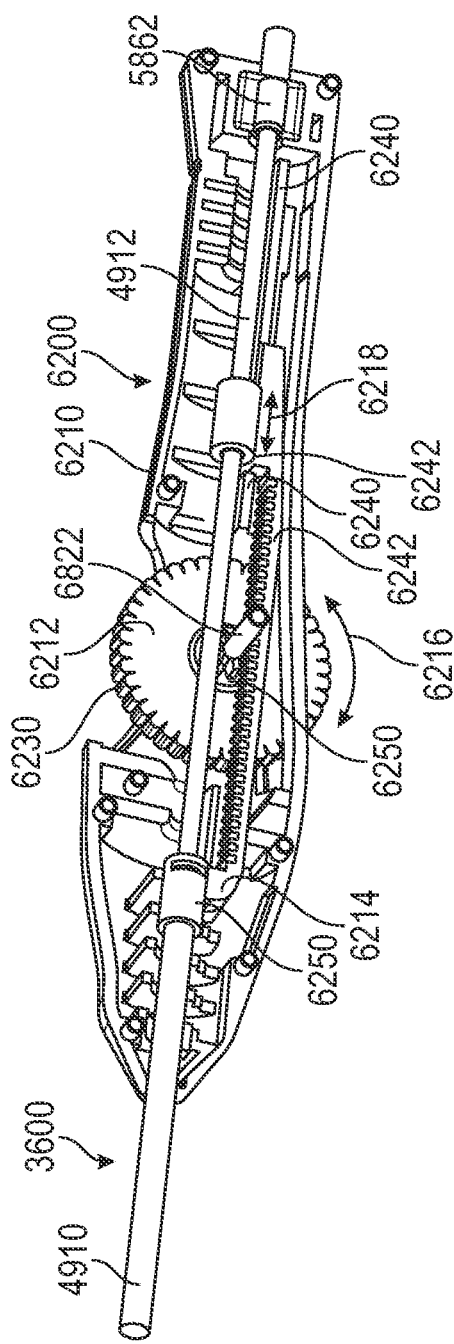
FIG. 66 is a perspective view of the handle illustrated by FIG. 62 with the opposite side cover removed
Figure 67:
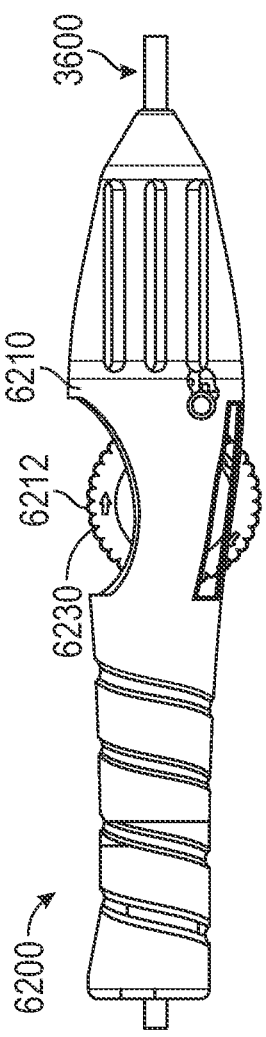
FIG. 67 is a side view of the handle illustrated by FIG. 62.
Figure 68:
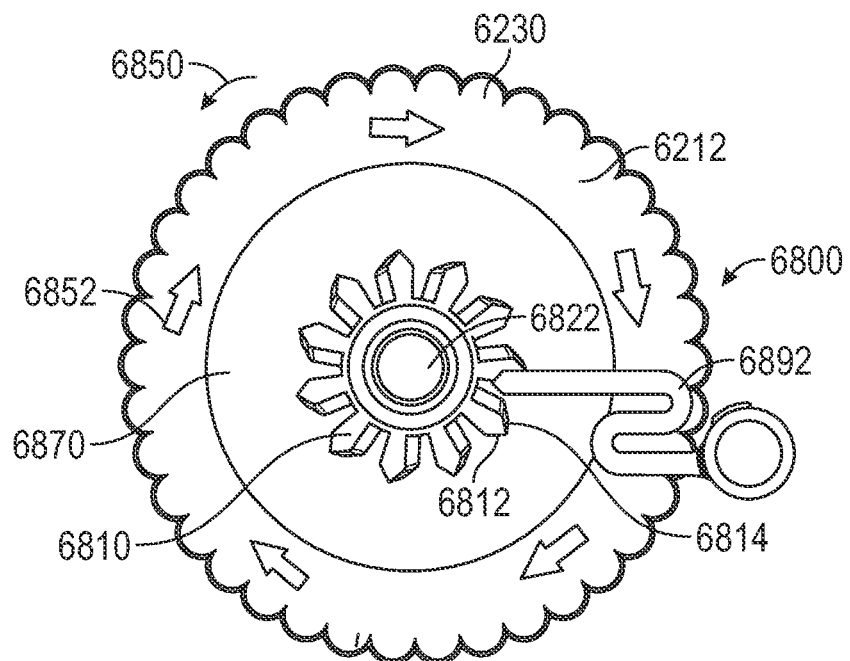
FIG. 68 is a side view of an indexing wheel of the handle illustrated by FIG. 62 in a ratcheting state.
Figure 69:
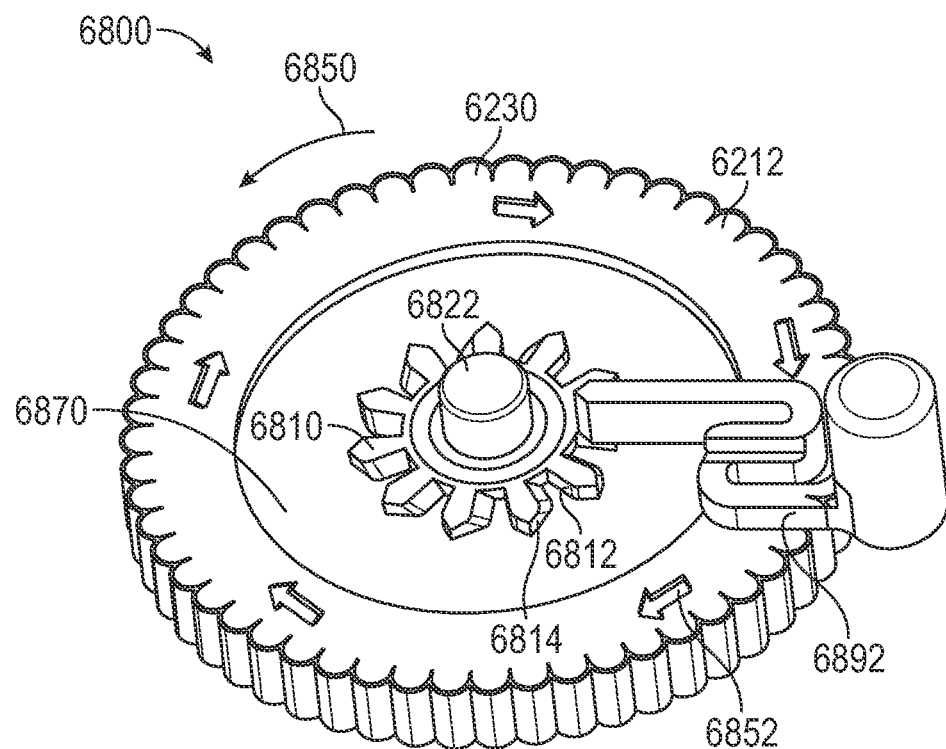
FIG. 69 is a perspective view of the indexing wheel of FIG. 68 in the ratcheting state.
Figure 70:
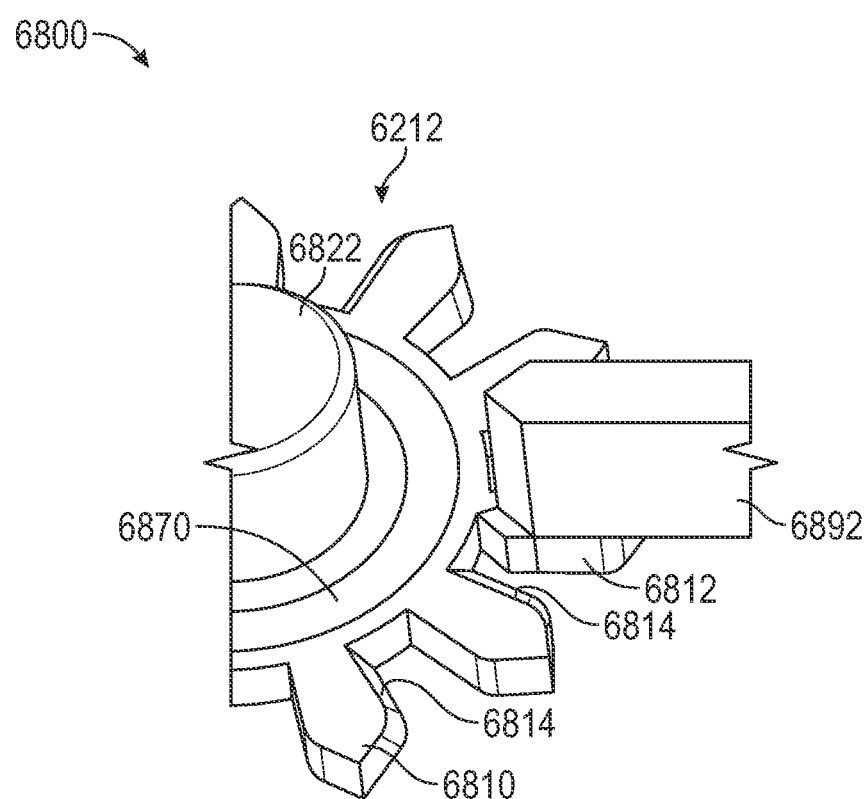
FIG. 70 is an enlarged portion of FIG. 69.

In the example illustrated by FIGS. 62-67, the housing 6210 includes a linear projection 6240 (See FIG. 66). The driven member 6214 includes a linear groove 6242 (See FIGS. 62, 66) that the projection 6240 fits within to slideably couple the driven member 6214 to the housing 6210.

In the example illustrated by FIGS. 62-67, the drive member 6212 includes a pinion gear 6250. The driven member 6214 includes a gear rack portion 6252. The pinion gear 6250 meshes with the gear rack portion 6252 to operationally couple the drive wheel 6212 to the driven member 6214. That is, when the drive wheel 6212 is rotated relative to the housing 6210 as indicated by arrow 6216, the driven member 6214 slides relative to the housing 6210 due to the linear projection 6240 that fits within the linear recess 6242. As such, rotation of the drive member 6212 relative to the housing 6210 causes the pinion gear 6250 to drive the gear rack portion 6252 to cause the driven member 6214 to linearly slide 6218 relative to the housing 6210. Since the outer shaft/tube 4910 is connected to the driven member 6214 and the inner shaft/tube 4912 is connected to the housing 5810, the outer shaft/tube 4910 is advanced and retracted relative to the inner shaft/tube 4912 by rotation of the drive wheel 6212.

In the example illustrated by FIGS. 62-67, the outer shaft/tube 4910 is fixedly connected in a support portion 6250 that extends from the gear rack portion 6252 of the driven member 6214 and an optional seal (not shown) is provided between the outer shaft/tube 4910 and the inner shaft/tube 4912 and/or between the outer shaft/tube 4910 and the driven member 6214. A luer port 5862 is fixedly connected to the housing 6210, e.g., at a proximal end of the housing 6210. The inner shaft/tube 4912 is fixedly connected in a recess 5860 in the luer port 5862. The luer port 5862 is configured to accept a guide wire 5002 (See FIG. 49) that extends through the inner shaft/tube 4912.

Referring to FIG. 63, in one exemplary embodiment, the catheter 3600 may be flushed by applying a fluid to the inner tube 4912, such as to the inner tube via the luer port 5862. As is described above, the delivery catheter 3600 includes an outer lumen formed within an outer tube/sleeve 4910 and an inner lumen formed within an inner tube/sleeve 4912, and the inner lumen and inner tube 4912 are longitudinally co-axial with the outer lumen and outer tube 4910. An annular lumen/gap/space 6348 in between the inner tube 4912 and outer tube 4910 that may result from, for example, the need to provide space for a crimped stent to travel through the catheter 3600. This gap/space 6348 can initially be filled with air, which can be subsequently expelled and replaced with a liquid, e.g., a saline solution. Flushing in this way can be done with the various handle embodiments shown in FIGS. 58-73.

In one exemplary embodiment, a fluid such as saline or another suitable fluid, flows from the luer port 5862 and through the inner lumen of inner tube 4912 as indicated by arrow 6360. In this embodiment, the inner tube 4912 is provided with one or more flushing apertures 6354. The fluid flows through the inside of the inner tube 4912, out the apertures 6354 as indicated by arrows 6370 and into the gap/space 6348.

As the gap/space 6348 fills with fluid, air is pushed out of the delivery catheter through the distal end of the outer tube 4910. In one exemplary embodiment, the nosecone 28 is disengaged from the distal end of the outer tube 4910 to allow the air to flow out of the outer tube and out of the catheter 3600. Fluid also flows through the inner lumen of the inner tube 4912 to push air out of the inner lumen. In one exemplary embodiment, the air is forced out of the inner lumen through the opening 6390 in the end of the nosecone 28 (See FIGS. 49A and 49B). This flushing procedure is performed before the delivery catheter 3600 is introduced into the body. The device and method of this approach saves space as compared to, for example, providing a side port on the outer tube 4910 for introducing a flushing fluid into the delivery catheter assembly or gap/space 6348.

Referring to FIGS. 68-73, in one exemplary embodiment, the handle 6200 illustrated by FIGS. 62-67 can be provided with a ratchet mechanism 6800. The ratchet mechanism 6800 can take a wide variety of different forms and can be used with the handle 6200 in a variety of different ways. In one exemplary embodiment, the ratchet mechanism 6800 is used during a "recapture" of the docking station 10 to pull it back into the delivery catheter 3600. The force required to recapture the docking station can be significant. As such, the ratchet mechanism 6800 can be configured such that, when the ratchet mechanism is engaged (FIGS. 68-71), the drive wheel 6212 can only be rotated in the direction that draws the docking station 10 back into the outer tube/sleeve 4910. That is, the spring force of the docking station 10 is prevented from pulling the docking station back out of the outer tube by the ratchet mechanism 6800. The operator can recapture the docking station 10 sequentially, without the docking station slipping back if the operator lets go of the drive wheel 6212, for instance.

Referring to FIGS. 68-71, one exemplary ratchet system uses projections 6810 with stop surfaces 6812 on one side of the projections and ramp surfaces 6814 on the other side of the projections. FIGS. 68-71 illustrate an engaged condition where a ratchet arm 6892 is positioned to engage with the projections 6810 to permit the wheel drive wheel 6212 to rotate in one direction, and to prevent the drive wheel from turning in the opposite direction. For example, the ratchet arm 6892 may be configured to ride over the ramped surfaces 6814 to allow movement of the drive wheel 6212 in the retracting direction 6850. For example, the ratchet arm 6892 may flex to ride over the inclined ramped surfaces 6814. The stop surfaces 6812 are configured to engage the ratchet arm 6892 and prevent rotation of the drive wheel in the advancing direction 6852. For example, the stop surfaces 6812 may be substantially orthogonal to a side surface 6870 of the drive wheel 6212 to prevent the ratchet arm from moving over the projection 6810.

Figure 72:
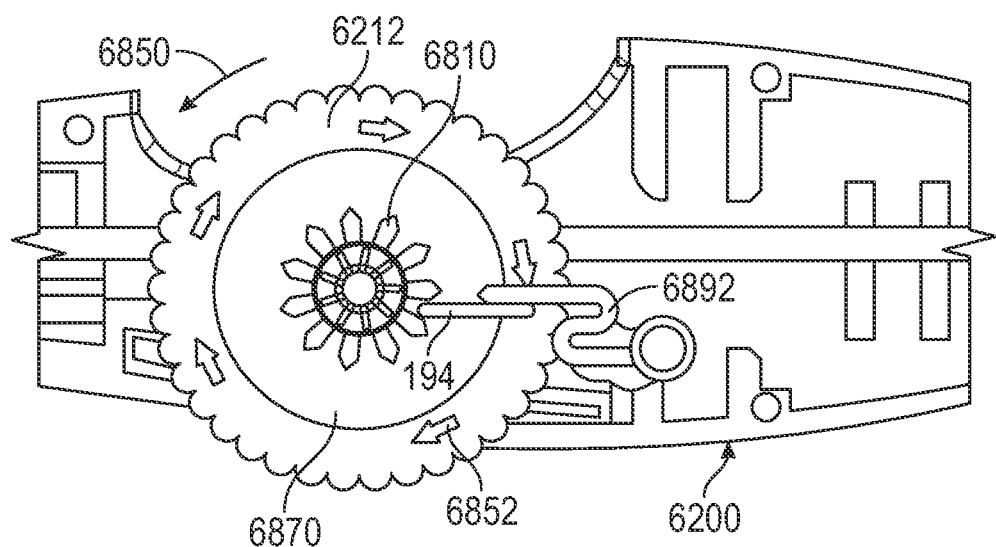
FIG. 72 is a view that is similar to FIG. 71 in a disengaged state.
Figure 73:
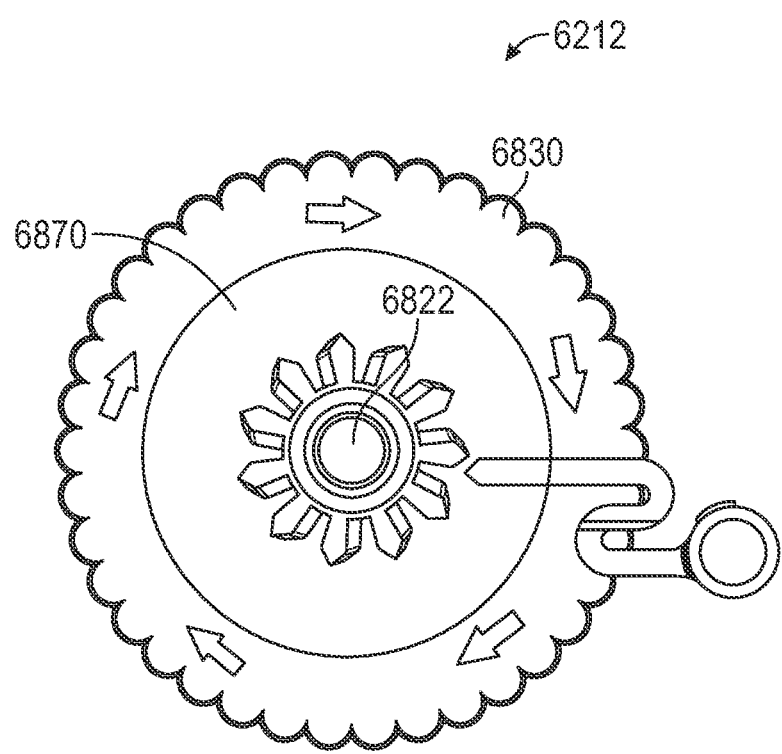
FIG. 73 is a side view of an indexing wheel of the handle illustrated by FIG. 62 in the disengaged state.

FIGS. 72 and 73 illustrate the ratchet mechanism 6800 with the ratchet arm 6892 moved out of engagement with the projections 6810. This allows the drive wheel 6212 to be turned in either direction. For example, the ratchet mechanism 6800 may be placed in the disengaged condition to allow the drive wheel 6212 to be turned in either direction as the docking station 10 is being deployed.

In ratchet systems, it is common to place the ratchet teeth on the outer perimeter of the wheel. By putting the teeth on the face of the wheel, the radial diameter of the wheel can be reduced, saving space. It also allows the outer perimeter of the wheel to be used as a grip for the thumb rather than, for example, having a second wheel for gripping that is in engagement with a first wheel. The wheel itself is also allowed to be thinner. The wheel may be made of any suitable material, such as polycarbonate.

Figure 71:
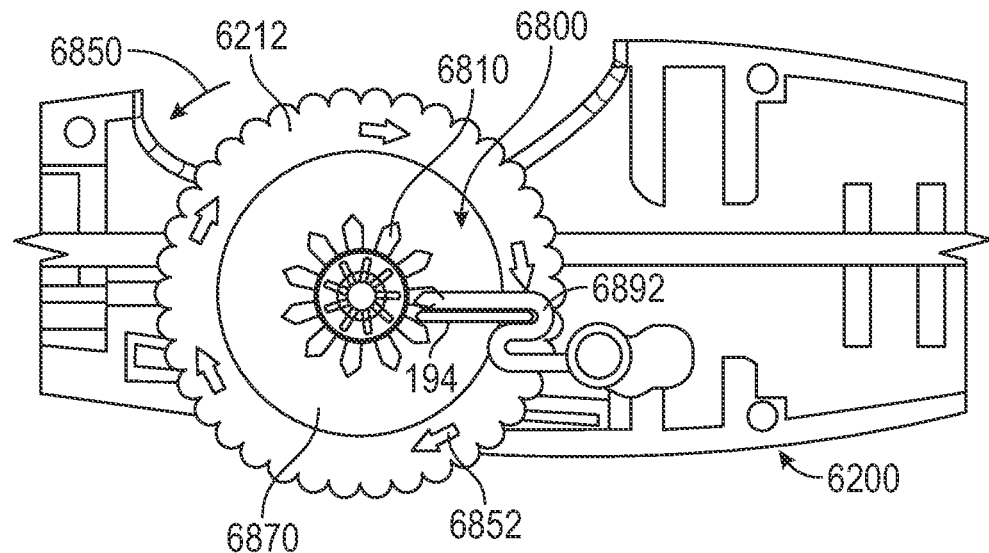
FIG. 71 is a partial sectional view of the indexing wheel illustrated by FIG. 68 disposed in a handle housing.

Referring to FIG. 71, in one embodiment the ratchet arm 6892 can be bent so that a portion of the arm can rest on a stabilizing bar 194 extending from a housing wall or otherwise located within the housing, to prevent the arm 6892 from twisting as force from movement of the wheel is applied to the arm.

The foregoing primarily describes embodiments of docking stations that are self-expanding. But the docking stations and/or delivery devices shown and described herein can be modified for delivery of balloon-expandable and/or mechanically-expandable docking devices, within the scope of the present disclosure. That is to say, delivering balloon-expandable and/or mechanically-expandable docking stations to an implantation location can be performed percutaneously using modified versions of the delivery devices of the present disclosure. In general terms, this includes providing a transcatheter assembly that can include a delivery sheath and/or additional sheaths as described above. In the case of balloon-expandable docking stations, the devices generally further include a delivery catheter, a balloon catheter, and/or a guide wire. A delivery catheter used in a balloon-expandable type of delivery device can define a lumen within which the balloon catheter is received. The balloon catheter, in turn, defines a lumen within which the guide wire is slideably disposed. Further, the balloon catheter includes a balloon that is fluidly connected to an inflation source. With the docking station mounted on the balloon, the transcatheter assembly is delivered through a percutaneous opening in the patient via the delivery device. Once the docking station is properly positioned, the balloon catheter is operated to inflate the balloon, thus transitioning the docking station to an expanded arrangement.

In view of the many possible embodiments to which the principles of the disclosed invention may be applied, it should be recognized that the illustrated embodiments are only preferred examples of the invention and should not be taken as limiting the scope of the invention. All combinations or subcombinations of features of the foregoing exemplary embodiments are contemplated by this application. The scope of the invention is defined by the following claims. We therefore claim as our invention all that comes within the scope and spirit of these claims.

The invention claimed is:

1. An expandable docking station frame comprising:
a waist portion;
a sealing portion connected to the waist portion, the sealing portion being expandable radially outward of the waist portion to provide a seal against a first location of an inner surface of a circulatory system at a deployed position over a range of sizes of expansion; and
a retaining portion connected to the sealing portion, the retaining portion being expandable radially outward to engage a second location of the inner surface of the circulatory system at the deployed position, to retain the docking station at the deployed position in the circulatory system;
wherein when the expandable docking station frame is in an expanded and unconstrained state, the sealing portion and the retaining portion are joined by a concave profile portion radially inward of each of a first outermost diameter of the sealing portion and a second outermost diameter of the retaining portion; and
wherein the second outermost diameter of the retaining portion is defined by a flared axially endmost portion of the docking station frame.

2. The expandable docking station frame of claim 1, wherein the sealing portion defines a convex profile portion.

3. The expandable docking station frame of claim 1, wherein the retaining portion is configured to engage the second location of the inner surface of the circulatory system at an angle between 30° and 60° from perpendicular to the inner surface of the circulatory system.

4. The expandable docking station frame of claim 1, wherein the second outermost diameter of the retaining portion is larger than the first outermost diameter of the sealing portion.

5. The expandable docking station frame of claim 1, wherein the concave profile portion is radially outward of the waist portion.

6. The expandable docking station frame of claim 1, wherein the expandable docking station frame comprises a lattice of metal struts.

7. The expandable docking station frame of claim 6, wherein the lattice of metal struts defines a plurality of diamond-shaped cells.

8. The expandable docking station frame of claim 6, wherein the lattice of metal struts defines a first row of cells disposed on a first side of the waist portion, a second row of cells aligned with the waist portion, and a third row of cells disposed on a second side of the waist portion opposite the first side.

9. The expandable docking station frame of claim 8, further comprising an impermeable cover disposed on at least the first and second rows of cells.

10. The expandable docking station frame of claim 9, wherein the third row of cells is covered by the impermeable cover.

11. The expandable docking station frame of claim 9, wherein the third row of cells is uncovered by the impermeable cover.

12. The expandable docking station frame of claim 9, wherein the sealing portion is defined by the first row of cells and the impermeable cover.

13. The expandable docking station frame of claim 8, wherein the retaining portion is defined by the first row of cells.

14. The expandable docking station frame of claim 1, wherein the retaining portion is disposed on a first side of the waist portion and the sealing portion is disposed on the first side of the waist portion between the waist portion and the retaining portion.

15. The expandable docking station frame of claim 14, wherein the retaining portion is a first retaining portion, the expandable docking station frame further comprising a second retaining portion disposed on a second side of the waist portion opposite the first side.

16. The expandable docking station frame of claim 15, wherein the sealing portion is a first sealing portion, the expandable docking station frame further comprising a second sealing portion disposed on the second side of the waist portion between the waist portion and the second retaining portion.

17. A system comprising
an expandable docking station frame including:
a waist portion;
a sealing portion connected to the waist portion, the sealing portion being expandable radially outward of the waist portion to provide a seal against a first location of an inner surface of a circulatory system at a deployed position over a range of sizes of expansion; and
a retaining portion connected to the sealing portion, the retaining portion being expandable radially outward to engage a second location of the inner surface of the circulatory system at the deployed position, to retain the docking station at the deployed position in the circulatory system; and
a catheter including a sleeve configured to retain the expandable docking station prior to deployment in the circulatory system;
wherein when the expandable docking station frame is in an expanded and unconstrained state, the sealing portion and the retaining portion are joined by a concave profile portion radially inward of each of a first outermost diameter of the sealing portion and a second outermost diameter of the retaining portion; and wherein the second outermost diameter of the retaining portion is defined by a flared axially endmost portion of the docking station frame.

18. The system of claim 17, further comprising an expandable valve including an expandable frame that is expandable to engage the waist portion of the docking station and a valve element connected to the expandable frame.

19. A method of installing an expandable valve in a docking station, the method comprising:
expanding a docking station at a deployed position in a circulatory system such that:
a waist portion of the docking station expands to a deployed size;
a sealing portion of the docking station expands to a sealing size in sealing engagement with a first location of an inner surface of the circulatory system at the deployed position; and
a retaining portion of the docking station expands into engagement with a second location of the inner surface of the circulatory system at the deployed position;
wherein the sealing portion and the retaining portion are joined by a concave profile portion radially inward of each of a first outermost diameter of the expanded sealing portion and a second outermost diameter of the expanded retaining portion; and
expanding a frame of an expandable valve to engage the waist portion of the docking station.

20. The method of claim 19, wherein the retaining portion engages the second location of the inner surface of the circulatory system at an angle between 30° and 60° from perpendicular to the inner surface of the circulatory system.

21. The method of claim 19, wherein the second outermost diameter of the retaining portion is defined by a flared axially endmost portion of the docking station frame.

22. The method of claim 19, wherein the docking station comprises a lattice of metal struts forming an axially endmost first row of cells in the retaining portion, a second row of cells in the waist portion, and a third row of cells disposed at an axial end portion of the docking station frame, axially spaced apart from the retaining portion by the waist portion, and wherein the expandable docking station frame further comprises an impermeable cover disposed on the first and second rows of cells, wherein the third row of cells is uncovered by the impermeable cover.

23. An expandable docking station frame comprising:
a waist portion;
a sealing portion connected to the waist portion, the sealing portion being expandable radially outward of the waist portion to provide a seal against a first location of an inner surface of a circulatory system at a deployed position over a range of sizes of expansion; and
a retaining portion connected to the sealing portion, the retaining portion being expandable radially outward to engage a second location of the inner surface of the circulatory system at the deployed position, to retain the docking station at the deployed position in the circulatory system;
wherein when the expandable docking station frame is in an expanded and unconstrained state, the sealing portion and the retaining portion are joined by a concave profile portion radially inward of each of a first outermost diameter of the sealing portion and a second outermost diameter of the retaining portion;
wherein the expandable docking station frame comprises a lattice of metal struts forming an axially endmost first row of cells in the retaining portion, a second row of cells in the waist portion, and a third row of cells disposed at an axial end portion of the docking station frame, axially spaced apart from the retaining portion by the waist portion; and wherein the second outermost diameter of the retaining portion is defined by a flared axially endmost portion of the docking station frame;
wherein the expandable docking station frame further comprises an impermeable cover disposed on the first and second rows of cells, wherein the third row of cells is uncovered by the impermeable cover.

\* \* \* \* \*